US006190889B1

(12) United States Patent
Jones

(10) Patent No.: US 6,190,889 B1
(45) Date of Patent: Feb. 20, 2001

(54) METHODS FOR REMOVING PRIMER SEQUENCES AND BLOCKING RESTRICTION ENDONUCLEASE RECOGNITION DOMAINS

(75) Inventor: Douglas H. Jones, Iowa City, IA (US)

(73) Assignee: University of Iowa Research Foundation, Iowa City, IA (US)

(*) Notice: Under 35 U.S.C. 154(b), the term of this patent shall be extended for 0 days.

(21) Appl. No.: 09/226,683

(22) Filed: Jan. 7, 1999

Related U.S. Application Data

(62) Division of application No. 08/742,755, filed on Nov. 1, 1996, now Pat. No. 5,858,671.

(51) Int. Cl.$^7$ .................................................. C12P 19/34
(52) U.S. Cl. ........................................ 435/91.1; 435/91.2
(58) Field of Search .................................... 435/91.1, 91.2

(56) References Cited

U.S. PATENT DOCUMENTS

| | | | |
|---|---|---|---|
| 5,102,785 | 4/1992 | Livak et al. ............................. | 435/6 |
| 5,270,184 | * 12/1993 | Walker et al. ....................... | 435/91.2 |
| 5,403,708 | 4/1995 | Brennan et al. ........................ | 435/6 |
| 5,455,166 | * 10/1995 | Walker ................................. | 435/91.2 |
| 5,508,169 | 4/1996 | Deugau et al. .......................... | 435/6 |
| 5,552,278 | 9/1996 | Brenner .................................. | 435/6 |
| 5,591,609 | * 1/1997 | Aurbach .............................. | 435/91.2 |
| 5,599,675 | 2/1997 | Brenner .................................. | 435/6 |
| 5,604,097 | 2/1997 | Brenner .................................. | 435/6 |
| 5,695,934 | 12/1997 | Brenner .................................. | 435/6 |
| 5,712,124 | * 1/1998 | Walker ................................. | 435/91.2 |
| 5,714,330 | 2/1998 | Brenner .................................. | 435/6 |
| 5,763,175 | 6/1998 | Brenner .................................. | 435/6 |
| 5,858,671 | 1/1999 | Jones ...................................... | 435/6 |
| 6,017,701 | * 1/2000 | Sorge et al. ............................ | 435/6 |

FOREIGN PATENT DOCUMENTS

| | | |
|---|---|---|
| WO 91/02796 | 3/1991 | (WO) . |
| WO 92/15711 | 9/1992 | (WO) . |
| WO 93/21340 | 10/1993 | (WO) . |
| WO 95/27080 | 10/1995 | (WO) . |
| WO 96/12039 | 4/1996 | (WO) . |

OTHER PUBLICATIONS

Guilfoyle, R.A. et al., "Ligation–mediated PCR amplification of specific fragments from a Class–II restriction endonuclease total digest", *Nucleic Acids Research*, 25(9):1854–1858 (1997).
Jones, D.H., "An iterative and regenerative method for DNA sequencing", *Biotechniques*, 22(5):938–946 (1997).
Padgett, K.A. et al., "Creating seamless junctions independent of restriction sites in PCR cloning", *Gene*, 168:31–35 (1996).
Baxter, G. et al., "Microfabrication in Silicon Microphysiometry," *Clin. Chem.*, vol. 40, No. 9, 1800–1804 (1994).
Beattie, K. et al., "Advances in Genosensor Research", *Clin. Chem.*, vol. 41, No. 5, 700–706 (1995).

Brenner, S. and Livak, K., "DNA Fingerprinting by Sampled Sequencing," *Proc. Natl. Acad. Sci. USA*, vol. 86, 8902–8906 (1989).
Broude, N. et al., "Enhanced DNA Sequencing by Hybridization," *Proc. Natl. Acad. Sci. USA*, vol. 91, 3072–3076 (1994).
Burns, M. et al., "Microfabricated Structures for Integrated DNA Analysis," *Proc. Natl. Acad. Sci. USA*, vol. 93, 5556–5561 (1996).
Caetano–Anollés, G. et al., "Primer–Template Interactions During DNA Amplification Fingerprinting with Single Arbitrary Oligonucleotides," *Mol. Gen. Genet.*, vol. 235, 157–165 (1992).
Canard, B. and Sarfati, R.S., "DNA Polymerase Fluorescent Substrates with Reversible 3'–tags," *Gene*, vol. 148, 1–6 (1994).
Carrano, A.V. et al., "A High–Resolution, Fluorescence–Based, Semiautomated Method for DNA Fingerprinting," *Genomics*, vol. 4, 129–136 (1989).
Cheng, J. et al., "Chip PCR. II. Investigation of Different PCR Amplification Systems in Microfabricated Silicon–Glass Chips," *Nucleic Acids Research*, vol. 24, No. 2, 380–385 (1996).
Chetverin, A. and Kramer, F., "Oligonucleotide Arrays: New Concepts and Possibilities," *BioTechnology*, vol. 12, 1093–1099 (1994).
Davis, L. et al., "Rapid DNA Sequencing Based Upon Single Molecule Detection," *Genetic Analysis, Techniques, and Applications*, vol. 8, No. 1, 1–7 (1991).
Drmanac, R. et al., "DNA Sequence Determination by Hybridization: A Strategy for Effecient Large–Scale Sequencing," *Science*, vol. 260, 1649–1652 (1993).
Eggers, M. and Ehrlich, D., "A Review of Microfabricated Devices for Gene–Based Diagnostics," *Hematologic Pathology*, vol. 9, No. 1, 1–15 (1995).
Eggers, M. et al., "A Microchip for Quantitative Detection of Molecules Utilizing Luminescent and Radioisotope Reporter Groups," *BioTechniques*, vol. 17, No. 3, 516–524 (1994).

(List continued on next page.)

*Primary Examiner*—Kenneth R. Horlick
(74) *Attorney, Agent, or Firm*—Lahive & Cockfield, LLP; Elizabeth A. Hanley, Esq.; Peter C. Lauro, Esq.

(57) ABSTRACT

An iterative and regenerative method for sequencing DNA is described. This method sequences DNA in discrete intervals starting at one end of a double stranded DNA segment. This method overcomes problems inherent in other sequencing methods, including the need for gel resolution of DNA fragments and the generation of artifacts caused by single-stranded DNA secondary structures. A particular advantage of this invention is that it can create offset collections of DNA segments and sequence the segments in parallel to provide continuous sequence information over long intervals. This method is also suitable for automation and multiplex automation to sequence large sets of segments.

17 Claims, 9 Drawing Sheets

OTHER PUBLICATIONS

Gibbs, R. et al., "Identification of Mutations Leading to the Lesch–Nyhan Syndrome by Automated Direct DNA Sequencing of In Vitro Amplified cDNA," *Proc. Natl. Acad. Sci. USA*, vol. 86, 1919–1923 (1989).

Green, E. and Green, P., "Sequence–tagged Site (STS) Content Mapping of Human Chromosomes: Theoretical Considerations and Early Experiences," *PCR Methods and Applications*, vol. 1, 77–90 (1991).

Gyllensten, U. and Allen, M., "PCR–based HLA Class II Typing," *PCR Methods and Applications*, vol. 1, 91–98 (1991).

Gyllensten, U. and Erlich H., "Generation of Single–Stranded DNA by the Polymerase Chain Reaction and its Application to Direct Sequencing of the HLA–DQA Locus," *Proc. Natl. Acad. Sci. USA*, vol. 85, 7652–7656 (1988).

Han, J. and Rutter, W., "λgt22S, a Phage Expression Vector for the Directional Cloning of cDNA by the use of a Single Restriction Enzyme Sfil," *Nucleic Acids Research*, vol. 16, No. 24, 11837 (1988).

Jacobs, K. et al., "The Thermal Stability of Oligonucleotide Duplexes is Sequence Independent in Tetraalkylammonium Salt Solutions: Application to Identifying Recombinant DNA Clones," *Nucleic Acids Res.*, vol. 16, 4637–4650 (1988).

Kikuchi, Y. et al., "Optically Accessible Microchannels Formed in a Single–Crystal Silicon Substrate for Studies of Blood Rheology," *Microvascular Research*, vol. 44, 226–240, (1992).

Kobayashi, M. et al., "Fluorescence–based DNA Minisequence Analysis for Detection of Known Single–base Changes in Genomic DNA," *Molecular and Cellular Probes*, vol. 9, 175–182 (1995).

Kohsaka, H. and Carson, D., "Solid–Phase Polymerase Chain Reaction," *Journal of Clinical Laboratory Analysis*, vol. 8, 452–455 (1994).

Kricka, L. et al., "Imaging of Chemiluminescent Reactions in Mesoscale Silicon–Glass Microstructures," *J Biolumin Chemilumin*, vol. 9, 135–138 (1994).

Kuppuswamy, M. et al., "Angle Nucleotide Primer Extension to Detect Genetic Diseases: Experimental Application to Hemophilia B (Factor IX) and Cystic Fibrosis Genes," *Proc. Natl. Acad. Sci. USA*, vol. 88, 1143–1147 (1991).

Lagerkvist, A. et al., "Manifold Sequencing: Effecient Processing of Large Sets of Sequencing Reactions," *Proc. Natl. Acad. Sci. USA*, vol. 91, 2245–2249 (1994).

Lamture, J. et al., "Direct Detection of Nucleic Acid Hybridization on the Surface of a Charge Coupled Device," *Nucleic Acids Research*, vol. 22, No. 11, 2121–2125 (1994).

Mauro, J. et al., "Fiber–Optic Fluorometric Sensing of Polymerase Chain Reaction–Amplified DNA Using an Immobilized DNA Capture Protein," *Analytical Biochemistry*, vol. 235, 61–72 (1996).

Maxam, A. and Gilbert, W., "A New Method for Sequencing DNA," *Proc. Natl. Acad. Sci. USA*, vol. 74, No. 2, 560–564 (1977).

Metzker, M. et al., " Termination of DNA Synthesis by Novel 3'–Modified–Deoxyribonucleoside 5'–Triphosphates," *Nucleic Acids Res.*, vol. 22, No. 20, 4259–4267 (1994).

Nikiforov, T. et al., "Genetic Bit Analysis: A Solid Phase Method for Typing Single Nucleotide Polymorphisms," *Nucleic Acids Res.*, vol. 22, No. 20, 4167–4175 (1994).

Riccelli, P. and Benight, A., "Tetramethylammonium Does not Universally Neutralize Sequence Dependent DNA Stability," *Nucleic Acids Res.*, vol. 21, No. 16, 3785–3788 (1993).

Rosenthal, A. et al., "Large–Scale Production of DNA Sequencing Templates by Microtitre Format PCR," *Nucleic Acids Research*, vol. 21, No. 1, 173–174 (1993).

Sanger, F. et al., "DNA Sequencing with Chain–Terminating Inhibitors," *Proc. Natl. Acad. Sci. USA*, vol. 74, No. 12, 5463–5467 (1977).

Shoffner, M. et al., "Chip PCR. I. Surface Passivation of Microfabricated Silicon–Glass Chips for PCR," *Nucleic Acids Research*, vol. 24, No. 2, 375–379 (1996).

Sokolov, B., "Primer Extension Technique for the Detection of Single Nucleotide in Genomic DNA," *Nucleic Acids Res.*, vol. 18, No. 12, 3671 (1989).

Straus et al. (1990) "Genomic subtraction for cloning DNA corresponding to deletion mutations" *Proc. Natl. Acad. Sci. USA* 87:1889–1893.

Strezoska, Z. et al., "DNA Sequencing by Hybridization: 100 Bases Read by a Non–Gel–Based Method," *Proc. Natl. Acad. Sci. USA*, vol. 88, 10089–10093 (1991).

Syvänen, A. et al., "Convenient and Quantitative Determination of the Frequency of a Mutant Allele Using Solid–Phase Minisequencing: Application to Aspartylglucosaminuria in Finland," *Genomics*, vol. 12, 590–595 (1992).

Versalovic, J. et al., "Distribution of Repetitive DNA Sequences in Eubacteria and Application to Fingerprinting of Bacterial Genomes," *Nucleic Acid Res.*, vol. 19, No. 24, 6823–6831 (1991).

Warren, S., "The Expanding World of Trinucleotide Repeats," *Science*, vol. 271, 1374–1375 (1996).

Wilding, P. et al., "Manipulating and Flow of Biological Fluids in Straight Channels Micromachined in Silicon," *Clin. Chem.*, vol. 40, No. 1, 43–47 (1994).

Williams, J., et al., "Studies of Oligonucleotide Interactions by Hybridisation to Arrays: The Influence of Dangling Ends on Duplex Yield," *Nucleic Acids Res.*, vol. 22, No. 8, 1365–1367 (1994).

Woolley, A. and Mathies, R., "Ultra–High–Speed DNA Fragment Seperations Using Microfabricated Capillary Array Electrophoresis Chips," *Proc. Natl. Acad. Sci. USA*, vol. 91, 11348–11352 (1994).

\* cited by examiner

FIG. 6

Hemi-methylated *DpnI*
recognition domain

Methyl
|
CCATCCGTAAGATGATCTTCTGTGACTGGTGAGTACTCAACCAAGTCATTCTGAG
GGTAGGCATTCTACTAGAAGACACTGACCACTCATGAGTTGGTTCAGTAAGACTC 55 bp PCR product ↓ *DpnI*

TCTTCTGTGACTGGTGAGTACTCAACCAAGTCATTCTGAG
AGAAGACACTGACCACTCATGAGTTGGTTCAGTAAGACTC 40 bp product

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

CNNNCATCCG ACCCAGGCGT GCG                                            23

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

ANNNCATCCG ACCCAGGCGT GCG                                            23

(2) INFORMATION FOR SEQ ID NO:3:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

TNNNCATCCG ACCCAGGCGT GCG                                            23

(2) INFORMATION FOR SEQ ID NO:4:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

GNNNCATCCG ACCCAGGCGT GCG                                            23

(2) INFORMATION FOR SEQ ID NO:5:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

CGCACGCCTG GGTCGGATG                                                    19

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CNNNCATCCT CTGGGCTGCA CGGG                                              24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ANNNCATCCT CTGGGCTGCA CGGG                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TNNNCATCCT CTGGGCTGCA CGGG                                              24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GNNNCATCCT CTGGGCTGCA CGGG                                              24

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CCCGTGCAGC CCAGAGGATG                                                   20

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GTTTTCCTGG ATGATGCCCT GGC                                              23

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CATGCTTTGA TGACGCTTCT GTATC                                        25

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CNNNCATCCG ACCCAGGCGT GCG                                              23

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ANNNCATCCG ACCCAGGCGT GCG                                              23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TNNNCATCCG ACCCAGGCGT GCG                                              23

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GNNNCATCCG ACCCAGGCGT GCG        23

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CGCACGCCTG GGTCGGATG        19

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CNNNCATCCT CTGGGCTGCA CGGG        24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

ANNNCATCCT CTGGGCTGCA CGGG        24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TNNNCATCCT CTGGGCTGCA CGGG        24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
GNNNCATCCT CTGGGCTGCA CGGG                                            24
```

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
CCCGTGCAGC CCAGAGGATG                                                 20
```

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
CGCACGGCTG GGTCGGAGGA GNC                                             23
```

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
CGCACGGCTG GGTCGGAGGA GNA                                             23
```

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
CGCACGGCTG GGTCGGAGGA GNT                                             23
```

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

```
CGCACGGCTG GGTCGGAGGA GNG                                    23
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
CTCCTCCGAC CCAGCCGTGC G                                      21
```

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
GGTGCGCCAG TCCAGCGAGG AGNC                                   24
```

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
GGTGCGCCAG TCCAGCGAGG AGNA                                   24
```

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

```
GGTGCGCCAG TCCAGCGAGG AGNT                                   24
```

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GGTGCGCCAG TCCAGCGAGG AGNG                                      24

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CTCCTCGCTG GACTGGCGCA CC                                       22

(2) INFORMATION FOR SEQ ID NO:33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TCTGTTCTCA GTTTTCCTGG ATGAGGAGTG GCACC                    35

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

CGCACGGCTG GGTCGGAGGA G                                         21

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

GGTGCGCCAG TCCAGCGAGG AG                                       22

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

NNNCATCCGA CCCAGGCGTG CG                                              22

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CGCACGCCTG GGTCGGATG                                                  19

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

NNNCATCCTC TGGGCTGCAC GGG                                             23

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CCCGTGCAGC CCAGAGGATG                                                 20

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

CCATCCGTAA GATGATCTTC TG                                              22

```
(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

CTCAGAATGA CTTGGTTG                                              18
```

METHODS FOR REMOVING PRIMER SEQUENCES AND BLOCKING RESTRICTION ENDONUCLEASE RECOGNITION DOMAINS

This application is a divisional application of Ser. No. 08/742,755 filed on Nov. 1, 1996, U.S. Pat. No. 5,858,671. The contents of all of the aforementioned application are hereby incorporated by reference.

BACKGROUND OF THE INVENTION

Analysis of DNA with currently available techniques provides a spectrum of information ranging from the confirmation that a test DNA is the same or different than a standard sequence or an isolated fragment, to the express identification and ordering of each nucleotide of the test DNA. Not only are such techniques crucial for understanding the function and control of genes and for applying many of the basic techniques of molecular biology, but they have also become increasingly important as tools in genomic analysis and a great many non-research applications, such as genetic identification, forensic analysis, genetic counseling, medical diagnostics and many others. In these latter applications, both techniques providing partial sequence information, such as fingerprinting and sequence comparisons, and techniques providing full sequence determination have been employed (Gibbs et al., *Proc. Natl. Acad. Sci USA* 1989; 86:1919–1923; Gyllensten et al., *Proc. Natl. Acad. Sci USA* 1988; 85:7652–7656; Carrano et al., *Genomics* 1989; 4:129–136; Caetano-Anolles et al., *Mol. Gen. Genet.* 1992; 235:157–165; Brenner and Livak, *Proc. Natl. Acad. Sci USA* 1989; 86:8902–8906; Green et al., PCR Methods and Applications 1991; 1:77–90; and Versalovic et al., *Nucleic Acid Res.* 1991; 19:6823–6831).

DNA sequencing methods currently available require the generation of a set of DNA fragments that are ordered by length according to nucleotide composition. The generation of this set of ordered fragments occurs in one of two ways: chemical degradation at specific nucleotides using the Maxam Gilbert method (Maxam A M and W Gilbert, *Proc Natl Acad Sci USA* 1977; 74:560–564) or dideoxy nucleotide incorporation using the Sanger method (Sanger F, S Nicklen, and A R Coulson, *Proc Natl Acad Sci USA* 1977; 74:5463–5467) so that the type and number of required steps inherently limits both the number of DNA segments that can be sequenced in parallel, and the number of operations which may be carried out in sequence. Furthermore, both methods are prone to error due to the anomalous migration of DNA fragments in denaturing gels. Time and space limitations inherent in these gel-based methods have fueled the search for alternative methods.

Several methods are under development that are designed to sequence DNA in a solid state format without a gel resolution step. The method that has generated the most interest is sequencing by hybridization. In sequencing by hybridization, the DNA sequence is read by determining the overlaps between the sequences of hybridized oligonucleotides. This strategy is possible because a long sequence can be deduced by matching up distinctive overlaps between its constituent oligomers (Strezoska Z, T Paunesku, D Radosavljevic, I Labat, R Drmanac, R Crkvenjakov, *Proc Natl Acad Sci USA* 1991; 88:10089–10093; Drmanac R, S Drmanac, Z Strezoska, T Paunesku, I Labat, M Zeremski, J Snoddy, W K Funkhouser, B Koop, L Hood, R Crkvenjakov, *Science* 1993; 260:1649–1652). This method uses hybridization conditions for oligonucleotide probes that distinguish between complete complementarity with the target sequence and a single nucleotide mismatch, and does not require resolution of fragments on polyacrylamide gels (Jacobs K A, R Rudersdorf, S D Neill, J P Dougherty, E L Brown, and E F Fritsch, *Nucleic Acids Res.* 1988; 16:4637–4650). Recent versions of sequencing by hybridization add a DNA ligation step in order to increase the ability of this method to discriminate between mismatches, and to decrease the length of the oligonucleotides necessary to sequence a given length of DNA (Broude N E, T Sano, C L Smith, C R Cantor, *Proc. Natl. Acad. Sci. USA* 1994;91:3072–3076, Drmanac R T, *International Business Communications*, Southborough, Mass.). Significant obstacles with this method are its inability to accurately position repetitive sequences in DNA fragments, inhibition of probe annealing by the formation of internal duplexes in the DNA fragments, and the influence of nearest neighbor nucleotides within and adjacent to an annealing domain on the melting temperature for hybridization (Riccelli P V, A S Benight, *Nucleic Acids Res* 1993;21:3785–3788, Williams J C, S C Case-Green, K U Mir, E M Southern. *Nucleic Acids Res* 1994;22:1365–1367). Furthermore, sequencing by hybridization cannot determine the length of tandem short repeats, which are associated with several human genetic diseases (Warren S T, *Science* 1996; 271:1374–1375). These limitations have prevented its use as a primary sequencing method.

The base addition DNA sequencing scheme uses fluorescently labeled reversible terminators of polymerase extension, with a distinct and removable fluorescent label for each of the four nucleotide analogs (Metzker M L, Raghavachari R, Richards S, Jacutin S E, Civitello A, Burgess K and R A Gibbs, *Nucleic Acids Res.* 1994; 22:42594267; Canard B and R S Sarfati, *Gene* 1994; 148:1–6). Incorporation of one of these base analogs into the growing primer strand allows identification of the incorporated nucleotide by its fluorescent label. This is followed by removal of the protecting/fluorescent group, creating a new substrate for template-directed polymerase extension. Iteration of these steps is designed to permit sequencing of a multitude of templates in a solid state format. Technical obstacles include a relatively low efficiency of extension and deprotection, and interference with primer extension caused by single-strand DNA secondary structure. A fundamental limitation to this approach is inherent in iterative methods that sequence consecutive nucleotides. That is, in order to sequence more than a handful nucleotides, each cycle of analog incorporation and deprotection must approach 100% efficiency. Even if the base addition sequencing scheme is refined so that each cycle occurs at 95% efficiency, one will have <75% of the product of interest after only 6 cycles ($0.95^6=0.735$). This will severely limit the ability of this method to sequence anything but very short DNA sequences. Only one cycle of template-directed analog incorporation and deprotection appears to have been demonstrated so far (Metzker M L, Raghavachari R, Richards S, Jacutin S E, Civitello A, Burgess K and R A Gibbs, *Nucleic Acids Res.* 1994; 22:4259–4267; Canard B and R S Sarfati, *Gene* 1994; 148:1–6). A related earlier method, which is designed to sequence only one nucleotide per template, uses radiolabeled nucleotides or conventional non-reversible terminators attached to a variety of labels (Sokolov B P, *Nucleic Acids Research* 1989;18:3671; Kuppuswamy M N, J W Hoffman, C K Kasper, S G Spitzer, S L Groce, and S P Bajaj, *Proc. Natl. Acad. Sci. USA* 1991; 88:1143–1147). Recently, this method has been called solid-phase minisequencing (Syvanen A C, E Ikonen, T Manninen, M Bengstrom, H Soderlund, P Aula, and L Peltonen, *Genomics* 1992; 12:590–595; Kobayashi M, Rappaport E, Blasband A, Semeraro A, Sartore M, Surrey S, Fortina P., *Molecular and Cellular Probes* 1995; 9:175–182) or genetic bit analysis (Nikiforov T T, R B Rendle, P Goelet, Y H Rogers, M L Kotewicz, S Anderson, G L Trainor, and M R Knapp, *Nucleic Acids Research* 1994; 22:4167–4175), and it has been used to verify the parentage of thoroughbred horses (Nikiforov T T, R B Rendle, P Goelet, Y H Rogers, M L Kotewicz, S Anderson, G L Trainor, and M R Knapp, *Nucleic Acids Research* 1994; 22:4167–4175).

An alternative method for DNA sequencing that remains in the development phase entails the use of flow cytometry to detect single molecules. In this method, one strand of a DNA molecule is synthesized using fluorescently labeled nucleotides, and the labeled DNA molecule is then digested by a processive exonuclease, with identification of the released nucleotides over real time using flow cytometry. Technical obstacles to the implementation of this method include the fidelity of incorporation of the fluorescently labeled nucleotides and turbulence created around the microbead to which the single molecule of DNA is attached (Davis L M, F R Fairfield, C A Harger, J H Jett, R A Keller, J H Hahn, L A Krakowski; B L Marrone, J C Martin, H L Nutter, R L Ratliff, E B Shera, DJ Simpson, S A Soper, *Genetic Analysis, Techniques, and Applications* 1991; 8:1–7). Furthermore, this method is not amenable to sequencing numerous DNA segments in parallel.

Another DNA sequencing method has recently been developed that uses class-IIS restriction endonuclease digestion and adaptor ligation to sequence at least some nucleotides offset from a terminal nucleotide. Using this method, four adjacent nucleotides have reportedly been sequenced and read following the gel resolution of DNA fragments. However, a limitation of this sequencing method is that it has built-in product losses, and requires many iterative cycles (International Application PCT/US95/03678).

Another problem exists with currently available technologies in the area of diagnostic sequencing. An ever widening array of disorders, susceptibilities to disorders, prognoses of disease conditions, and the like, have been correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations, and ras proto-oncogene mutations (Gullensten et al., PCR Methods and Applications, 1:91–98 (1991); International application PCT/US92/01675; and International application PCT/CA90/00267). A difficulty in determining DNA sequences associated with such conditions to obtain diagnostic or prognostic information is the frequent presence of multiple subpopulations of DNA, e.g., allelic variants, multiple mutant forms, and the like. Distinguishing the presence and identity of multiple sequences with current sequencing technology is impractical due to the amount of DNA sequencing required.

SUMMARY OF THE INVENTION

The present invention provides an alternative approach for sequencing DNA that does not require high resolution separations and that generates signals more amenable to analysis. The methods of the present invention can also be easily automated. This provides a means for readily analyzing DNA from many genetic loci. Furthermore, the DNA sequencing method of the present invention does not require the gel resolution of DNA fragments which allows for the simultaneous sequencing of cDNA or genomic DNA library inserts. Therefore, the full length transcribed sequences or genomes can be obtained very rapidly with the methods of the present invention. The method of the present invention further provides a means for the rapid sequencing of previously uncharacterized viral, bacterial or protozoan human pathogens, as well as the sequencing of plants and animals of interest to agriculture, conservation, and/or science.

The present invention pertains to methods which can sequence multiple DNA segments in parallel, without running a gel. Each DNA sequence is determined without ambiguity, as this novel method sequences DNA in discrete intervals that start at one end of each DNA segment. The method of the present invention is carried out on DNA that is almost entirely double-stranded, thus preventing the formation of secondary structures that complicate the known sequencing methods that rely on hybridization to single-stranded templates (e.g., sequencing by hybridization), and overcoming obstacles posed by microsatellite repeats, other direct repeats, and inverted repeats, in a given DNA segment. The iterative and regenerative DNA sequencing method described herein also overcomes the obstacles to sequencing several thousand distinct DNA segments attached to addressable sites on a matrix or a chip, because it is carried out in iterative steps and in various embodiments effectively preserves the sample through a multitude of sequencing steps, or creates a nested set of DNA segments to which a few steps are applied in common. It is, therefore, highly suitable for automation. Furthermore, the present invention particularly addresses the problem of increasing throughput in DNA sequencing, both in number of steps and parallelism of analyses, and it will facilitate the identification of disease-associated gene polymorphisms, with particular value for sequencing entire genomes and for characterizing the multiple gene mutations underlying polygenic traits. Thus, the invention pertains to novel methods for generating staggered templates and for iterative and regenerative DNA sequencing as well as to methods for automated DNA sequencing.

Accordingly, the invention features a method for identifying a first nucleotide n and a second nucleotide n+x in a double stranded nucleic acid segment. The method includes (a) digesting the double stranded nucleic acid segment with a restriction enzyme to produce a double stranded molecule having a single stranded overhang sequence corresponding to an enzyme cut site; (b) providing an adaptor having a cycle identification tag, a restriction enzyme recognition domain, a sequence identification region, and a detectable label; (c) hybridizing the adaptor to the double stranded nucleic acid having the single-stranded overhang sequence to form a ligated molecule; (d) identifying the nucleotide n by identifying the ligated molecule; (e) amplifying the ligated molecule from step (d) with a primer specific for the cycle identification tag of the adaptor; and (f) repeating steps (a) through (d) on the amplified molecule from step (e) to yield the identity of the nucleotide n+x, wherein x is less than or equal to the number of nucleotides between a recognition domain for a restriction enzyme and an enzyme cut site.

In another aspect, the invention features a method for sequencing an interval within a double stranded nucleic acid segment by identifying a first nucleotide n and a second nucleotide n+x in a plurality of staggered double stranded molecules produced from the double stranded nucleic acid segment. The method includes (a) attaching an enzyme recognition domain to different positions along the double stranded nucleic acid segment within an interval no greater than the distance between a recognition domain for a restriction enzyme and an enzyme cut site, such attachment occurring at one end of the double stranded nucleic acid segment; (b) digesting the double stranded nucleic acid segment with a restriction enzyme to produce a plurality of staggered double stranded molecules each having a single stranded overhang sequence corresponding to the cut site; (c) providing an adaptor having a restriction enzyme recognition domain, a sequence identification region, and a detectable label; (d) hybridizing the adaptor to the double stranded nucleic acid having the single-stranded overhang sequence to form a ligated molecule; (e) identifying a nucleotide n within a staggered double stranded molecule by identifying the ligated molecule; (f) repeating steps (b) through (e) to yield the identity of the nucleotide n+x in each of the staggered double stranded molecules having the single strand overhang sequence thereby sequencing an interval within the double stranded nucleic acid segment, wherein x is greater than one and no greater than the number of nucleotides between a recognition domain for a restriction enzyme and an enzyme cut site.

In another aspect, the invention features a method for identifying a first nucleotide n and a second nucleotide n+x in a double stranded nucleic acid segment. The method includes (a) digesting the double stranded nucleic acid segment with a restriction enzyme to produce a double stranded molecule having a 5' single stranded overhang sequence corresponding to an enzyme cut site; (b) identifying the nucleotide n by template-directed polymerization with a labeled nucleotide or nucleotide terminator; (c) providing an adaptor having a cycle identification tag and a restriction enzyme recognition domain; (d) ligating the adaptor to the double stranded nucleic acid to form a ligated molecule; (e) amplifying the ligated molecule from step (d) with a primer specific for the cycle identification tag of the adaptor; and (f) repeating steps (a) through (b) on the amplified molecule from step (e) to yield the identity of the nucleotide n+x, wherein x is less than or equal to the number of nucleotides between a recognition domain for a restriction enzyme and an enzyme cut site.

Yet another aspect of the invention pertains to a method for sequencing an interval within a double stranded nucleic acid segment by identifying a first nucleotide n and a second nucleotide n+x in a plurality of staggered double stranded molecules produced from the double stranded nucleic acid segment. The method includes (a) attaching an enzyme recognition domain to different positions along the double stranded nucleic acid segment within an interval no greater than the distance between a recognition domain for a restriction enzyme and an enzyme cut site, such attachment occurring at one end of the double stranded nucleic acid segment; (b) digesting the double stranded nucleic acid segment with a restriction enzyme to produce a plurality of staggered double stranded molecules each having a 5' single stranded overhang sequence corresponding to the cut site; (c) identifying a nucleotide n within a staggered double stranded molecule by template-directed polymerization with a labeled nucleotide or nucleotide terminator; (d) providing an adaptor having a restriction enzyme recognition domain; e) ligating the adaptor to the double stranded nucleic acid to form a ligated molecule; (f) repeating steps (b) through (c) to yield the identity of the nucleotide n+x in each of the staggered double stranded molecules having the single strand overhang sequence thereby sequencing an interval within the double stranded nucleic acid segment, wherein x is greater than one and no greater than the number of nucleotides between a recognition domain for a restriction enzyme and an enzyme cut site.

The invention also pertains to a method for removing all or a part of a primer sequence from a primer extended product. The method includes (a) providing a primer sequence encoding a methylated portion of a restriction endonuclease recognition domain, wherein recognition of the domain by a restriction endonuclease requires at least one methylated nucleotide; (b) polymerizing by a template-directed primer extension using the primer and a nucleic acid segment to generate a primer extended product; and (c) digesting the primer extended product with a restriction endonuclease that recognizes the resulting double-stranded restriction endonuclease recognition domain encoded by the primer sequence in the primer extended product.

A still further aspect of the invention pertains to a method for blocking a restriction endonuclease recognition domain in a primer extended product. The method includes (a) providing a primer with at least one modified nucleotide, wherein the modified nucleotide blocks an enzyme recognition domain, and at least a portion of the enzyme recognition domain sequence is encoded in the primer; (b) polymerizing by a template-directed primer extension using the primer and a nucleic acid segment to generate a primer extended product; and (c) digesting the primer extended product with an enzyme that recognizes a double-stranded enzyme recognition domain in the primer extended product.

In another aspect of the invention there is provided a method and device for automated sequencing of double-stranded DNA segments with nested single strand overhang templates, wherein a plurality of double-stranded DNA segments are immobilized at sites of a microtiter support or chip array having a plurality of sample holders arrayed in a matrix of positions on the support. Each DNA segment has an end comprising a single-strand overhang template sequence no longer than about twenty nucleotides in length. The device then implements a protocol simultaneously treating all sample holders with one or more reagents which selectively react with at least one nucleotide of the single-strand overhang template to effectively label the material at each holder, then reading the array by automated detection to determine at least one nucleotide of the single-strand overhang template at each position. Thereafter, the method proceeds by reducing length of each strand of the DNA segment at each holder by a fixed number n>1 at the overhang end, thus yielding a homologously ordered array of shorter and nested DNA segments, each with a single-strand overhang template sequence, which preferably remain immobilized at the same positions on the support where the treatment protocol is repeated to determine at least one nucleotide at each single-strand overhang sequence. The steps of treating, reading and reducing the length of the strands of the DNA segment at each holder by a number of n>1 nucleotides are iteratively performed as automated process steps to produce nested and progressively shorter DNA segments and to sequence the plurality of DNA segments immobilized at the array of sample holders in situ.

In another aspect the invention includes a method for automated sequencing of double stranded DNA segments by attaching a recognition domain to each segment to form a set of DNA segments having the recognition domain nested at an interval no greater than the distance between the recognition domain and its cut site for a given enzyme that recognizes the recognition domain; treating the DNA segments with an enzyme that recognizes the attached recognition domain and cuts each strand of each DNA segment to create an overhang template at a distance of >1 nucleotide along the DNA segment from the recognition domain so as to generate a set of nested overhang templates; and determining at least one nucleotide of each of the nested overhang templates. Thereafter, the method proceeds by reducing length of each strand at the end of the DNA segment with the overhang template by >1 nucleotide to produce a corresponding set of shorter DNA segments each with an overhang template. The step of reducing is performed by removing a block of nucleotides, so that each shorter DNA segment with an overhang template is a known subinterval of a previous DNA segment with overhang.

In another aspect of the invention there is provided a method and device for automated sequencing of double-stranded DNA segments, wherein a plurality of double-stranded DNA segments are immobilized at sites of a microtiter support or chip array having a plurality of sample holders arrayed in a matrix of positions on the support. Each DNA segment has an end comprising a single-strand overhang template sequence no longer than about twenty nucleotides in length. The device then simultaneously treats all sample holders with one or more reagents which selectively react with at least one nucleotide of the single-strand overhang template to effectively label the material at each holder, and reading the array by automated detection to determine at least one nucleotide of the single-strand overhang template at each position. Thereafter, the method proceeds by regenerating material at the respective sample holders by DNA amplification in vitro and reducing length of each strand of the regenerated DNA segment at each holder by a fixed number $n \geq 1$ at the overhang end, thus yielding a homologously ordered array of shorter and nested DNA segments, each with a single-strand overhang template sequence, which preferably remain immobilized at the same positions on the support, and the treatment protocol is repeated to determine at least one nucleotide at each single-strand overhang sequence. The steps of treating, reading, regenerating and reducing the length of the strands of the DNA segment at each holder by a number of n>1 nucleotides are iteratively performed as automated process steps to produce nested and progressively shorter DNA segments and to sequence the plurality of DNA segments immobilized at the array of sample holders in situ.

In another aspect the invention includes a method for automated sequencing of double stranded DNA segments by attaching a recognition domain to each segment to form DNA segments having the recognition domain, regenerating the template precursor by DNA amplification in vitro, treating the DNA segments with an enzyme that recognizes the attached recognition domain and cuts each strand of each DNA segment to create an overhang template at a distance of $\geq 1$ nucleotide along the DNA segment from the recognition domain, and determining at least one nucleotide of the overhang template. The method includes the step of reducing length of each strand at the end of the DNA segment with the overhang template by $\geq 1$ nucleotide to produce a corresponding set of shorter DNA segments each with an overhang template, the step of reducing being performed by removing a block of nucleotides, so that each shorter DNA segment with an overhang template is a known subinterval of a previous DNA segment with overhang.

The invention further contemplates an automated instrument for effectively performing the sequencing, wherein a stage carries the support on a device equipped for providing the respective buffers, solutions and reagents, for stepping or positioning the array for reading, and in some embodiments robotic manipulation for sample transfer, and heating for amplification, e.g., treating at least a portion of material at each sample holder with a primer and heat cycling to regenerate material at the respective sample holders. The stage may be rotatable, spinning to cause fluid provided at a central position to centrifugally flow across the array to alter material immobilized in the sample holders. Preferably the stage holds plural support arrays, and may operate robotically to transfer material from the sites of one support array to the sites of another support array, so that all the samples on one support may undergo one set of process steps in common (e.g., washing, digestion, labeling) while those on the other support undergo another (e.g., heating/amplification or scintillation reading).

Generally, the methods of the invention are applicable to all tasks where DNA sequencing is employed, including medical diagnostics, genetic mapping, genetic identification, forensic analysis, molecular biology research, and the like.

BRIEF DESCRIPTION OF THE DRAWINGS

FIG. 6 is a schematic diagram which illustrates the removal of primer encoded sequence from a PCR product by amplification with a primer encoding a DpnI recognition domain, which requires a methylated nucleotide, followed by cutting Dpn I. The primer sequences are underlined. The primer encoding the DpnI recognition domain had two mismatches with the original PCR template, and the two mismatched nucleotides are depicted in bold.

DETAILED DESCRIPTION OF THE INVENTION

Figure 1:
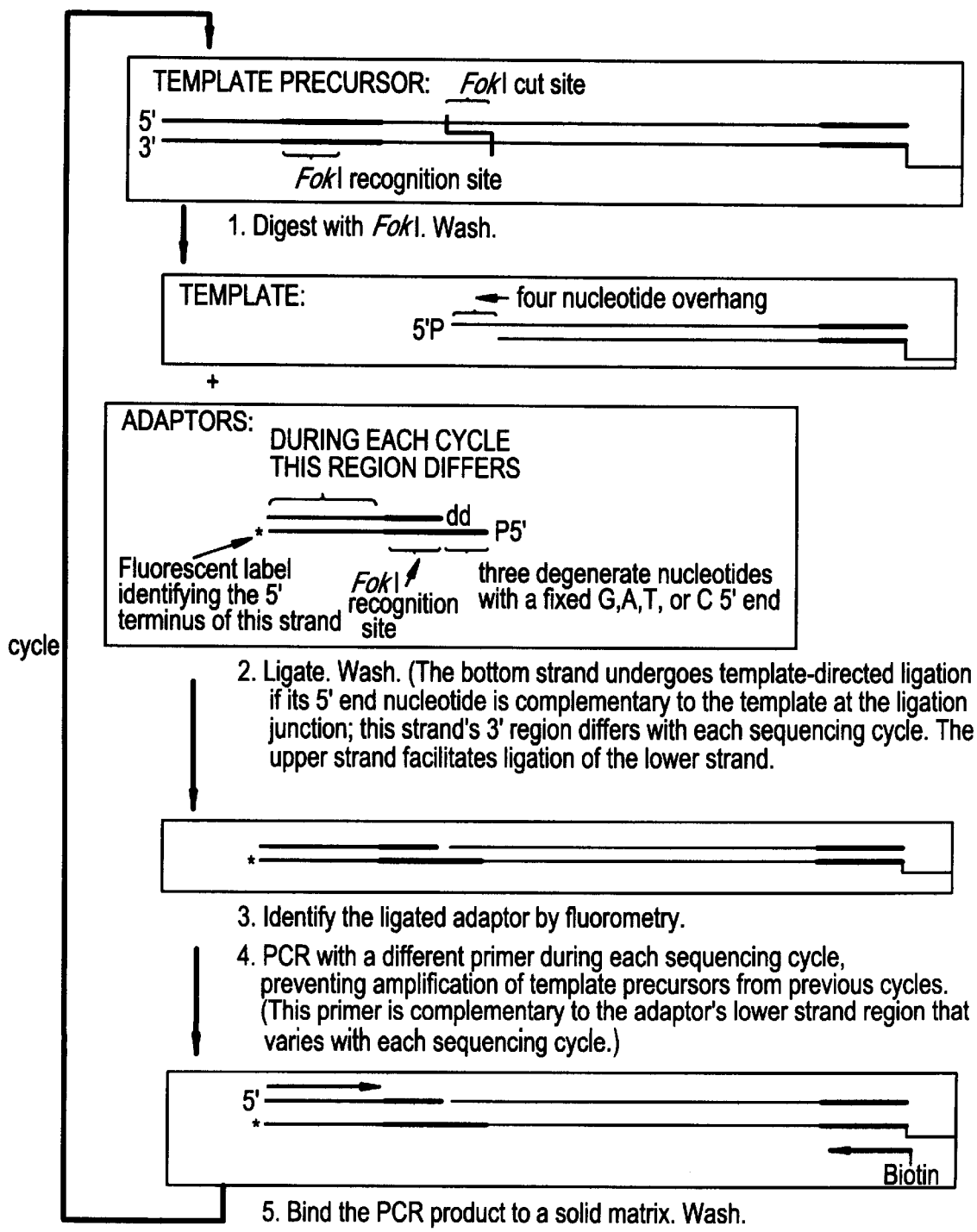
FIG. 1 is a schematic diagram of interval DNA sequencing method using a class-IIS restriction endonuclease that generates a 5' overhang (FokI), template-directed ligation to labeled adaptors, and PCR. DNA encoded by oligonucleotides or their PCR generated complements is depicted as thick lines. Following each cycle the template precursor is shortened.

The present invention pertains to an iterative and regenerative method for sequencing DNA that exploits the separation of the restriction enzyme recognition and cleavage domains in class-IIS restriction endonucleases, as well as adaptor ligation, to generate a series of sequencing templates that are separated from each other by a discrete interval. These sequencing templates constitute a set of single-strand overhangs that can then be sequenced by template-directed ligation, template-directed polymerization, or by stringent hybridization of oligonucleotides or oligonucleotide analogs.

The present invention features a method for identifying a first nucleotide n and a second nucleotide n+x in a double stranded nucleic acid segment. The method includes (a) digesting the double stranded nucleic acid segment with a restriction enzyme to produce a double stranded molecule having a single stranded overhang sequence corresponding to an enzyme cut site and (b) providing an adaptor having a cycle identification tag, a restriction enzyme recognition domain, a sequence identification region, and a detectable label. The method further includes (c) hybridizing the adaptor to the double stranded nucleic acid having the single-stranded overhang sequence to form a ligated molecule, (d) identifying the nucleotide n by identifying the ligated molecule, and (e) amplifying the ligated molecule from step (d) with a primer specific for the cycle identification tag of the adaptor. The method also includes (f) repeating steps (a) through (d) on the amplified molecule from step (e) to yield the identity of the nucleotide n+x, wherein x is less than or equal to the number of nucleotides between a recognition domain for a restriction enzyme and an enzyme cut site. As is described more fully below the order of steps (a) through (f) may vary with different embodiments of the invention.

As used herein, the term "nucleotide n" refers to a nucleotide along a given nucleic acid segment. "Nucleotide" is an art-recognized term and includes molecules which are the basic structural units of nucleic acids, e.g., RNA or DNA, and which are composed of a purine or pyrimidine base, a ribose or a deoxyribose sugar, and a phosphate group. A "modified nucleotide," as used herein, refers to a nucleotide that has been chemically modified, e.g., a methylated nucleotide. "Analogs" in reference to nucleotides includes synthetic nucleotides having modified base moieties and/or modified sugar moieties, e.g., as described generally by Scheit, Nucleotide Analogs (John Wiley, New York, 1980). Such analogs include synthetic nucleotides designed to enhance binding properties, reduce degeneracy, increase specificity, and the like. In the methods described herein, n designates a fixed position within a single stranded overhang sequence extending from each double stranded nucleic acid segment. Preferably, nucleotide n is selected by digesting a given double stranded nucleic acid segment with a restriction enzyme, e.g., a class IIS restriction endonuclease, to generate a 5' or a 3' single stranded overhang sequence corresponding to the cut site, and n is the first or the last unpaired nucleotide in the overhang sequence.

As used herein, the term "nucleotide n+x" refers to a second nucleotide in a given nucleic acid segment which is separated from nucleotide n by x nucleotides along a nucleic acid segment. For methods described herein, "x" is a number which is less than or equal to the number of nucleotides between a restriction enzyme recognition domain and the corresponding enzyme cut site for a given enzyme. By convention, "x" is defined by two integers which give the number of nucleotides between the recognition site and the hydrolyzed phosphodiester bonds of each strand of a nucleic acid segment. Preferably, x is no longer than about 9 nucleotides, more preferably x is no longer than about 18, 20 or 30 nucleotides, and advantageously it is in the range between about 40 and 60 nucleotides in length. For example, the recognition and cleavage properties of FokI are typically represented as "GGATG(9/13)" because it recognizes and cuts a double stranded nucleic acid as follows:

```
5'-...NNGGATGNNNNNNNNNN         NNNNNNNNNN...
3'-...NNCCTACNNNNNNNNNNNNN      NNNNNN...
``` where the bolded nucleotides are FokI's recognition site and the N's are arbitrary nucleotides and their complements.

As used herein, the language "restriction enzyme recognition domain" refers to a nucleotide sequence that allows a restriction enzyme to recognize this site and cut one or both strands of a nucleic acid segment at a fixed location with respect to the recognition domain. For class IIS restriction endonucleases, the cut site lies x nucleotides outside the recognition domain. Generally, the nucleotide sequence of the recognition domain is about 4 to about 10, more preferably about 4 to about 6, nucleotides in length. For example, for a class IIS restriction endonuclease, e.g., BseRI, the recognition domain is 6 nucleotides in length.

The language "enzyme cut site," refers to the location of a strand cleavage by an enzyme where this cleavage occurs in a fixed location with respect to the restriction enzyme recognition domain. For class IIS restriction endonuclease, the enzyme cut site is located x nucleotides away from the recognition domain. In one embodiment, the enzyme cut site is the site located the farthest from the restriction enzyme recognition domain. Preferably, the enzyme cut site is the site located closest to the restriction enzyme recognition domain.

"Enzyme" as the term is used in accordance with the invention means an enzyme, combination of enzymes, or other chemical reagents, or combinations chemical reagents and enzymes that when applied to a ligated molecule, discussed more fully below, cleaves the ligated molecule to generate a double stranded molecule having a single stranded overhang sequence corresponding to a cut site. An enzyme of the invention need not be a single protein, or consist solely of a combination of proteins. A key feature of the enzyme, or of the combination of reagents employed as an enzyme, is that its (their) cleavage site be separate from its (their) recognition site. It is important that the enzyme cleave the nucleic acid segment after it forms a ligated molecule with its recognition site; and preferably, the enzyme leaves a 5' or 3' protruding strand on the nucleic acid segment after cleavage.

Preferably, enzymes employed in the invention are natural protein endonucleases whose recognition site is separate from its cleavage site and whose cleavage results in a protruding strand on the nucleic acid segment. Most preferably, class IIS restriction endonucleases are employed as enzymes in the invention, e.g., as described in Szybalski et al., Gene, 100:13–26 (1991); Roberts et al., Nucleic Acids Research, 21:3125–3137 (1993);and Lovak and Brenner, U.S. Pat. No. 5,093,245. Class-IIS restriction endonucleases are a subclass of class-II restriction endonucleases that cut at precise distances away from their recognition domains, so that the recognition domains and cleavage domains are separated on the substrate DNA molecule (Szybalski W, S C Kim, N Hasan, A J Podhajska *Gene* 1991; 100:13–26). Following digestion with class-IIS restriction endonucleases, the sequence of the single-stranded end is independent of the recognition domain sequence. Class-IIS restriction endonucleases usually have asymmetric recognition domains, and class-IIS restriction endonucleases typically cut on one side of the recognition domain, resulting in one double-stranded cut per recognition site. Over 70 class-IIS restriction endonucleases have been isolated. Because the cleavage domain is separate from the recognition domain, methylation of nucleotides that lie within the cleavage domain will not effect cleavage, so long as the corresponding recognition domain is not methylated (Podhajska A J, W Szybalski *Gene* 1985;40:175–182, Podhajska A J, S C Kim, and W Szybalski *Methods in Enzymology* 1992; 216:303–309, Posfai G, W Szybalski *Gene* 1988; 69:147–151). Exemplary class IIS restriction endonucleases for use with the invention include AccBSI, AceIII, AciI, AclWI, AlwI, Alw26I, AlwXI, Asp26HI, Asp27HI, Asp35HI, Asp36HI, Asp40HI, Asp50HI, AsuHPI, BaeI, BbsI, BbvI, BbvII, Bbv16II, Bce83I, BcefI, BcgI, Bco5I, Bco116I BcoKI, BinI, Bli736I, BpiI, BpmI, Bpu10I, BpuAI, BsaI, BsaMI, Bsc9II, BscAI, BscCI, BseII, Bse3DI, BseNI, BseRI, BseZI, BsgI, BsiI, BsmI, BsmAI, BsmBI, BsmFI, Bsp24I, Bsp423I, BspBS3II, BspIS4I, BspKT5I, BspLU11III, BspMI, BspPI, BspST5I, BspTS514I, BsrI, BsrBI, BsrDI, BsrSI, BssSI, Bst1II, Bst71I, Bst2BI, BstBS32I, BstD102I, BstF5I, BstTS5I, Bsu6I, CjeI, CjePI, Eam1104I, EarI, Eco31I, Eco57I, EcoA4I, EcoO44II, Esp3I, FauI, FokI, GdiII, GsuI, HgaI, HphI, Ksp632I, MboII, MlyI, MmeI, Mn1I, Mva1269I, PhaI, PieI, RleAI, SapI, SfaNI, SimI, StsI, TaqII, TspII, TspRI, Tth111II, and VpaK32I, and isoschizomers thereof. Preferred endonucleases include FokI and BseRI.

Class-IIS restriction endonucleases have several applications, as outlined below. Class-IIS restriction endonucleases have been used in conjunction with an adaptor to act as a universal restriction endonuclease that can cut a single-stranded substrate at almost any predetermined site (Podhajska A J, W Szybalski *Gene* 1985;40:175–182, Podhajska A J, S C Kim, and W Szybalski *Methods in Enzymology* 1992; 216:303–309, Szybalski W. *Gene* 1985; 40:169–173). The adaptor consists of a double-stranded hairpin portion containing the recognition domain for the class IIS restriction endonuclease, and a single stranded end that is complementary to the single-stranded template to be cleaved. Following annealing of the adaptor to the single-stranded template (e.g. M13), the class-IIS restriction endonuclease can cleave this site. A hairpin adaptor has also been used to attach a radiolabel to one end of a single-stranded phagemid DNA, to facilitate Maxam-Gilbert sequencing (Goszcynski B, McGhee J D *Gene* 1991; 104:71–74).

Class-IIS restriction endonucleases have been used to trim vector inserts in order to generate deletions in a vector insert (Mormeneo S, R Knott, D Perlman *Gene* 1987; 61:21–30, Hasan N, J Kur, W Szybalski *Gene* 1989; 82:305–311, Hasan N. S C Kim, A J Podhajska, W Szybalski *Gene* 1986; 50:55–62). In this application, restriction endonuclease digestion removes a portion of the insert, and the resulting single-stranded ends are converted to blunt ends prior to intra-molecular ligation and the transformation of *E. coli*, generating a deletion mutant in the construct. If the class-IIS restriction endonuclease recognition domain is reconstituted, this process can be carried out again, generating a series of deletion mutants in the plasmid insert. This is not a sequencing method, and the single-strand overhangs that could act as sequencing templates are eliminated during the generation of each new plasmid construct.

Class-IIS restriction endonuclease digestion has been used as a mapping tool in a fluorescent fingerprinting procedure (Brenner S, Livak K J *Proc Natl Acad Sci USA* 1989; 86:8902–8906). In this method, 5' overhangs are generated by cleavage with a class IIS restriction endonuclease, using the recognition domains that already exist in the original DNA. Digestion is followed by labeling these ends using convention dNTPs and ddNTPs tagged with distinct fluorescent labels. This labeling constitutes conventional Sanger sequencing with fluorescently labeled terminators. The restriction fragments are then analyzed by denaturing polyacrylamide gel electrophoresis, with detection of emissions using a DNA sequencer. The labeled fragments are characterized by both size and terminal sequence, increasing the information content in DNA fingerprinting, allowing this method to distinguish restriction fragments that cannot be resolved by size alone.

The ability of class-IIS restriction endonucleases to generate ambiguous ends has also been used to amplify single restriction fragments from large DNA molecules ranging from about 50–250 kb in size (Smith D R *Methods and Applications* 1992; 2:21–27). In this method, digestion of the DNA molecule with a class-IIS restriction endonuclease that generates a 5' overhang is followed by ligation to a single adaptor, under conditions such that only a small subset of digested fragments have single-stranded ends that will successfully mediate template-directed ligation to this single adaptor. The ligated adaptor provides one target for subsequent PCR amplification of an unknown fragment. The second target is provided by a vectorette unit (bubble-tag) ligated to blunt ends produced by another restriction endonuclease. This strategy permits the amplification of a single unknown fragment from the relatively complex mixture. It is designed so that specific fragments can be isolated without prior knowledge of the nucleotide sequence of the target. These amplified fragments arise from random locations within the target. A similar strategy has been developed in which adaptors ligated to the class-IIS restriction endonuclease cut sites are called DNA indexers (Kato K. *Nucleic Acids Research* 1996; 24:394–395, Unrau P, Deugau K V *Gene* 1994; 145:163–169).

Restriction endonuclease digestion is frequently used to generate cohesive ends for cloning DNA segments into a vector. This can be accomplished by attaching restriction endonuclease recognition domains to the ends of a DNA fragment by ligation of a linker or adaptor. Alternatively, a recognition domain can be incorporated into the end of a nucleic acid sequence using a primer whose 5' end contains the restriction endonuclease recognition site of interest, followed by primer directed synthesis of the opposite strand. One limitation inherent in such primer directed incorporation of a restriction endonuclease recognition domain is that the fragment of interest cannot contain the recognition domain for this enzyme if the intact fragment is to be cloned by digestion with this restriction endonuclease, as cutting of internal sites would generate shorter segments. This particular obstacle was solved by Han and Rutter (Han J, Rutter W J *Nucleic Acids Res* 1988; 16:11837). They incorporated a recognition domain for the restriction endonuclease SfiI into an end of DNA segments by primer directed DNA synthesis. A primer encoding this recognition domain was used during first strand cDNA synthesis, but during this polymerization step methylated-dCTP was substituted for dCTP. This was followed by primer mediated synthesis of the opposite strand using all four normal dNTPs. Since the SfiI recognition domain contains the cytosine nucleoside, the primer extension with 6-methyl dCTP methylates one strand of each recognition domain for SfiI lying outside of this primer sequence, blocking cleavage mediated by any recognition domain lying outside of this primer sequence. Hemi-methylation of the recognition domains lying outside of the primer sequence allowed this restriction endonuclease to be used to clone intact segments containing recognition domains for this restriction endonuclease.

Padgett and Sorge have adapted primer directed hemi-methylation of recognition domains lying outside a primer encoded recognition domain, to a polymerase chain reaction (PCR) (Mullis K, Faloona F, Scharf S, Saiki R, Horn G, Erlich H. *Cold Spring Harbor Symposia on Quantitative Biology*, Cold Spring Harbor Laboratory, LI:263–273) format (Padgett K A, J A Sorge *Gene* 1996; 168:31–35). This strategy requires a recognition domain in which each strand has at least one nucleotide that is not contained in the other strand of this domain. A recognition domain with this characteristic allows one to use primer extension during the polymerase chain reaction (PCR) to hemi-methylate each of the recognition domains except for that recognition domain encoded by the amplifying primer. This is accomplished by using a methylated nucleotide that is not present in the recognition domain sequence that is antisense to the primer encoding this domain. By using a methylated DNTP that does not lie in the strand antisense to the recognition domain encoded in the amplifying primer, all the recognition domains in the PCR product are methylated except the recognition domain that is encoded by the amplifying primer. This strategy hemi-methylates each of the recognition domain in the PCR product except the primer-encoded recognition domain. This approach has been applied using a recognition domain for a class II-S restriction endonuclease, to generate recombinant constructs (Padgett K A, J A Sorge *Gene* 1996; 168:31–35).

The above described strategies permit a class-IIS recognition domain to be appended to the end of a DNA segment through primer extension, while hemi-methylating each recognition domain that lies within the original target, and they can be used to block cutting mediated by internal recognition domains without blocking cutting mediated by the primer-encoded recognition domain. The two strategies outlined above constitute portions of the preferred embodiments of the invention.

Preferably, prior to enzyme digestion, usually at the start of the sequencing operation, the nucleic acid segment is treated by blocking the enzyme recognition domains of the enzyme being employed. The blocking prevents undesired cleavage of the nucleic acid segment because of the fortuitous occurrence of enzyme recognition domains at interior locations in the nucleic acid segment. Blocking can be achieved in a variety of ways, including in vitro primer extension or in vitro primer extension with hemi-methylation, e.g., in vitro DNA amplification, or methylation of the enzyme recognition domain. For example, the DNA amplification can occur during or following the amplification of the ligated molecule. Hemi-methylation can be achieved in a variety of ways, including in vitro primer extension with a methylated nucleotide using a primer having the portion of an enzyme recognition domain that blocks enzyme recognition if it is hemi-methylated. Preferably, the restriction endonuclease employed recognizes a hemi-methylated enzyme recognition domain and a primer contains at least one methylated nucleotide in the methylated portion of the recognition domain.

The language "nucleic acid segment" or "a double stranded nucleic acid segment" is used interchangeably herein and refers to a double stranded polynucleotide of any length. In one embodiment of the invention, the nucleic acid segment can contain a single stranded overhang, a nick or a gap. For example, the nucleic acid segment of the invention can be a genomic DNA, a cDNA, a product of an in vitro DNA amplification, e.g., a PCR product, a product of a strand displacement amplification, or a vector insert. The length of the nucleic acid segment can vary widely; however, for convenience of preparation, lengths employed in conventional sequencing are preferred. Preferably, the nucleic acid segment of the invention is about 60 basepairs in length, more preferably it is about 100, 120, 150, 200, 300 or 600 basepairs in length, and most preferably it is about 1 to 2, or more kilobase pairs in length. Examples of other ranges of lengths include: from about 60 basepairs to about 1 or 2 kilobase pairs; from about 60 basepairs to about 600 basepairs; from about 60 basepairs to about 200 or 300 basepairs; and from about 60 basepairs to about 120 or 150 basepairs.

The nucleic acid segments can be prepared by various conventional methods. For example, the nucleic acid segments can be prepared as inserts of any of the conventional cloning vectors, including those used in conventional DNA sequencing. Extensive guidance for selecting and using appropriate cloning vectors is found in Sambrook et al., Molecular Cloning: A Laboratory Manual, Second Edition (Cold Spring Harbor Laboratory, New York, 1989), and the like references Sambrook et al and Innis et al., editors, PCR Protocols (Academic Press, New York, 1990) also provide guidance for using polymerase chain reactions to prepare nucleic acid segments. Preferably, cloned or PCR-amplified nucleic acid segments are prepared which permit attachment to magnetic beads, or other solid supports, for ease of separating the nucleic acid segment from other reagents used in the method. Protocols for such preparative techniques are described fully in Wahlberg et al., Electrophoresis, 13:547–551 (1992); Tong et al., Anal. Chem. 64:2672–2677 (1992); Hultman et al., Nucleic Acids Research, 17:4937–4946 (1989); Hultman et al., Biotechniques, 10:84–93 (1991); Syvanen et al., Nucleic Acids Research, 16:11327–11338 (1988); Dattagupta et al., U.S. Pat. No. 4,734,363; Uhlen, PCT application PCT/GB89/00304. Kits are also commercially available for practicing such methods, e.g. Dynabeads™ template preparation kit from Dynal AS (Oslo, Norway).

In one preferred embodiment of the invention, the nucleic acid segment is attached to a solid matrix. As used herein, the term "solid matrix" refers to a material in a solid form to which a DNA molecule can attach. Examples of a solid matrix include a magnetic particle, e.g., a magnetic streptavidin or a magnetic glass particle, a polymeric microsphere, a filter material, or the like. Preferably, the solid matrix used in the methods of the invention permits the sequential application of reagents to a DNA molecule without complicated and time-consuming purification steps.

The nucleic acid segments of the invention can also be used to generate a plurality of staggered double stranded nucleic acid molecules having a single stranded overhang sequence. This is desirable when the sequencing interval is designed to be more than one nucleotide, and one nuclectide is sequenced from a single template during each cycle. The language "double stranded nucleic acid molecules having a single stranded overhang sequence" is intended to include a nucleic acid molecule created by the following method: attachment of an enzyme recognition domain at different positions within an interval of a selected double stranded nucleic acid segment, and digestion of the selected double stranded nucleic acid segment with a corresponding restriction enzyme. Preferably, the interval is no greater than the distance between a restriction enzyme recognition domain and an enzyme cut site. The resulting double stranded nucleic acid molecules having a single stranded overhang sequence constitute a plurality of staggered double stranded nucleic acid molecules. The single strand overhang sequence in the staggered nucleic acid molecule may be either 5' or 3'. Preferably, the number of nucleotides in the overhang portion of the strand is in the range from about 2 to about 6 nucleotides depending on the enzyme used to digest the nucleic acid segment.

The language "sequencing an interval within a double stranded nucleic acid segment" is intended to include the sequencing which occurs by identifying nucleotides n and n+x in a plurality of staggered double stranded molecules produced from the selected double stranded nucleic acid segment. This allows one to sequence all of the nucleotides in a selected nucleic acid segment between the nucleotide n and nucleotide n+x. For example, for a class IIS restriction enzyme, e.g., FokI, that has a restriction enzyme recognition domain nine nucleotides away from its enzyme cut site, e.g., x=9, starting with nine staggered double stranded nucleic acid molecules will generate sequence information for all nucleotides found in the interval between nucleotide n and nucleotide n+x.

The staggered double stranded nucleic acid molecules having a single stranded overhang sequence can be prepared by various methods. For example, they can be generated by ligation of the initial nucleic acid segment to each of several adaptors with offset class-IIS recognition domains (Wu R, T Wu, R Anuradh, *Enzymology* 1987;152:343–349). This initial DNA segment to be sequenced can be a PCR product or a vector insert. If the PCR product is amplified using a DNA polymerase with terminal extendase activity, the resulting single nucleotide 3' overhang can be removed using a DNA polymerase with 3' exonuclease, such as $T_4$ DNA polymerase or Pfu DNA polymerase, prior to blunt end ligation to adaptors (Costa G L, M P Weiner, *Nucleic Acids Research* 1994;22:2423). Offset recognition domains can also be encoded into the amplification primers (Mullis K, Faloona F, Scharf S, Saiki R, Horn G, Erlich H., Cold Spring Harbor Symposia on Quantitative Biology, Cold Spring Harbor Laboratory, LI:263–273), resulting in distinct amplification products with offset recognition domains.

There are a variety of ways in which offset recognition domains can be appended to each of numerous inserts in a DNA library. For example, if a complete digest were carried out on genomic DNA with the frequent cutter Sau3AI, followed by a partial fill-in with dGTP and dATP, each insert would contain non-self-complementary DNA ends (Hung M C; P C Wensink. *Nucleic Acids Research.* 1984; 12: 1863–1874). The vector could be digested with SalI and undergo a partial fill-in reaction with dCTP and dTTP, resulting in linearized vectors with non-self-complementary DNA ends. In this case each insert DNA end is complementary to each vector DNA end, so that during DNA ligation with cut and partially filled-in inserts and vectors, the vast majority of the resulting clones will contain one insert (Zabarovsky E R, R L Allikmets. *Gene.* 1986; 42: 119–123). Following the isolation of individual clones, each insert can undergo PCR amplification using primers that anneal to the vector sequence, with one of the primers disabling the Sau3AI site in one side of each amplified insert by having a base mismatch to the Sau3AI site near its 3' end, or, preferably, a methylated nucleotide in the 3' end region of the primer (this primer's 3' end encoding at least part of the Sau3AI recognition domain (GATC), so that it will prime efficiently and its methylated nucleotide will block Sau3AI cutting of this end of the PCR product, allowing cutting of the opposite end of the PCR product). If the adenine is methylated, cutting can be done using MboI or DpnII, which share the recognition domain of Sau3AI but are blocked by dam methylation. Following digestion, one end of each insert will have a four nucleotide long end that can undergo ligation to an initial adaptor, so that ligations to distinct initial adaptors can append staggered recognition domains (for the class-IIS restriction endonuclease that will be used for sequencing) to each of the numerous inserts in the library.

An alternative approach is to generate a library of clones using randomly sheared DNA. These DNA fragments can be dephosphorylated and efficiently cloned with one insert per vector using a vector that requires inactivation of a selectable marker by DNA insertion to be viable in a given *E. coli* host (Bernard P. *BioTechniques.* 1996; 21: 320–323). Alternatively, a pool of inserts can be size selected over an agarose gel prior to cloning into a vector (Fleischmann R D, et al. *Science.* 1995; 269: 496–512). Using either approach, or other cloning strategies, each vector insert could be amplified using one primer that contains a methylated strand of the recognition domain for a restriction endonuclease that recognizes a hemi-methylated domain but does not recognize a non-methylated domain. This can be accomplished by using a primer that has one strand of the recognition domain sequence, with at least one methylated nucleotide, so that digestion with the corresponding restriction endonuclease will cut that one end of each amplified product, and no other sites. This can be carried out by amplification with a primer that contains one strand of the recognition domain for DpnI (with a methylated adenine). This strategy allows PCR amplification with normal nucleotides, as PCR with normal nucleotides effectively blocks internal DpnI recognition domains. Alternatively, each end could be amplified and digested using the strategy of Padgett and Sorge (Padgett K A, J A Sorge *Gene* 1996; 168:31–35), with either a regular class-II restriction endonuclease or with a class-IIS restriction endonuclease.

In this method, the opposite end of each nucleic acid segment is shared between each of the initial template precursors for a given nucleic acid segment to be sequenced. Each initial template precursor is attached to a solid matrix. A wide range of methods have been used to bind DNA to a solid matrix. If the template precursor is a PCR product, one primer can contain a moiety that is used to attach the PCR product to a solid matrix. For example, this primer can contain a biotin moiety or another reactive moiety such as an amine group or thiol group, permitting the attachment of the PCR product to a solid matrix (Syvanen A C, M Bengstrom, J Tenhunen and H Soderlund, *Nucleic Acids Research* 1988; 16:11327–11338; Stamm S, J Brosius, *Nucleic Acids Research* 1991; 19:1350; Lund V, R Schmid, D Rickwood and E Hornes, *Nucleic Acids Research* 1988; 16:10861–10880; Fahy E, G R Davis, L J DiMichele, S S Ghosh, *Nucleic Acids Research* 1993; 21:1819–1826; and Kohsaka H, A Taniguchi, D D Richman, D A Carson, *Nucleic Acids Research* 1993; 21:3469–3472). The solid matrix can be either immobile or dispersible. For example, for a DNA segment with a biotinylated end, an immobile solid matrix can be an avidin or streptavidin coated microtiter plate (Jeltsch A, A Fritz, J Alves, H Wolfes, A Pingoud, *Analytical Biochemistry* 1993; 213:234–240; Holmstrom K, L Rossen, O F Rasmussen, *Analytical Biochemistry* 1993; 209:278–283) or manifold support (Lagerkvist A, J Stewart, M Lagerstrom-Fermer, U Landegren, *Proc Natl Acad Sci USA* 1994; 91:2245–2249). The most readily available dispersible solid matrix is beads that can be suspended through shaking. Beads can be designed to be magnetically pelleted (Lund V, R Schmid, D Rickwood and E Homes *Nucleic Acids Research* 1988; 16:10861–10880, Hultman T, S Stahl, E Hornes, M Uhlen *Nucleic Acids Research* 1989; 17:49374946, Dawson B A, T Herman, J Lough *Journal of Biological Chemistry* 1989;264:12830–12837) or they can be pelleted through centrifugation (Syvanen A C, M Bengstrom, J Tenhunen and H Sodelund, *Nucleic Acids Research* 1988; 16:11327–11338; Stamm St, J Brosius, *Nucleic Acids Research* 1991; 19:1350). Use of a dispersible solid matrix diminishes steric obstacles in enzymatic reactions, and facilitates removal of a small aliquot to be amplified. An alternative approach that allows a small aliquot of a reaction to be removed and used as a template for amplification is to use a method of reversible capture. Reversible capture can be accomplished by using a cleavable linkage arm (such as a chemically cleavable linkage arm or a photocleavable linkage arm (Dawson B A, T Herman, J Lough *Journal of Biological Chemistry* 1989; 264:12830–12837, Olejnik J, E Krzymanska-Olejnik, K J Rothschild, *Nucleic Acids Research* 1996; 24:361–366), by using a primer-encoded DNA binding domain that can be unbound by denaturation (Lew A M, D J Kemp, *Nucleic Acids Research* 1989; 17:5859; Kemp D J, D B Smith, S J Foote, N Samaras, M G Peterson, *Proc Natl Acad Sci USA* 1989; 86:2423–2427; Kemp D J, *Methods in Enzymology* 1992; 216:116–126), or by the generation of a single stranded end during PCR, as such an end can reversibly anneal to its complement that is bound to a solid phase (Newton C R, D Holland, L E Heptinstall, I Hodgson, M D Edge, A F Markham, M J McLean, *Nucleic Acids Research* 1993; 21:1155–11162; Khudyakov Y E, L Gaur, J Singh, P Patel, H A Fields, *Nucleic Acids Research* 1994;22:1320–1321).

Another important aspect of the invention is the adaptor employed within the present invention. An adaptor of the invention is a double stranded or a single stranded polynucleotide having one or more of a cycle identification tag, a restriction enzyme recognition domain and a sequence identification region. Preferably, the adaptor may also include a detectable label, which in the particular embodiment of FIG. 1 is illustrated at the end opposite of the sequence identification region.

As used herein, the language "a cycle identification tag" refers to a unique nucleotide sequence that generates a primer annealing site, and a primer can anneal either to the unique sequence or its complement. The cycle identification tag is of a length which allows it to perform its intended finction. Examples of lengths include: from about 8 to about 60 nucleotides in length; from about 8 to about 30 or 40 nucleotides in length; and from about 8 to about 15 or 20 nucleotides in length. Ligation of this unique sequence to each double stranded nucleic acid segment having the single stranded overhang sequence permits regeneration of each nucleic acid segment using primer-directed DNA amplification in vitro (e.g., PCR), ameliorating the major limitations inherent in iterative methods for product generation, e.g., product losses and the accumulation of incompletely processed products.

The language "restriction enzyme recognition domain" has been defined above. In one embodiment of the invention, the adaptor contains only a single strand of a restriction enzyme recognition domain, because a single strand of the domain can function as a template for the generation of a double stranded restriction enzyme recognition domain through hybridization to its complement or through template-directed polymerase generation of its complement.

As used herein, the language "sequence identification region" refers to a region used to identify nucleotide n and/or nucleotide n+x in a selected nucleic acid segment. Preferably, the region used to identify nucleotide n and/or nucleotide n+x is a protruding nucleotide strand, e.g., a 5' or a 3' nucleotide strand. In one embodiment of the invention, the sequence identification region is capable of forming a duplex with the single stranded overhang sequence of the double stranded nucleic acid segment. Preferably, the sequence identification region comprises a number of degenerate nucleotides, usually between 1 and 4 degenerate nucleotides. In addition, the sequence identification region can also include a fixed nucleotide, e.g., a nucleotide whose sequence is known, at its most terminal nucleotide. Preferably, at each cycle, only those adaptors whose sequence identification regions form duplexes with the single stranded overhang sequence of the double stranded nucleic acid segment, are hybridized to the one end of the nucleic acid segment to form a ligated molecule.

As used herein, the term "a ligated molecule" refers to a double stranded structure formed after the sequence identification region of an adaptor and the single strand overhang sequence of the nucleic acid segment anneal and at least one pair of the identically oriented strands of the adaptor and the nucleic acid segment are ligated, i.e., are caused to be covalently ligated to one another. In one embodiment of the invention, the ligated molecule is labeled with a detectable label on at least one strand of the molecule and detection occurs following the removal of an unligated labeled adaptor.

As used herein, the term "hybridization" refers to annealing of a nucleic acid sequence to its complement. Hybridization can occur in the presence of a non-annealing region or a nucleotide analog. In one embodiment of the invention, hybridization can also entail ligation. In another embodiment of the invention, hybridization precedes ligation. The term "ligation," as used herein, refers to a ligation of two molecules using conventional procedures known in the art. Ligation can be accomplished either enzymatically or chemically. Chemical ligation methods are well known in the art, e.g., Ferris et al., *Nucleotides & Nucleotides*, 8:407414 (1989); Shabarova et al., *Nucleic Acid Res.* 19:4247–4251 (1991). Preferably, however, ligation is carried out enzymatically using a ligase in a standard protocol. Many ligases are known and are suitable for the use in the present invention, e.g., Lehman, Science 186:790–797 (1974); Boyer, ed., The Enzymes Vol. 15B (Academic Press, New York, 1982). Preferred ligases include nucleic acid ligases, e.g., T4 DNA ligase, T7 DNA ligase, *E. coli* DNA ligase, Taq ligase, Pfu ligase and Tth ligase. Protocols for their use are well known, e.g., Sambrook et al. Molecular Cloning: A Laboratory Manual, 2nd Edition (cold Spring Harbor Laboratory, New York, 1989); Barany, PCR Methods and Applications 1:5–16 (1991). Generally, ligases are require that a 5' phosphate group be present for ligation to the 3' hydroxyl of an abutting strand. This is conveniently provided for at least one strand of the nucleic acid segment by selecting a restriction endonuclease which leaves a 5' phosphate, e.g., a FokI restriction endonuclease. For example, $T_4$ DNA ligase is highly specific in its ability to ligate the 3' end of one oligonucleotide to the phosphorylated 5' end of another oligonucleotide using a DNA template, because a mismatch between the oligonucleotide substrates at the ligation junction greatly reduces the ligation efficiency (Alves A M, F J Carr, *Nucleic Acids Res* 1988; 16:8723, Wu D Y, R B Wallace *Gene* 1989; 76:245–254, Somers VAMC, PTM, Moekerk, J J Murtagh, Jr., and FBJM Thunnissen, *Nucleic Acids Research* 1994; 22:4840–4841, and Samiotaki M, M Kwiatkowski, J Parik and U Landegren, *Genomics* 1994; 20:238–242). This permits highly selective ligation of an oligonucleotide whose end nucleotide is complementary to the template at the ligation junction, allowing template-directed DNA ligation to discriminate between single nucleotides in a designated position of the DNA template. This forms the basis for point mutation discrimination by the ligase chain reaction using either $T_4$ DNA ligase (Wu D Y, R B Wallace, *Genomics* 1989; 4:560–569) or a heat-stable DNA ligase (Barany F. Proc Natl Acad Sci U.S.A. 1991; 88:189–193). *E. coli* DNA ligase can also discriminate between mismatches at a ligation junction (Kato K, *Nucleic Acids Research* 1996; 24:394–395), and other DNA ligases can be anticipated to share this characteristic. The ligase chain reaction, and related earlier methods for nucleotide discrimination using a DNA ligase, detect point mutations at a single position. Each position assessed requires a unique set of annealing oligonucleotides, so that a method based solely on DNA ligation steps can only provide very limited sequence information.

In another embodiment of the invention, template-directed polymerization is used instead of template-directed ligation described above. For example, double stranded molecule having a single stranded overhang sequence generated following FokI digestion can be sequenced by template-directed polymerization in the presence of four deoxynucleotide terminators (e.g. ddNTPs), each tagged with a distinct fluorescent label. Following polymerization and washing, which removes unincorporated terminators, identification of the incorporated terminator can be accomplished by fluorometry, revealing the sequence of nucleotide n in the nucleic acid segment.

After adaptor ligation, an enzyme recognizing the adaptor via the enzyme recognition domain digests the ligated molecule at the site one or more nucleotides from a ligation site along the nucleic acid segment leaving a double stranded molecule having a single strand overhang sequence corresponding to the cut cite capable of participating in the next cycle of legation and digestion.

As used herein, the term "amplify" refers to an in vitro method which can be used to generate multiple copies of a nucleic acid, e.g., a DNA duplex or single-stranded DNA molecule, its complement, or both. Amplification techniques, therefore, include both cloning techniques, as well as PCR based amplification techniques. Preferably, the nucleic acid amplification is linear or exponential, e.g., PCR amplification or strand displacement amplification. These techniques are well known to those of skill in the art. Amplification products are compositions which include a greater number of properly ligated molecules than the number of original nucleic acid segments.

The term "primer" refers to a linear oligonucleotide which specifically anneals to a unique polynucleotide sequence and allows for amplification of that unique polynucleotide sequence. In one embodiment of the invention, the primer specifically anneals to the unique sequence in a cycle identification tag and allows for amplification of a ligated molecule. The primer is of a length which allows it to perform its intended function. Examples of lengths include: from about 8 to about 60 nucleotides in length; from about 8 to about 30 or 40 nucleotides in length; and from about 8 to about 15 or 20 nucleotides in length. In one embodiment of the invention, a primer is said to encode a restriction endonuclease recognition domain if it contains a portion of that recognition domain, when the primer undergoes primer extension to generate a complete strand of that recognition domain.

A strategy can be implemented to remove one of the amplifying primers, and its complement, from each product of amplification, e.g., PCR amplification, thus, preventing the sequencing of DNA encoded by this primer.

Selective removal of primer encoded sequence from a PCR product can be accomplished by restriction endonuclease digestion, without cutting internal recognition domains, using the method of Padgett and Sorge (Padgett K A, J A Sorge, *Gene* 1996; 168:31–35), as described herein. Alternatively, a primer can encode the recognition domain for a restriction endonuclease that requires a methylated nucleotide for cleavage, and recognizes a hemi-methylated recognition domain (see Example 4). Using this strategy, only the primer directed end is cut by the restriction endonuclease because only the primer encoded recognition domain is methylated. Therefore, this strategy does not require substitution of a free methylated nucleotide for its normal counterpart in the PCR mixture, or the recognition domain to contain less that all four nucleotides in a given strand, distinguishing it from the method of Padgett and Sorge.

Technology for removing primer encoded sequence from PCR products can also be used to facilitate the generation of initial nucleic acid segments from clone libraries. For example, the restriction endonuclease recognition domain can be incorporated into the vector adjacent to or within several basepairs of each vector insert, as already described so that following PCR amplification, restriction endonuclease digestion is used to remove primer encoded sequence, prior to ligation of initial adaptors (containing offset recognition domains for the class-IIS restriction endonuclease recognition domain used for sequencing). This will facilitate sequencing of clone libraries because sequencing cycles will not be wasted sequencing the removed primer encoded end of PCR amplified vector inserts. Once a class-IIS recognition domain is discovered that requires a methylated nucleotide and recognizes a hemi-methylated recognition domain, the strategy of using a methylated primer to hemi-methylate the recognition domain in only that primer encoded end of a PCR product will be the predominant method for removing an entire primer sequence from PCR products in those applications for which current class-IIS restriction endonucleases are used, including for the generation of site-directed mutants and recombinant constructs. (Beck R, H Burtscher, *Nucleic Acids Research* 1994; 22:886–887; Stemmer W P C, S K Morris, B S Wilson, *BioTechniques* 1993; 14:256–265; Stemmer WPC, S K Morris, C R Kautzer, B S Wilson, *Gene* 1993; 123:1–7; Tomic M, I Sunjevaric, E S Savtchenko, M Blumenberg, *Nucleic Acids Research* 1990; 18:1656.)

Removal of the amplifying primer can also be accomplished by incorporating a dUTP at the 3' end of this amplifying primer. dUTP is a nucleotide analog that is readily available and can be incorporated into a primer sequence at or near its 3' end during oligonucleotide synthesis. dUPT can prime from the extreme 3' end of a primer even when mismatched (Kwok S, S-Y Chang, J J Sninsky A Wang, *PCR Methods and Applications* 1994; 3:S39–S47). Uracil DNA Glycosylase is used to cleave the N-glycosylic bond between the deoxyribose moiety and uracil, resulting in an abasic site (Varshney U, T Hutcheon, J H van de Sande, *J Biol Chem* 1988; 263:7776–7784). Subsequent heating hydrolyzes the DNA strand at this site, generating a phosphorylated 5' end at the nucleotide located immediately 3' to the dUMP in the original primer, and this phosphorylated 5' end can undergo DNA ligation (Day PJR, M R Walker, *Nucleic Acids Res* 1991; 19:6959, Liu H S, H C Tzeng, Y J Liang, and CC Chen, *Nucleic Acids Res* 1994; 22:4016–4017). Heating to hydrolyze the primer at the abasic site also removes nucleotides located 5' to the dUMP in the original primer, resulting in a 5' phosphorylated end with a 3' overhang sequence.

An alternative method for removing the primer uses a primer with a 3' terminal ribose residue. A 3' terminal ribose residue is incorporated into the primer using the RNA residue as the solid support during standard phosphoramidite synthesis, and the 3' terminal ribose does not interfere with PCR amplification (Walder R Y, J R Hayes, J A Walder, *Nucleic Acids Res* 1993; 21:4339–4343, Silveira M H, and L E Orgel, *Nucleic Acids Res* 1995; 23:1083–1084). Following PCR amplification, a ribose linkage is created in the PCR product that can be readily cleaved by alkaline treatment or by digestion with RNase A for 3'-terminal ribose residues that are C or U. Cleavage of the ribose linkage results in a 3' overhang sequence.

Using either method for primer removal, generation of a blunt end suitable for ligation to an adaptor can then be accomplished by incubating with a single-strand specific exonuclease (e.g. Mung bean exonuclease), or with a DNA polymerase with a 3' exonuclease activity (e.g. $T_4$ DNA Polymerase) in the presence of the four dNTPs (Stoker A W, *Nucleic Acids Res* 1990; 18:4290), permitting the removal of a primer sequence and its complement from PCR products prior to sequencing. Following adaptor ligation, a subsequent PCR step can use the ligated adaptor to generate a primer annealing site, so that only successfully ligated products are regenerated. Using any of the above strategies, with or without removal of one of the initial primers and its complement, initial template precursors can be generated.

As is described more fully below, in the course of such cycles of ligation and digestion, the first unpaired nucleotide in the overhang sequence of the double stranded nucleic acid segment is identified. For example, this nucleotide can be identified using an adaptor with a detectable label. As used herein, the term "detectable label" refers to a material that can attach to a DNA molecule and generate a signal. The adaptors may be labeled by a variety of means and at variety of locations. The adaptors of the invention can be labeled by methods known in the art, including the direct or indirect attachment of radioactive labels, fluorescent labels, colorimetric labels, chemilluminescent labels and the like, as described in Matthews et al., *Anal. Biochem.*, Vol. 169, pgs. 1–25 (1988); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26:227–259 (1991); and the like. Many more particular methodologies applicable to the invention are disclosed in the following sample of references: Connolly, *Nucleic Acids Research*, Vol. 15, pgs. 3131–3139 (1987); Gibson et al., *Nucleic Acids Research*, Vol. 15, pgs. 6455–6467 (1987); Spoat et al., *Nucleic Acids Research*, Vol. 15, pgs. 4837–4848 (1987); Fung et al., U.S. Pat. No. 4,757,141; Hobbs, Jr. et al., U.S. Pat. No. 5,151, 507; Cruickshank, U.S. Pat. No. 5,091,519; (synthesis of functionalized oligonucleotides for attachment of reporter groups); Jablonski et al., Nucleic Acid Research, 14:6115–6128 (1986) (enzyme-oligonucleotide conjugates); and Urdea et al., U.S. Pat. No. 5,124,246 (branched DNA). Preferably, the adaptors are labeled with one or more fluorescent dyes, e.g., as described in U.S. Pat. No. 5,188,934 and PCT application PCT/US90/05565. In a preferred embodiment of the invention, the adaptor is attached to a solid matrix, such as a magnetic particle, e.g., magnetic streptavidin or magnetic glass particle, polymeric microsphere, filter material, or the like.

FIGS. 1, 2, 3 and 4 illustrate four embodiments of the present invention. FIG. 1 illustrates the use of a class-IIS restriction endonuclease that generates a 5' overhang, and sequences a nucleotide at each interval by template-directed ligation. In FIG. 1, this embodiment is illustrated using the class-IIS restriction endonuclease FokI, and the template precursor has a biotinylated end that allows it to be bound to streptavidin. In Step 1, the template precursor is cleaved with FokI. Fok I has the following recognition domain and cut site:

5'GGATG $(N)_9$

3'CCTAC $(N)_{13}$

FokI generates a four nucleotide long 5' overhang positioned nine nucleotides away from one side of the recognition domain, so that sequencing can be carried out in intervals of nine nucleotides. Fok I digestion cleaves both strands of the double-stranded DNA, generating a DNA template with a 5' overhang sequence. The bound template is washed to remove the cleaved ends. In Step 2 the 5' overhang sequence mediates ligation to one of four adaptors. These adaptors contain the sequence for the recognition domain for FokI and have an adjacent four nucleotide long and phosphorylated 5' overhang consisting of three nucleotides with 4-fold degeneracy and a 5' terminus with one of the four normal nucleotides. Since the four adaptors each have three degenerate nucleotides and four distinct 5' terminal nucleotides, there are 256 distinct sequences. The adaptors shown are double-stranded, because this increases the ligation efficiency, probably due to stacking interactions (Lin S-B, K R Blake, P S Miller, *Biochemistry* 1989; 28:1054–1061). In this embodiment of the method there is one ligation reaction during each sequencing cycle. In each ligation, all four adaptors are present, and each adaptor is tagged with a distinct fluorescent label (e.g. Fama-NHS ester, Rox-NHS ester, Tamra-NHS ester, or Joe-NHS ester; Applied Biosystems Division of Perkin-Elmer, Foster City Calif.); each label identifying the nucleotide at the single-stranded 5' end of the adaptor. Ligation occurs for the adaptor for which the above mentioned 5' nucleotide is complementary to the nucleotide on the 5' end of the DNA template at the ligation junction. Following ligation, and washing to remove the unligated adaptors, identification of the ligated adaptor can be accomplished by fluorometry, revealing the sequence of the DNA template at the ligation junction (Step 3). In step 4, the ligated template from Step 2 undergoes PCR amplification using a biotinylated primer and using a primer that is complementary to a unique portion of the adaptor's ligated lower strand. An alternative approach would sequence via ligation of the adaptor's upper strand. In this approach, the fixed nucleotide in the single strand extension in each adaptor is the fourth nucleotide 3' to the 5' end. The label is preferably in the upper strand, and this label identifies the lower strand's fixed nucleotide in the single strand overhang, with the remaining nucleotides in this single strand being promiscuous nucleotides (degenerate or universal nucleotides). In this embodiment of the invention, one of the primers would be homologous to a unique portion of the adaptor's ligated upper strand.

This unique region, and its corresponding amplification primer, may differ during every sequencing cycle, or during every several sequencing cycles. By using ligated adaptors and corresponding amplifying primers that differ in each cycle, uncut products from Step 1 are not amplified, preventing uncut products from generating background signal in subsequent cycles. The PCR product is bound to streptavidin, and the entire process is repeated, sequencing a nucleotide nine nucleotides within the original nucleic acid segment during each cycle of cutting, template-directed ligation, and amplification of the desired template precursor. During Step 1 of the subsequent cycle digestion with FokI cleaves both strands of the DNA and generates a new 5' overhang sequence with each strand shortened by nine nucleotides when compared to the template at the end of the prior Step 1. (This shortening of the template precursor following each cycle is not shown in FIGS. 1–4).

Additional steps can be taken to increase the efficiency of each step, and may prove necessary in implementing a protocol that does not use amplification to regenerate the template precursor during each cycle. These additional steps include:

1) Treating the template with alkaline phosphatase following restriction endonuclease cutting (Step 1 of FIG. 1). This de-phosphorylates the 5' end of each template, preventing ligation of one template to another.

2) Using adaptors with upper strand 3' ends that are blocked by a 3' phosphate or blocked by a 3' dideoxy nucleotide. This prevents ligation of one adaptor to another during Step 2 of the method of FIG. 1.

3) Incubating with a DNA polymerase and the four ddNPTs following the adaptor ligation step (Step 2 in FIG. 1). This fills in the recessed 3' end of those templates that escaped adaptor ligation, and caps these ends so that they cannot undergo ligation (Atkinson M R, M P Deutscher, A Kornberg, A F Russell, J G Moffatt, *Enzymatic Synthesis of DNA* 1969; 8:4897–4904). This additional step prevents templates that failed to undergo adaptor ligation during a given cycle from undergoing adaptor ligation in subsequent cycles, thus eliminating background signal resulting from incomplete ligation of templates.

4) Retained fluorescent label resulting from incomplete cutting by Fok I can be quenched by photo-bleaching immediately prior to Step 1, or through cleavage of the label by using a labile linkage (Dawson B A, T Herman, J Lough *Journal of Biological Chemistry* 1989; 264:12830–12837, Olejnik J. E Krzymanska-Olejnik, K J Rothschild *Nucleic Acids Research* 1996; 24:361–366) thus decreasing background fluorescent signal from previous cycles.

If the lower strand of the adaptor is ligated, and the upper strand's 3' end is not blocked, non blocked and added later, or is de-blocked (via dephosphorylating a 3' phosphate, Cameron V, O C Uhlenbeck *Biochemistry* 1977; 16:5120–5126 or, for example, by the method described in Metzker M L, Raghavachari R, Richards S, Jacutin S E, Civitello A, Burgess K and R A Gibbs, *Nucleic Acids Res.* 1994;22:4259–4267 and Canard B and R S Sarfati, *Gene* 1994;148:1–6), an intact double-stranded segment can be generated, without nicks, using a DNA polymerase with a 5' exonuclease activity, in a nick translation reaction (Rigby PWJ, M Dieckmann, C Rhodes, P Berg *Mol. Biol.* 1977; 113:237–251). Such nick translation could occur with concurrent hemi-methylation of internal recognition domain for the class-IIS restriction endonuclease using the primer extension strategy of Han and Rutter (Han J, Rutter W J, *Nucleic Acids Res* 1988; 16:11837).

If the upper strand of the adaptor is ligated, an intact double-stranded segment could be generated, without nicks, by using a DNA polymerase to generate the complement to the adaptor's ligated upper strand. This polymerization could occur with concurrent hemi-methylation of the adaptor encoded recognition domain for the class-IIS restriction endonuclease using the polymerase extension in the presence of a methylated nucleotide (when sequencing with a class-IIS restriction endonuclease that recognizes a hemi-methylated recognition domain; also, if the ligated upper-strand's recognition domain sequence were methylated, both strands of the recognition domain would be methylated using this method). If the adaptor were double-stranded, the unligated lower strand of the adaptor could be digested by nick translation using a DNA polymerase with 5' exonuclease activity, or by using a DNA polymerase with strand displacement activity.

Figure 2:
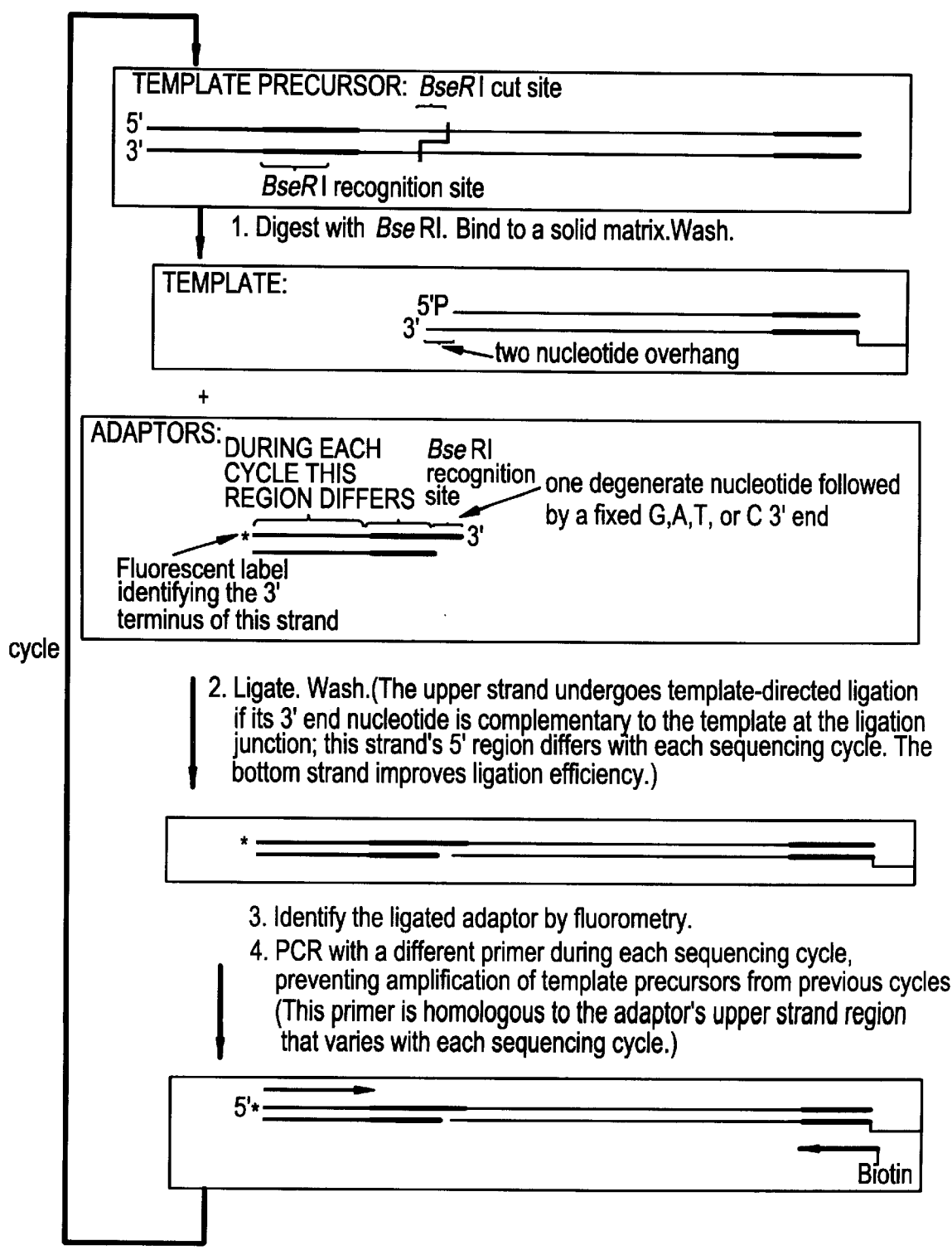
FIG. 2 is a schematic diagram of interval DNA sequencing method using a class-IIS restriction etdonuclease that generates a 3' overhang (BseRI), template-directed ligation to labeled adaptors, and PCR. DNA encoded by oligonucleotides or their PCR generated complements is depicted as thick lines. Following each cycle the template precursor is shortened.

FIG. 2 illustrates a second embodiment of the sequencing method of this invention wherein a class-IIS restriction endonuclease generates a 3' overhang, and sequences a nucleotide at each interval by template-directed ligation. In FIG. 2, this embodiment is illustrated using the class-IIS restriction endonuclease BseRI, and the template precursor has a biotinylated end that allows it to be bound to streptavidin. In Step 1, the template precursor is cleaved with BseRI. BseRI has the following recognition domain and cut site:

5'GAGGAG (N)$_{10}$

3'CTCCTC (N)$_8$

BseRI generates a two nucleotide long 3' overhang positioned eight nucleotides away from one side of the recognition domain, so that sequencing can be carried out in intervals of eight nucleotides. BseRI digestion cleaves both strands of the double-stranded DNA, generating a DNA template with a 3' overhang sequence. The bound template is washed to remove the cleaved ends. In Step 2 the DNA template (3' overhang sequence) undergoes ligation in the presence of four adaptors. These adaptors contain the sequence for the recognition domain for BseRI and have an adjacent two nucleotide long 3' overhang consisting of one nucleotide with 4-fold degeneracy and a 3' terminus with one of the four normal nucleotides. Since the four adaptors each have one degenerate nucleotide and four distinct 3' terminal nucleotides, there are 16 distinct sequences. The adaptors are double-stranded, because this increases the ligation efficiency. There is one ligation reaction during each sequencing cycle. In each ligation, all four adaptors are present, and each adaptor is tagged with a distinct fluorescent label; each label identifies the single-stranded nucleotide at the single-stranded 3' end of the adaptor. Ligation of the upper strand of the adaptor occurs if the above mentioned 3' nucleotide is complementary to the nucleotide on the 3' end of the DNA template at the ligation junction. Following ligation and washing to remove the unligated adaptors, identification of the ligated adaptor can be accomplished by fluorometry, revealing the sequence of the DNA template at the ligation junction (Step 3). In step 4, the ligated template from Step 2 undergoes PCR amplification using a biotinylated primer and using a primer that is homologous to a unique portion of the adaptor's ligated upper strand. If the lower strand underwent the ligation reaction that sequenced the DNA, by using an upper strand that had its fixed nucleotide in its 3' single stranded portion of the adaptor immediately adjacent to the double-stranded portion of the adaptor, the non-biotinylated primer would be complementary to a unique portion in the ligated adaptor's lower strand. This unique region, and its corresponding amplification primer, may differ during every sequencing cycle, or during every several sequencing cycles, preventing uncut products from a prior cycle from generating background signal in subsequent cycles. The PCR product is bound to streptavidin, and the entire process is repeated, sequencing a nucleotide eight nucleotides further within the original nucleic acid segment during each cycle of cutting, template-directed ligation, and in vitro amplification of the desired template precursor. During Step 1 of each subsequent cycle, digestion with BseRI cleaves both strands of the DNA and generates a new 3' overhang sequence with each strand shortened by eight nucleotides when compared to the template at the end of the prior Step 1.

Another step can be taken to prevent templates that do not undergo ligation during a given cycle from undergoing ligation in a subsequent cycle. Following adaptor ligation (Step 2 of FIG. 2) incubation with alkaline phosphatase will dephosphorylate the 5' end of those templates that did not undergo ligation to an adaptor, preventing these templates from undergoing adaptor ligation in subsequent cycles. If amplification (Step 4 of FIG. 2) is not used, following ligation of the adaptor's upper strand (Step 2 of FIG. 2), the lower strand of the DNA being sequenced can prime template-directed polymerase extension using a DNA polymerase with a 3' exonuclease activity, in the presence of the four dNTPs recognizing that the DNA polymerase preferably has a 5' exonuclease activity or a strand displacement activity if the adaptor has a lower strand. This will re-synthesize the lower strand of the attached adaptor, eliminating the nick and any mismatches while generating a template precursor. Also, those templates which did not undergo adaptor ligation will be rendered blunt ended by the 3' exonuclease activity of the DNA polymerase preventing adaptor ligation in subsequent cycles. When using a restriction endonuclease that generates a 3' overhang, a terminal transferase can be used to add a single dideoxy nucleotide to the end of the template. This terminal nucleotide can act as a barb in a hook to help hold the adaptor in place, as each adaptor can share a nucleotide complementary to the dideoxy nucleotide in each adaptor's annealing strand, so that this will increase the efficiency of adaptor ligation. In this case, sequencing occurs in an interval that is one nucleotide shorter than the distance between the recognition domain and the cleavage domain.

When a DNA polymerase is used to generate the complement to the adaptor's ligated upper strand, this polymerization may be performed with concurrent hemi-methylation of the adaptor encoded recognition domain for the class-IIS endonuclease using the polymerase extension in the presence of a methylated nucleotide (when sequencing with a class-IIS restriction endonuclease that recognizes a hemi-methylated recognition domain; also, if the ligated upper-strand's recognition domain sequence were methylated, both strands of the recognition domain would be methylated using this method). If the adaptor were double-stranded, the unligated lower strand of the adaptor could be digested by nick translation using a DNA polymerase with 5' exonuclease activity, or by using a DNA polymerase with strand displacement activity.

If the lower strand of the adaptor is ligated, an intact double-stranded segment could be generated, without nicks, by using a DNA polymerase with a 5' exonuclease activity, in a nick translation reaction (Rigby, PWJ, M Dieckmann, C Rhodes, P Berg *Mol. Biol.* 1977; 113:237–251) using the upper strand of the adaptor as a primer. Such nick translation could occur with concurrent hemi-methylation of internal recognition domain for the class-IIS restriction endonuclease using the primer extension strategy of Han and Rutter (Han J, Rutter W J *Nucleic Acids Res* 1988; 16:11837).

Figure 3:
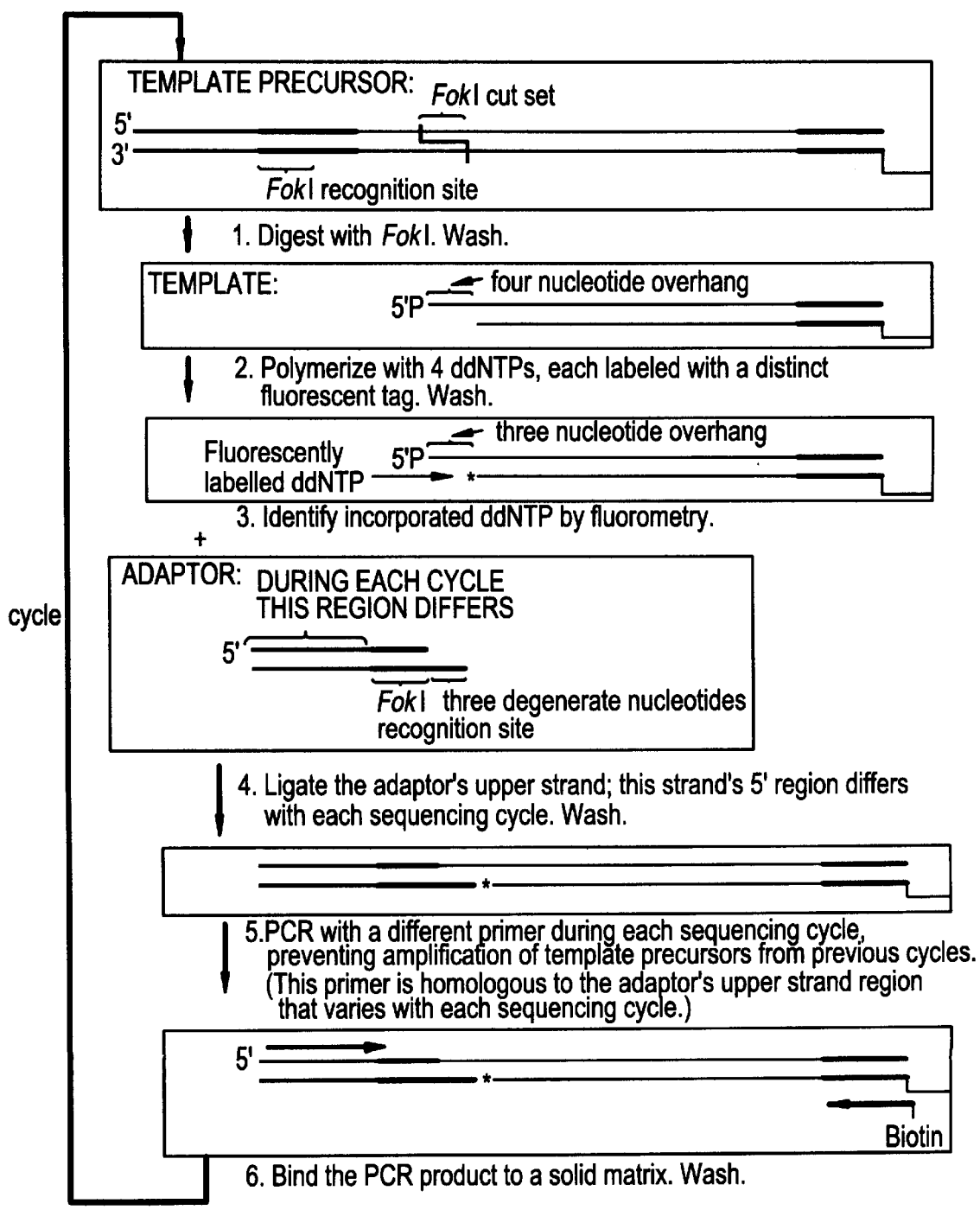
FIG. 3 is a schematic diagram of interval DNA sequencing method using a class-IIS restriction endonuclease that generates a 5' overhang (FokI), template-directed polymerase extension with labeled terminators, template-directed ligation, and PCR DNA encoded by oligonucleotides or their PCR generated complements is depicted as thick lines. Following each cycle the template precursor is shortened.

FIG. 3 shares with FIG. 1 the use of a class-IIS restriction endonuclease that generates a 5' overhang, but sequences a nucleotide at each interval by template-directed polymerization instead of template-directed ligation. In Step 2 of FIG. 3, the DNA template generated following FokI digestion is sequenced by template-directed polymerization in the presence of four deoxynucleotide terminators (e.g. ddNTPs), each tagged with a distinct fluorescent label. Following polymerization and washing, which removes unincorporated terminators, identification of the incorporated terminator can be accomplished by fluorometry, revealing the sequence of one nucleotide in the DNA template, as shown in Step 3. Step 4 illustrates the ligation of an adaptor containing the sequence for the recognition domain for FokI and an adjacent three nucleotide long 5' overhang consisting of three nucleotides with 4-fold degeneracy. The ligation illustrated in FIG. 3 is template-directed but is not used to discriminate between nucleotides at the ligation junction. Since the single adaptor has three degenerate nucleotides, there are 64 distinct sequences. The adaptors shown are double-stranded, as this increases the ligation efficiency. The amplification shown in Step 5 of FIG. 3 corresponds to Step 4 of FIG. 1, except that the amplifying primer is homologous to the ligated strand of the adaptor, which is the upper strand in FIG. 3.

Since the upper strand of the adaptor undergoes ligation, an intact double-stranded segment could be generated, without nicks, by using a DNA polymerase to generate the complement to the adaptor's ligated upper strand. The lower strand of the DNA segment being sequenced can de-blocked (via dephosphorylating a 3' phosphate, or by the method described in Metzker M L, Raghavachari R, Richards S, Jacutin S E, Civitello A, Burgess K and R A Gibbs, *Nucleic Acids Res.* 1994;22:4259–4267 and Canard B and R S Sarfati, *Gene* 1994;148:1–6), allowing it to act as a primer. This polymerization could occur with concurrent hemi-methylation of the adaptor encoded recognition domain for the class-IIS endonuclease using the polymerase extension in the presence of a methylated nucleotide (when sequencing with a class-IIS restriction endonuclease that recognizes a hemi-methylated recognition domain; also, if the ligated upper-strand's recognition domain sequence were methylated, both strands of the recognition domain would be methylated using this method). The double-stranded segment, without nicks, could be generated by a nick translation reaction using a primer complementary to the adaptor's ligated upper strand, and a DNA polymerase with 5' exonuclease activity. This would also eliminate incorporated label, and such nick translation could occur with concurrent hemi-methylation of internal recognition domain for the class-IIS restriction endonuclease using the primer extension strategy of Han and Rutter Han J. Rutter W J *Nucleic Acids Res* 1988; 16:11837).

In the strategy illustrated in FIG. 3, if the class II-S restriction endonuclease generates a single nucleotide 5' end extension, template-directed polymerization will generate a blunt end, so that adaptor ligation is blunt ended, as opposed to the template-directed ligation illustrated in FIG. 3. Furthermore, if a class-IIS restriction endonuclease is discovered that generates a blunt end, or a blunt end is generated using a single strand exonuclease, a nucleotide at this end could be sequenced by template-directed polymerization through a nucleotide exchange reaction, in which the 3' exonuclease activity of DNA polymerase is used to generate a recessed 3' end that can undergo template-directed polymerization, incorporating a labeled nucleotide and once again generating a blunt end that would undergo ligation to the adaptor (Atkinson M R, M P Deutscher, A Kornberg, A F Russell, J G Moffatt *Enzymatic Synthesis of DNA* 1969; 8:4897–4904, Englund P T *Journal of Biological Chemistry* 1971; 246:3269–3276). In this case, the template is formed fleetingly, through the 3' exonuclease activity of a DNA polymerase during the exchange reaction that constitutes the DNA sequencing step. If the incorporated labeled terminator inhibits adaptor ligation, only a fraction of a given terminator needs to carry a label, and only a fraction of a given template needs to undergo labeling, because only a fraction of a template must undergo adaptor ligation to allow regeneration of the desired template precursors by DNA amplification in vitro. This illustrates how product regeneration allows separation of the template generation and template sequencing elements of this method without physical separation of these elements into separate aliquots.

Figure 4:
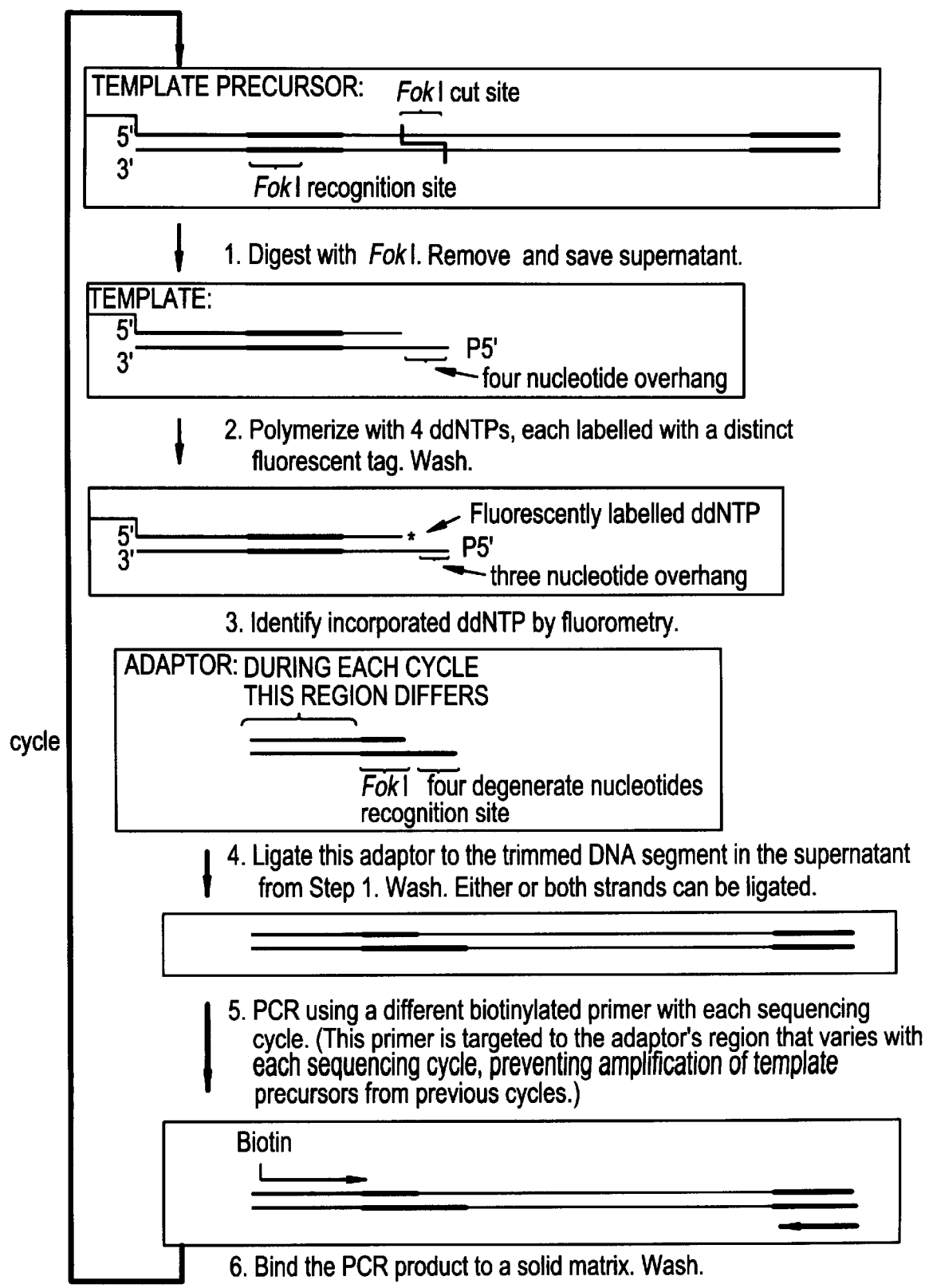
FIG. 4 is a schematic diagram of interval DNA sequencing method using a class-IIS restriction endonuclease that generates a 5' overhang (FokI), template-directed polymerase extension with labeled terminators, template-directed ligation, and PCR. The template complementary to the template in FIG. 3 is attached to a solid phase and is sequenced. DNA encoded by oligonucleotides or their PCR generated complements is depicted as thick lines. Following each cycle the template precursor is shortened.

FIG. 4 illustrates a variation of the method of FIG. 3 in which the overhang appended to the adaptor-encoded sequenc is attached to a solid phase. In this variation, the PCR primer that varies between cycles carries the biotin moiety. Following FokI cutting, the end encoded by the adaptor is attached to the solid matrix, and a nucleotide in this end is sequenced by template-directed polymerization. In addition, this end could be sequenced by template-directed ligation, in which case the class-IIS restriction endonuclease could generate a 5' overhang or a 3' overhang. Another variation that could be carried out would be to combine sequencing by template-directed polymerization with sequencing by template-directed ligation. For example, if the adaptor undergoing template-directed ligation in Step 4 of FIG. 4 were a sequencing adaptor, as shown in FIG. 1, sequencing could be accomplished by template-directed ligation and template-directed polymerization during each cycle using the same template precursor. Also, it is clear that the process of sequencing each template can be separated from the process of generating each template, so that a FokI generated four nucleotide overhang could be sequenced, for example, by template-directed ligation and in a separation reaction by fill-in with labeled ddNTPs.

Variants of protocols shown in FIGS. 1–4 not requiring the exponential amplification step (Step 4 of FIGS. 1 and 2 and Step 5 of FIGS. 3 and 4) can be developed using steps that optimize completion of each step and that "cap" incomplete reactions, as described previously in conjunction with striding. For example MmeI has a recognition domain that is separated from its cleavage domain by 18 bp. Therefore, one could sequence over a span of 90 nucleotides over five iterative cycles, as opposed to only 5 nucleotides when using a method that sequences consecutive nucleotides. Other measures that may increase the number of sequencing cycles that can be carried out without using exponential in vitro amplification, include:

1) Modification of a restriction endonuclease recognition domain by use of a base analog to improve binding to the restriction enzyme, so that a modified double-stranded oligonucleotide binds to its restriction endonuclease more effectively than the naturally occurring recognition domain (Lesser D R, M R Kurpiewski, T Waters, B A Connolly, and L Jen-Jacobson, *Natl. Acad. Sci. USA* 1993; 90:7548–7552). Using a ligated adaptor with a modified class-IIS recognition domain may improve restriction endonuclease binding and cutting efficiency. For example, a hybrid restriction endonuclease could be generated in which a protein that recognizes a certain DNA sequence or moiety is attached to the cleaving domain of a class-IIS restriction endonuclease, generating a new specificity with a defined distance between a cleavage domain and a recognition domain (Kim Y-G, J Cha, S Chandrasegaran, *Proc. Natl. Acad. Sci. USA*. 1996; 93: 1156–1160).

2) Ligating adaptors that are covalently attached to a class-IIS restriction endonuclease. A variety of enzymes have been covalently attached to oligonucleotides (Jablonski E, E W Moomaw, R H Tullis, J L Rith, *Nucleic Acids Res* 1986; 14:6115–6128, Li P, P P Medon, D C Skingler, J A Lanser, R H Symons, *Nucleic Acids Res* 1987; 15:5275–5287, Ghosh S S, P M Kao, D Y Kwoh, *Anal Biochem* 1989;78;178:43–51). Use of a double-stranded recognition domain with the class-IIS restriction endonuclease attached to it could be used to target cutting to the cleavage domain adjacent to the ligated adaptor's recognition domain, so long as buffer conditions during the prior ligation do not permit cutting. Since the restriction endonuclease would only be positioned immediately adjacent to the desired recognition site, digestion would not be mediated by internal recognition domains, so that methylation of internal recognition domains would not be necessary.

3) Using a class-IIS restriction endonuclease that requires a methylated recognition domain, and will recognize a hemi-methylated recognition domain. In this case, the recognition domain can be hemi-methylated during adaptor ligation using an adaptor strand that contains a methylated strand of this domain, so that only this recognition domain would be recognized. A class-IIS restriction endonuclease that requires a methylated recognition domain could be used in this method and would be advantageous, as it would obviate the need to block internal recognition domains for this class-IIS restriction endonuclease.

Restriction endonucleases and DNA ligases have been used in this invention, but different enzymes or reactive chemicals could be used to generate the templates described in this invention. Mutated enzymes that carry out the same role can substitute for their naturally occurring counterparts (Kim J J, K T Min, M H Kim, S J Augh, B-D Dim, D-S Lee *Gene* 1996; 171:129–130). Furthermore, various entities can substitute for DNA ligase and restriction endonucleases. Template-directed ligation has carried out through chemical condensation (Gryaznov S M, R Schultz, S K Chaturvedi, R L Letsinger, *Nucleic Acids Research* 1994 22:2366–2369, Dolinnaya N G, M Blumenfeld, I N Merenkova, T S Oretskaya, N F Krynetskaya, M G Ivanovskaya, M Vasseur and Z A Shabarova, *Nucleic Acids Research* 1993; 21:5403–5407, Luebke K J and P B Dervan, *Nucleic Acids Research* 1992; 20:3005–3009), and site-specific cleavage of DNA has been accomplished using oligonucleotides linked to reactive chemicals or non-specific nucleases (Lin S-B, K R Blake, P S Miller *Biochemistry* 1989;28:1054–1061, Strobel, S A, L A Doucette-Stamm, L Riba, D E Housman, P B Dervan, *Science* 1991; 254:1639–1642, Francois J-C, T Saison-Behmoaras, C Barbier, M Chassignol, N T Thuong, C Helene, *Proc. Natl. Acad. Sci. USA* 1989; 86:9702–9706, Pei D, D R Corey, P G Schultz, *Proc. Natl. Acad. Sci. USA* 1990; 87:9858–9862). Non-protein enzymes have also been used to manipulate DNA, as ribozymes have mediated both the cleavage and ligation of DNA (Tsang J, G F Joyce, *Biochemistry* 1994; 19:5966–5973, Cuenoud B, J W Szostak, *Nature* 1995; 375:611–614).

Nucleotide analogs have been used in a variety of functions, and template-directed ligation could be mediated by adaptors with single-stranded ends containing universal nucleotides or discriminatory nucleotide analogues (Loakes D, D M Brown, *Nucleic Acids Research* 1994; 22:4039–4043, Nichols R, P C Andrews, P Zhang, D E Bergstrom, *Nature* 1994; 369:492–493). In addition, modified nucleotides other than methylated nucleotides have been found that block recognition by restriction endonucleases, and can be incorporated through primer-directed DNA synthesis (Huang L-H, C M Farnet, K C Ehrlich, M Ehrlich, *Nucleic Acids Research* 1982; 10:1579–1591, Seela F, W Herdering, A Kehne *Helvetica Chimica Acta* 1987; 70:1649–1660, and Seela F, A Roling, *Nucleosides and Nucleotides* 1991; 10:715–717).

Technology now exists for the generation of a thousand distinct DNA segments at one time using the polymerase chain reaction (PCR), thus allowing the concurrent generation of a thousand DNA template precursors. Development of technology for template precursor generation is facilitated by present methods for the concurrent generation of multiple oligonucleotides, as oligonucleotides serve as primers for template precursor generation through DNA amplification in vitro (Caviana Pease A, Solas D, Sullivan E J, Cronin M T, Holmes C P, Fodor SPA, *Proc Natl Acad Sci USA* 1994; 91:5022–5026). Micro-chip based technology will allow the amplification of over 10,000 distinct DNA segments, each containing several hundred base pairs of DNA (Shoffner M A, J Cheng, G E Hvichia, L J Kricka, P Wilding, *Nucleic Acids Research* 1996; 24:375–379, and J Cheng, Shoffner M A, G E Hvichia, L J Kricka, P Wilding, *Nucleic Acids Research* 1996; 24:380–385). This will allow a large portion of the human genome of an individual to be sorted on a biochip. Rapid technical progress in DNA sample generation creates a need for technology that can rapidly and accurately sequence arrayed samples of DNA in parallel. This invention addresses the need for technology that can sequence thousands of distinct DNA samples in parallel.

Technology for generating double-stranded template-precursors via PCR, and for the fluorometric assessment of thousands of locations on a chip, will allow the sequencing of several thousand PCR products simultaneously using this invention, allowing large amounts of DNA to be sequenced using repetitive incubations in simple reagents. The template precursors can be bound to a silicon chip or contained in a matrix of chambers, so that cycles of adaptor ligation, template-directed DNA polymerization for amplification or sequencing, and cutting can be carried out on numerous templates in parallel.

Technology that has been developed for the simultaneous assessment of thousands of locations on a chip will facilitate the simultaneous sequencing of these templates. For example, a microchip has been designed for the quantitative detection of DNA labeled with fluorescent, chemiluminescent or radioactive reporter groups (Eggers M, M Hogan, R K Reich, J Lamture, D Ehrlich, M Hollis, B Kosicki, T Powdrill, K Beattie, S Smith, R Varma, R Gangadharan, A Mallik, B Burke and D Wallace, *BioTechniques* 1994; 17:516–524). This microchip consists of a charged coupled device (CCD) detector that quantitatively detects and images the distribution of labeled DNA near spatially addressable pixels. DNA has been deposited onto a silicon wafer with a micro-jet using DNA with an amine modified 5' end, which is linked to the SiO2 surface by secondary amine formation. This immobilized DNA is on an SiO2 wafer overlying the pixels of the charged coupled device. A prototype 420×420 pixel device has been developed that can analyze 176,400 samples in parallel, enabling the detection of thousands of label incorporation events on a square centimeter chip (Eggers M, M Hogan, R K Reich, J Lamture, D Ehrlich, M Hollis, B Kosicki, T Powdrill, K Beattie, S Smith, R Varma, R Gangadharan, A Mallik, B Burke and D Wallace, *BioTechniques* 1994; 17:516–524).

Technology that will further enhance the utility of the present invention include hybridization based approaches for sorting genomic DNA (as opposed to sequencing by hybridization) into unique restriction fragments, which can then be amplified at their addresses using a single set of PCR primers (Chetverin A B, F R Kramer, *BioTechnology* 1994; 12:1093–1099). In the future, it will be possible to apply the present invention to the sequencing of large portions of genomes for which there is no prior sequence information without cloning in vivo (e.g., in *E. coli*). New innovative hybridization based strategies have been proposed that use oligonucleotide arrays to sort restriction endonuclease generated fragments on the basis of their unique sequences. In one strategy, genomic DNA undergoes complete restriction endonuclease digestion. This is followed by ligation of the DNA ends to adaptors. These restriction fragments are sorted on a hybridization array of oligonucleotides through annealing to the adaptor sequence as well to unique adjacent sequences in the DNA fragments. This is followed by a ligation step that requires perfect complementarity of the unique sequence adjacent to the adaptor, resulting in sorting of the restriction fragments into unique addresses on the biochip. An additional step repeats this strategy using the opposite end of each fragment. These sorted fragments can then be PCR amplified in situ using a single set of primers that anneal to the adaptor sequences (Chetverin A B, F R Kramer, *BioTechnology* 1994; 12:1093–1099). Integrating this hybridization-based technology into the present method will allow the sequencing of genomes using a single set of PCR primers without prior sequence information.

An area of technology development that can also be useful to the application of the proposed method is oligonucleotide synthesis from the 5' to 3' direction (Coassin P J, J B Rampal, R S Matson *International Workshop on Sequencing by Hybridization* (Woodlands, Tex.) 1993; Report 8). This will allow amplifying primers to be manufactured on a chip. These bound primers could be used to amplify PCR products, as it has recently been confirmed that a primer can mediate PCR amplification while bound to a solid immobile matrix (Kohsaka H, D A Carson, *Journal of Clinical Laboratory Analysis* 1994; 8:452–455).

Kits

A variety of kits are provided for carrying out different embodiments of the invention. Generally, kits of the invention include adaptors tailored for the enzyme, e.g., a class IIS restriction endonuclease, and the detection scheme of the particular embodiment. Kits further include the enzyme reagents, the ligation reagents, PCR amplification reagents, and instructions for practicing the particular embodiment of the invention. In embodiments employing natural protein endonucleases and ligases, ligase buffers and endonuclease buffers may be included. In some cases, these buffers may be identical. Such kits may also include a methylase and its reaction buffer. Preferably, kits also include a solid phase support, e.g. magnetic beads, for anchoring target DNA segments. In one preferred kit, labeled ddNTP's are provided. In another preferred kit, fluorescently labeled probes are provided such that probes corresponding to different terminal nucleotides of probe or the target polynucleotide carry distinct spectrally resolvable fluorescent dyes. As used herein, "spectrally resolvable" means that the dyes may be distinguished on basis of their spectral characteristics, particularly fluorescence emission wavelength, under conditions of operation. Thus, the identity of the one or more terminal nucleotides would be correlated to a distinct color, or perhaps ratio of intensifies at different wavelengths. More preferably, four such probes are provided that allow a one-to-one correspondence between each of four spectrally resolvable fluorescent dyes and the four possible terminal nucleotides on a target DNA segment. Sets of spectrally resolvable dyes are disclosed in U.S. Pat. Nos. 4,855,225 and 5,188,934; International application PCT/US90/05565; and Lee et al., *Nucleic Acids Research* 20:2471–2483 (1992).

Automation of Iterative and Regenerative DNA Sequencing

The foregoing sequencing steps, being iterative, may be automated and applied in parallel to an arbitrary number of separate samples. Such automation permits the sequencing method to generate a large amount of sequence information, and this information is further enhanced by the subinterval or adjacency order existing between the products of successive steps, as well as in a multiplex scheme, the immobilized spatial locations in which sequencing occurs.

Figure 8:
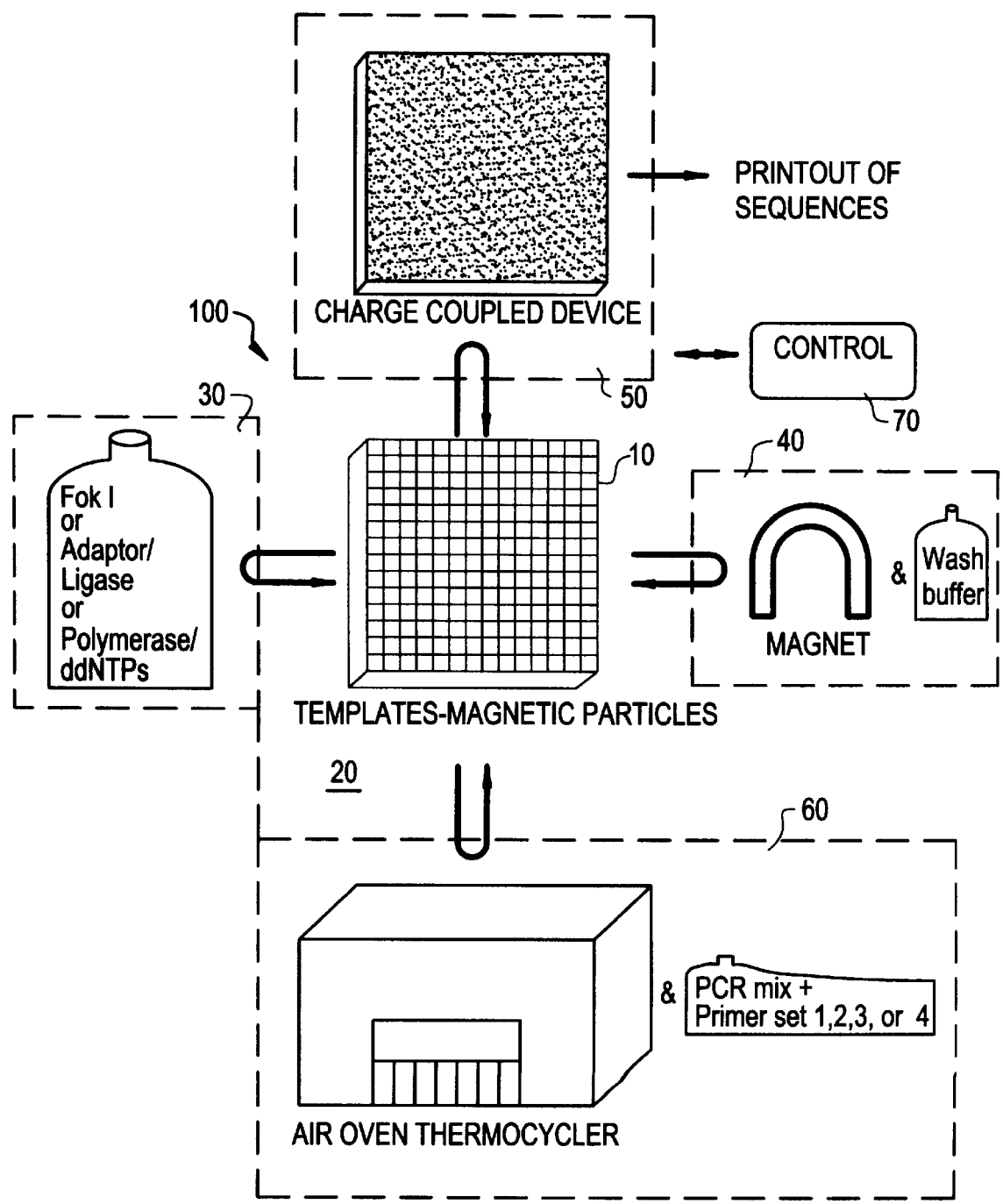
FIG. 8 is a schematic representation of an automated instrument for automated sequencing of multiple DNA segments.

FIG. 8 shows a schematic outline of the overall architecture of a system 100 for automating sequencing according to the present invention, which is preferably implemented by a processing apparatus 20 which operates on support arrays 10 such as microtiter plates or specially fabricated chip arrays that consist of an array of wells, chambers or surface immobilization positions each capable of holding a DNA sample at a localized site. Device 20 performs four general types of operations in parallel on the DNA segments in the support array 10, and these are shown schematically as separate classes of processes arrayed in stations or functional groupings 30, 40, 50, 60 around the central device 20.

As shown, the four basic processes involve the addition of reagents 30, washing, separating or preparation steps 40, reading the labeled segments at 50, or incubation and amplification steps at 60. These are schematically illustrated as four separate workstations through which the support array 10 is shuttled or moved, but are preferably implemented with varying degrees of integration into the basic array handler 20. Thus, for example, the array 10 may stay in position on a stage to which the necessary conduits or manifolds are attached for addition of the reagents and washing of the samples, and which may be heated or cooled in cycles to incubate and amplify all materials on the support at once. Similarly, for reading, a charge couple device may be carried with appropriate optics by the device 20 to read the labeled material in each sample well between successive steps, or may be integrated into a cover plate or the structure of the sample support. In either case, each of these subunits or accessory portions of the system operates under control of a common controller 80 which coordinates the movement, heating, provision of reagents and reading of the various steps so that the readout of nucleotide labels by the reading section 50 is stored and recorded for the DNA samples at each location on the array 10.

As noted above, each of the DNA segments which are to be analyzed, which may, for example, be PCR products or vector inserts, is immobilized so that it resides at a unique address on the chip or support 10, and several hundred to thousands of DNA segments are distributed on the chip. They simultaneously undergo a series of incubations that result in the accumulation of sequence information. A reagent may be delivered, for example, by a robotically carried comb or pipette array, or preferably by bulk or flow-through addition of the reagent. Separate reagents in their respective buffers are represented by the jar in the left hand portion of the diagram and these are passed to the support array 10 by automated control in the order for performing the sequencing chemistry described herein. Sequencing occurs either following template-directed adaptor ligation (as described for Embodiments 1 and 2 in relation to FIGS. 1 and 2 herein) or following template-directed polymerization (as described in relation to FIGS. 3 and 4). Simultaneous retrieval of sequence information from several thousand templates following template-directed incorporation of a label, is then done by reader 50. Reading can be accomplished concurrently using a charge coupled device, which is illustrated on the top of FIG. 8, or may be performed in a slower scanning fashion by stepping the array past a line of scintillation or other detectors. By operating with a support array in which the DNA segments are immobilized in a small area and volume, a relatively strong signal is obtained free of the spreading and cross-reading losses inherent in gel sequencing or migration-dependent methods.

As described elsewhere herein, the method preferably includes a regeneration step. Illustratively, following the adaptor ligation step, an aliquot from each address undergoes PCR amplification in order to regenerate a template precursor for the next sequencing cycle. The appropriate primer sets and PCR mix are applied and the array undergoes a number of incubations. Preferably the device 20 has a heated stage with a Peltier cooler to accurately and quickly cycle the array through the required amplification regimen, or the array may pass to a separate processing chamber, e.g. an air oven thermal cycler of conventional type, for PCR amplification as illustrated on the bottom of the diagram. Following incubation with a reagent or PCR amplification, the DNA segments are magnetically pelleted and washed to remove the reagent and any byproducts prior to a subsequent step. The magnet and wash buffer are illustrated by device processes or subassembly 40 on the right hand portion of FIG. 8.

Once the necessary set of adapters and primers for cutting and amplification sets have been determined, the process steps are straightforward, and well-defined nucleotide determinations are achieved with small amounts of sample. The support arrays may thus carry a large number of sites. A chip or group of chips with 90,000 defined addresses will for example, allow the amplification of 90,000 DNA segments using PCR. Simultaneous amplification of a large number of samples may be done with a robotic thermal cycler using the approach of Meier-Ewert S, E Maier, A Ahmadi, J Curtis, H Lehrach. *An automated approach to generating expressed sequence catalogues.* Nature 1993; 361: 375–376 and Drmanac S, R Drmanac. *Processing of cDNA and genomic kilobase-size clones for massive screening, mapping, and sequencing by hybridization.* BioTechniques 1994; 17: 328–336, as applied to PCR. The invention also contemplates that the support be a microchip, in which case the teachings of PCR amplification on a microchip by several investigators are modified to include multiplex PCR amplification features for carrying out the methods described here. See, for example Wilding P, M A Shoffner, L J Kricka. *PCR in a silicon microstructure.* Clinical Chemistry 1994; 40: 1815–1818; Shouffner M A, J Cheng, G E Hvichia, L J Kricka, P Wilding. *Chip PCR. I. Surface passivation of microfabricated silicon-glass chips for PCR.* Nucleic Acid Research 1996; 24: 375–379; Cheng J, M A Shoffner, G E Hvichia, L J Kricka, P Wilding. *Chip PCR II. Investigation of different PCR amplification systems in microfabricated silicon-glass chips.* Nucleic Acid Research 1996; 24: 380–385; Bums M A, C H Mastrangelo, T S Sammarco, F P Man, J R Webster, B N Johnson, B Foerster, D Jones, Y Fields, A R Kaiser, D T Burke. *Microfabricated structures for integrated DNA analysis.* Proc. Natl. Acad. Sci. U.S.A. 1996; 93: 5556–5561.

Automated sequencing is described below for a chip with 90,000 addresses using a protocol for Embodiment 1. One of the primers in each PCR amplification is biotinylated, allowing these products to be bound to magnetic streptavidin. The opposite primer contains the recognition domain for FokI restriction endonuclease. If FokI is used as the restriction endonuclease, and sequencing is done in intervals of nine nucleotides, nine initial templates are generated for each of 10,000 DNA regions to be sequenced. This is accomplished by using primers with offset FokI restriction endonuclease recognition domains, as described extensively elsewhere herein. In the case where the DNA samples to be sequenced are vector inserts, primers are generated that anneal to the vector, so that only a few primers need to be synthesized to sequence the 90,000 DNA segments.

Following PCR amplification, the DNA segments are bound to magnetic streptavidin and magnetically pelleted, washed, and incubated with FokI in the corresponding buffer at 37° C., resulting in generation of the initial templates. After magnetic pelleting and washing, the 90,000 initial templates are incubated with a DNA ligase and the four sequencing adaptors, each with a unique label. Following magnetic pelleting and washing step to remove unligated adaptors, the ligated adaptor at each address is identified, for example with an automated reader using a charge coupled device. This is done in one embodiment by imaging the support array onto a CCD, and using automated analysis of the image pixels to threshold and read the luminescent labels, or by the approach described in Eggers M, M Hogan, R K Reich, J Lamture, D Ehrlich, M Hollis, B Kosicki, T Powdrill, K Beattie, S Smith, R Varma, R Gangadharan, A Mallik, B Burke, D Wallace. *A microchip for quantitative detection of molecules utilizing luminescent and radioisotope reporter groups.* BioTechniques 1994; 17: 516–525 or Lamture J B, K L Beattie, B E Burke, M D Eggers, D J Ehrich, R Fowler, M A Hollis, B B Kosicki, R K Reich, S R Smith, R S Varma, M E Hogan. *Direct detection of nucleic acid hybridization on the surface of a charged coupled device.* Nucleic Acid Research 1994; 22: 2121–2125.

Following reading of the labels, new template-precursors are regenerated by PCR amplification, bound to magnetic streptavidin, magnetically pelleted, washed, and cut with FokI, generating a new set of templates corresponding to the previous set of templates but with each strand shortened by nine nucleotides when compared to the prior corresponding template.

PCR amplification is preferably carried in such a way as to limit "noise." This may be accomplished by amplifying only a small portion of each ligation mixture to prevent successive exponential PCR amplifications from generating an accumulation of products during successive sequencing cycles. Obtaining a small aliquot from each ligation mixture for PCR amplification is performed in an automated fashion by device 20, and this can be accomplished by one of several techniques: removal or retention of an aliquot of the ligation mixture.

Removal of an aliquot for PCR amplification may be done by use of a dispersible solid phase, such as magnetic streptavidin. In a microtiter plate embodiment a subassembly such as a spotting robot that uses a pin transfer device may be used to transfer a small aliquot from each site on the microtiter plates as reported in the above-cited Meir-Ewert et al. article. When using a chip, a small aliquot can be removed by using an analogous hedgehog comb device as reported in Rosenthal A, O Coutelle, M Craxton. *Large-scale production of DNA sequencing templates by microtitre format PCR.* Nucleic Acid Research 1993; 21: 173–174, or by using a blotter to retain a small portion from each of the sample sites, followed by washing out of the remaining contents. PCR amplification is then performed using these retained aliquots as the templates. Other methods for retaining a small aliquot can be implemented such as a low intensity magnetic separation, or by using a chip with chambers shaped or positioned in relation to the flow path to retain a small aliquot by mechanical means when supernatant is removed (e.g. with a lip).

Alternatively, to prevent the accumulation of PCR product during successive sequencing cycles, the automated device may be operated to retain only a small amount of each PCR product for subsequent steps. This can be done by using a streptavidin coated manifold as reported in Lagerkvist A, J Stewart, M Lagerstrom-Fermer, U Landegren. *Manifold sequencing: Efficient processing of large sets of sequencing reactions.* Proc. Natl. Acad. Sci. U.S.A. 1994; 91: 2245–2249 and inserting the manifold into the amplification mixture to bind a small proportion of the biotinylated PCR products. In this case, the manifold-bound DNA segments are then moved to and dipped into individual reagents in subsequent steps, rinsing the manifold with wash buffer between steps, so that while PCR amplification occurs in the chip, other steps are carried using DNA segments that are bound to the manifold.

Removal or retention of an aliquot may also be effected by using a cleavable linkage, e.g. a chemically- or photo-cleavable linkage arm such as reported in Dawson B A, T Herman, J. Lough: *Affinity isolation of transcriptionally active murine erythroleukemia cell DNA using a cleavable biotinylated nucleotide analog.* Journal of Biological Chemistry 1989; 264: 12830–12837, and Olejnik J, E Krzymanska-Olejnik, K J Rothschild: *Photocleavable biotin phosphoramidite for 5'-end-labeling, affinity purification and phosphorylation of synthetic oligonucleotides.* Nucleic Acids Research 1996; 24: 361–366. In this case the cleavable linkage is employed for a portion, e.g. a small fraction, of the linkages used to attach the ligated DNA to the solid support or matrix. Cleavage then releases only the cleavably-bound DNA, permitting removal of a controlled portion of the DNA products. The PCR process may also be controlled by rendering much of the DNA product inaccessible to primer anealing and extension, for example by binding the DNA to a non-dispersible solid matrix or by pelleting a dispersible matrix. This takes advantage of the observation that immobilization of a nucleic acid component during PCR amplification reduces the efficiency of DNA amplification during solid phase PCR. Kohsaka H, D A Carson. *Solid Phase Polymerase chain reaction*. Journal of Clinical Laboratory Analysis 1994;8:452455.

FIG. 8 illustrates the reagent supply section 30 of the device to also contain DNA polymerase and ddNTPs. These have not been mentioned in the above description, but are used in the sequencing methods of Embodiments 3 and 4 described above with relation to FIGS. 3 and 4, using labeled ddNTPs. In the method of FIG. 3, the automated apparatus is operated so that following FokI digestion, magnetic binding, and washing, the DNA templates are incubated with a DNA polymerase and the four nucleotide terminators, each with a unique label. Following magnetic binding and washing, the incorporated label at each address is identified using the charge coupled device or other detector and, as before, the readings are passed as ordered information to the microprocessor data handler to note the additional nucleotide or nucleotides read at each site. Then, an adaptor is ligated to each of the templates. This is followed by PCR amplification which regenerates the next set of template precursors for the next sequencing cycle.

The above described automated process is highly efficient. By using unique adaptors and corresponding amplification primers during each sequencing cycle, about twenty sequencing cycles can be carried out, resulting in the sequencing of 180 nucleotides, of which typically at least 160 nucleotides will lie outside the primer in the end being sequenced. Thus, providing these DNA segments do not contain an internal FokI recognition domain, the above-described steps will generate 1,600,000 nucleotides of new sequence from a single 100×100 well chip. Since the FokI recognition domain has a five bp recognition domain, it is predicted to occur approximately every 1000 bp ($4^5$=1024) in random sequence. If the average size of each amplified fragment lying between the amplifying primers is 300 bp, then about 30% of the DNA segments to be sequenced will contain an internal FokI site and will not be successfully sequenced using only this simple protocol. Thus, in DNA sequences with a random distribution of equal numbers of GATC nucleotides, about 70% of the fragments will be successfully sequenced, resulting in the sequencing of approximately 1,120,000 nucleotides rather than 1,600,000.

This processing obstacle imposed by pre-existing FokI recognition domains may be addressed by hemi-methylating these recognition domains. The methods described in FIGS. 1 and 3 do not provide for the hemi-methylation of those FokI recognition domains that lie outside the adaptor encoded domain. Prior studies such as Looney M C, L S Moran, W E Jack, G R Feehery, J S Benner, B E Slatko, G G Wilson. *Nucleotide sequence of the FokI restriction-modification system: Separate strand-specificity domains in the methyltransferase*. Gene 1989; 80: 193–208 have shown that hemimethylation of the FokI recognition domain prevents cutting from being mediated by these domains. However, since each strand of the FokI recognition domain contains all four nucleotides, the PCR based method described by Padgett and Sorge in Padgett K A, J A Sorge. *Creating seamless junctions independent of restriction sites in PCR cloning*. Gene 1996; 168: 31–35 cannot be used to hemi-methylate such internal sites. Rather, when carrying out the invention with FokI, hemi-methylation requires the use of the method of Han and Rutter described in Han J, Rutter W J. *λgt22S, a phage expression vector for the directional cloning of cDNA by the use of a single restriction enzyme SfiI*. Nucleic Acids Res 1988; 16: 11837 as noted above.

The method is thus augmented by the following step: Following PCR amplification, binding to streptavidin and magnetic pelleting, the non-biotinylated strand is removed by denaturation and magnetic pelleting, followed by washing to remove reagents and primers. Since FokI cutting requires a double-stranded recognition domain, as reported by Podhajska A J, W Szybalski. *Conversion of the FokI endonuclease to a universal restriction enzyme: Cleavage of phage M13mp7 DNA at predetermined sites*. Gene 1985; 40: 175–182, this site is recreated, and the internal FokI sites are hemi-methylated, by using a primer containing the FokI recognition domain. This primer is complementary to the lower stand of the ligated sequencing adaptor up to the degenerate or universal nucleotides, and polymerization occurs using four nucleotides except that N6-methyl-dATP substituted for dATP. This process thus regenerates the adaptor encoded FokI recognition domain and hemimethylates those recognition domains that lie internal to the sequencing adaptor encoded domain. The DNA segments, once hemi-methylated, are then sequenced by the automated steps described above.

The invention contemplates a number of practical implementations of novel chip-based support arrays for carrying out the described steps in an automated manner.

Chips that house 50,000 DNA segments can be generated by microfabrication of microchambers using photolithography following the approaches and teachings of Wilding P, M A Shoffner, LJ Kricka. *PCR in a silicon microstructure*. Clinical Chemistry 1994; 40: 1815–1818; of Kikuchi Y, K Sato, H Ohki, T Kaneko. *Optically accessible micrchannels formed in a single-crystal silicon substrate for studies of blood rheology*. Microvascular Research 1992; 44: 226–240; of Woolley A T, R A Mathies. *Ultra-high-speed DNA fragment separations using microfabricated capillary array electrophoresis chips*. Proc. Natl. Acad. Sci. U.S.A. 1994; 91: 11348–11352; of Baxter G T, L J Bousse, T D Dawes, J M Libby, D N Modlin, J C Owicki, J W Parce. *Microfabrication in silicon microphysiometry*. Clin. Chem. 1994; 40: 1800–1804; of Kricka L J, X Ji, O Nozaki, P Wilding. *Imaging of chemiluminescent reactions in mesoscale silicon-glass microstructures*. J. Biolumin. 1994; 9: 135–138; or may be fabricated using molded or etched polymers as described by Matson R S, J Rampal, S L Jr. Pentoney, P D Anderson, P Coassin. *Biopolymer synthesis on polypropylene supports: Oligonucleotide arrays*. Analytical Biochemistry 1995; 224: 110–116. Alternatively, chip addresses may be separated by hydrophobic borders which may, for example, be implemented with conventional sample cell construction techniques or formed by processes of lithography and chemical treatment. Movement of the reagents to and from this chip can be done using pumps as reported in Bums M A, C H Mastrangelo, T S Sammarco, F P Man, J R Webster, B N Johnson, B Foerster, D Jones, Y Fields, A R Kaiser, D T Burke. *Microfabricated structures for integrated DNA analysis*. Proc. Natl. Acad. Sci. U.S.A. 1996; 93: 5556–5561 and in Wilding P, J Pfahler, H H Bau, J N Zemel, L J Kricka. *Manipulation and flow of biological fluids in straight channels micromachined in silicon*. Clinical Chemistry 1994; 40: 43–47. Alternatively, fluids may be brought to the sites by centrifugal force.

In this case the overall requirements for conduits, valves and wash-out passages may be substantially reduced, as it is only necessary to supply each reagent or solution to a central position communicating with the array. The array itself may mount in a shallow tray or cover assembly which effectively channels the flow to the array sites. In general, the sequencing method of the invention does not require the transfer of small amounts of liquids through capillaries, and therefore avoids many of the technological obstacles resulting from shearing forces encountered in low diameter capillary flow, as reported in Wilding P, J Pfahler, H H Bau, J N Zemel, L J Kricka. *Manipulation and flow of biological fluids in straight channels micromachined in silicon*. Clinical Chemistry 1994; 40: 43–47.

Figure 9:
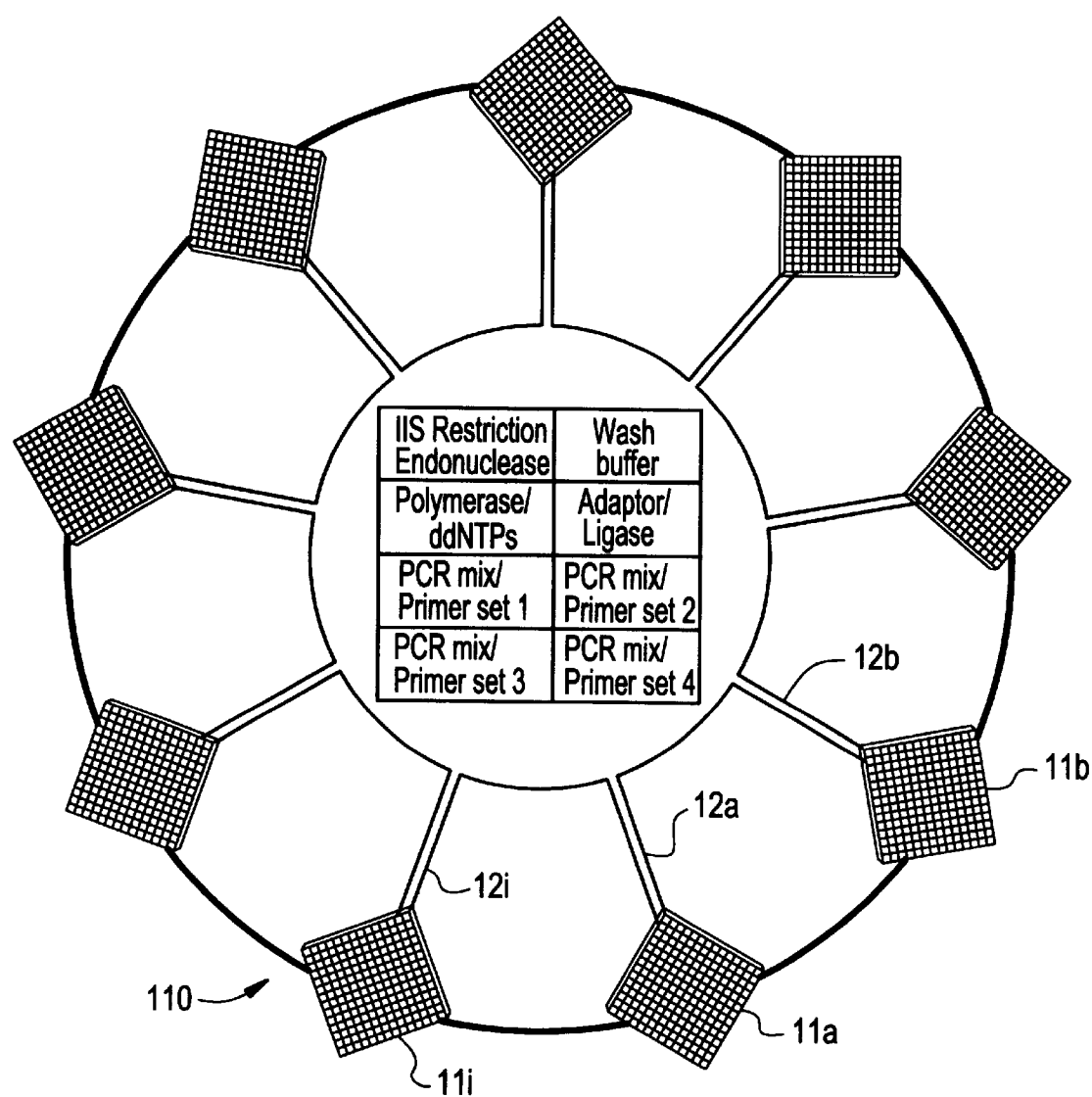
FIG. 9 is a schematic representation of chips and reagents for DNA sequencing on a disk. The transfer of reagents to multiple chips occurs through centrifugal force by disk rotation.

FIG. 9 shows an embodiment of a system 110 in which movement of reagents onto chips is effected by centrifugal force. In this device, the chips 10' are on a turntable. Reagents are placed closer to the center of the turntable, and rotating the turntable drives the reagents radially outward directly to one or more chips. Centrifugal force also allows reagents to be removed from chips. A chip or chip holder itself is preferably configured for flow-through operation to simplify and enhance the removal of reagents (see, e.g., Beattie K L, W G Beattie, L Meng, S L Turner, R Coral-Vazquez, D D Smith, P M McIntyre, D D Dao. *Advances in genosensor research*. Clinical Chemistry 1995; 41: 700–706).

In the device 110, illustratively set up for the processes described herein, nine support arrays 11a, 11b, . . . 11i are located around a rotating stage with each communicating at a radially innermost corner with a corresponding flow supply conduit 12a, 12b, . . . 12i. Outlets (not shown) may be to a common drain. Thus each support array in this device embodiment may receive a separate set of reagents. For example, the nine arrays may be initially loaded with identical DNA samples in each respective well, and then all samples in an array processed to produce templates offset by a fixed x, with x={1,2 . . . 9} different for each array. Once the nine sets of templates on the corresponding supports have been created, running the sequencing process steps of the present method then produces a continuous nucleotide sequence for each of the initial segments.

When performing the amplification steps, during incubations, the magnetic streptavidin bound DNA can be suspended by shaking or by magnetic oscillation as described in the *Product information on MixSep$^c$*. Sigris Research, Inc. Brea, Calif. To retain a small portion of the magnetic particles prior to the addition of PCR reagents and PCR amplification, the magnetic pelleting can be adjusted electrically. In the chip embodiment, PCR thermal cycling is very efficient, since heat transfer occurs rapidly over short distances. The thermal cycler can be a Peltier heater-cooler device built into the stage, a set of fixed temperature plates or baths which are successively placed in thermal contact with the chips, or an air oven (see, for example, Meier-Ewert S, E Maier, A Ahmadi, J Curtis, H Lehrach. *An automated approach to generating expressed sequence catalogues*. Nature 1993; 361: 375–376; Drmanac S, R Drmanac. *Processing of cDNA and genomic kilobase-size clones for massive screening, mapping, and sequencing by hybridization*. BioTechniques 1994; 17: 328–336; Wilding P, M A Shoffner, L J Kricka. *PCR in a silicon microstructure*. Clinical Chemistry 1994; 40: 1815–1818; and Shouffner M A, J Cheng, G E Hvichia, L J Kricka, P Wilding. Chip PCR. I. *Surface passivation of microfabricated silicon-glass chips for PCR*. Nucleic Acid Research 1996; 24: 375–379. Reading the identity of incorporated label can be carried out using a charge coupled device, as described above, or using a fluorescent microscope, fiber-optic detectors, biosensors, gas phase ionization detector, or a phosphorimager as described in Kinjo M, R Rigler. *Ultrasensitive hybridization analysis using fluorescence correlation spectroscopy*. Nucleic Acid Research 1995; 23: 1795–1799; Mauro J M, L K Cao, L M Kondracki, S E Walz, J R Campbell. *Fiber-optic fluorometric sensing of polymerase chain reaction-amplified DNA using an immobilized DNA capture protein*. Analytical Biochemistry 1996; 235: 61–72; Nilsson P, B Persson, M Uhlen, P Nygren. *Real-time monitoring of DNA manipulations using biosensor technology*. Analytical Biochemistry 1995; 224: 400–408; Eggers M, D Ehrlich. *A review of microfabricated devices for gene-based diagnostics*. Hematologic Pathology 1995; 9: 1–15.

Even without special biochip microfabrication, the methods of the present invention are advantageously implemented in a device that operates in a microtiter plate format. In this case the construction of the subassemblies for the scintillation counting of multi-well microtiter plates and for the automated picking of colonies into the wells, as well as the necessary reagent introduction and thermal cycling to amplify DNA simultaneously in multiple multi-well microtiter plates, allows the simultaneous amplification, treatment and reading of the array of samples. Indeed, with prior art subassemblies handling 120 plates, each with 384 wells, 46,080 samples may be processed simultaneously. Therefore, the sequencing protocol estimated to sequence 160 nucleotides in a clone insert would sequence simultaneously 204,800 nucleotides from 1280 clones using a single 120 plate thermal cycler, 384 well scintillation counter, one radiolabel, a 384 pin transfer device (e.g., a hedgehog comb) and a robotic pipetter. [46,080 wells/9 initial templates=5120 samples; 5120/4 ligations=1280 samples (clones). 1280 clones×160 nucleotides/clone=204,800 nucleotides]. (Meier-Ewert S, E Maier, A Ahmadi, J Curtis, H Lehrach. Nature 1993; 3631:375–376.)

With the foregoing overview of the organization of a method and apparatus for large scale or multiplex processing of collections of segments, a detailed description will now be given of several embodiments of the sequencing method as applied to a single segment.

This invention is further illustrated by the following Exemplification which should not be construed as limiting. The contents of all references and published patents and patent applications cited throughout the application are hereby incorporated by reference.

EXEMPLIFICATION

Experimental Strategy

The present invention allows one to sequence numerous DNA segments in parallel without running a gel. It is an iterative method that allows one to sequence DNA in fixed intervals of greater than one nucleotide, and provides a means for regenerating the desired DNA segment following each iterative cycle. This is accomplished by the iterative application of a DNA ligase and an enzyme, e.g., a class-IIS restriction endonuclease, to generate templates for DNA sequencing. One simple schematic is outlined below.

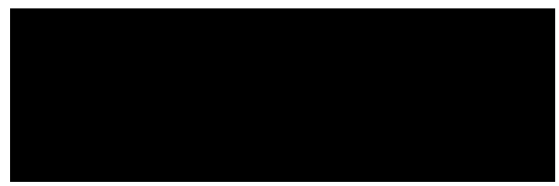

In each cycle, adaptor ligation to one end of the DNA segment is followed by class-IIS restriction endonuclease cutting. The recognition domain of the class-IS restriction endonuclease is encoded by the ligated adaptor, allowing restriction endonuclease digestion to trim the DNA segment, generating a new overhang sequence. One or both strands of an adaptor can be ligated, or one or both ends of a single-strand hairpin adaptor can be ligated. Also, one strand of an adaptor can be ligated followed by hybridization, without ligation of the complementary strand, to generate a double-stranded recognition domain. Iterative cycles generate a series of single-strand overhangs, each constituting a DNA template. The single-stranded overhangs are separated by fixed intervals that are limited by the distance between the recognition domain and the cut site in the cleavage domain for the class-IIS restriction endonuclease encoded by the ligated adaptor. This method exploits the separation of the cleavage domain and the recognition domain of class-IIS restriction endonucleases by allowing the sequencing in strides limited only by the distance between the recognition domain and the cleavage domain cut sites, distinguishing it from other iterative approaches. Since each DNA template is a short single-stranded region attached to double-stranded DNA, these single-strands have little opportunity to form secondary structures, providing a considerable advantage over competing methods.

The overhang generated after each cycle constitutes a DNA template that is sequenced in one of a variety of ways. One way uses template-directed DNA ligation to discriminate between nucleotides at the ligation junction, allowing this ligation to generate sequence information. This is illustrated below:

Successful ligation requires that an adaptor's single-stranded end be complementary to the double-stranded DNA's single-stranded overhang sequence at the ligation junction. Four adaptors (or adaptor subsets) are used during each ligation, with each of the four adaptors differing at the nucleotide positioned to undergo ligation at the template-directed ligation junction. Ligation to one of the four adaptors and identification of that adaptor allows identification of the nucleotide at the ligation junction, thus generating sequence information. Sequencing can be accomplished by fluorometry using adaptors tagged with distinct fluorescent labels. This is followed by class-IIS restriction endonuclease mediated end trimming of the DNA using the recognition domain encoded by the ligated adaptor. This recognition domain is positioned so that cleavage results in the removal of nucleotides from each strand of the DNA, creating a new template for subsequent template-directed ligation to one of four adaptors or adaptor subsets. This strategy can use an enzyme, e.g., a class II-S restriction endonuclease, that generates either a 5' or a 3' overhang sequence, as either type of overhang can serve as a template for template-directed ligation.

Another approach uses template-directed polymerization instead of template-directed ligation to sequence DNA. In this case, adaptor ligation can be template-directed but is not used to discriminate between nucleotides at the ligation junction. Sequencing occurs through a separate template-directed DNA polymerization step. In order to use template-directed polymerization to sequence the overhang sequence, the overhang must be a 5' overhang, since template-directed polymerization requires a recessed 3' end. A simple schematic of this approach is outlined below.

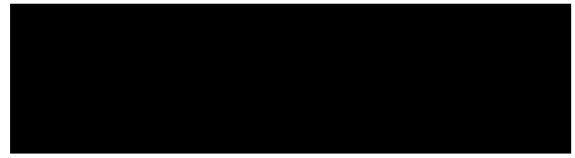

Ligation can be template-directed, occurring using an adaptor with a promiscuous nucleotide or nucleotides (degenerate or universal) at the ligation junction, so that this ligation is not used to discriminate between nucleotides at the ligation junction, and therefore does not generate sequence information. Ligation of the adaptor is followed by class-IIS restriction endonuclease trimming, generating a 5' overhang sequence. The 5' overhang has a recessed 3' end, forming a substrate for template-directed DNA polymerization. Template-directed polymerization occurs in the presence of each of the four labeled nucleotide terminators (e.g. ddNTPs). These nucleotide terminators can each have distinct fluorescent tags, so that following incorporation of one of these labeled nucleotide terminators, a fluorometer can identify the incorporated nucleotide (Prober J M, Trainor G L, Dam R J, Hobbs F W, Robertson C W, Zagursky R J, Cocuzza A J, Jensen M A, Baumeister K., *Science* 1987; 238:336–341). Iterative cycles of adaptor ligation and IIS cutting create new templates for sequencing by template-directed polymerization.

One obstacle inherent in iterative methods that generate a product is that even if the constituent enzymatic steps approach 100% completion, incompletely processed products can accumulate to significant levels. For example, during oligonucleotide synthesis of a 70-mer, requiring 69 couplings, a 99% coupling efficiency results in only 50% of the generated oligonucleotides being full length ($0.99^{69}=0.50$). The present invention eliminates this problem by allowing one to sequence in intervals of greater than one nucleotide. For example, the FokI recognition domain is separated from its cleavage domain by nine nucleotides. Using a FokI based protocol, single-strand overhangs can be generated in each cycle that are separated by nine nucleotide long intervals over time and space, so that five cycles will allow one to span 45 nucleotides, instead of just five nucleotides using an iterative method that sequences consecutive nucleotides (e.g. the base addition DNA sequencing scheme). This is termed striding, as it covers a considerable stretch of DNA with few iterative steps. Sequencing single nucleotides in intervals of greater than one nucleotide requires the sequencing of the nucleotides that fall within each interval. One sequencing method generates DNA templates separated by intervals of nine nucleotides, and sequences a single nucleotide in each template, by making nine initial templates for each DNA segment being sequenced, such that sequencing these nine initial templates will sequence nine adjacent nucleotides. The nine initial templates can be generated by ligating one end of each DNA segment to be sequenced to nine distinct adaptors in nine separate ligations, each adaptor containing a FokI recognition domain, with these domains offset from each other by one base pair when comparing adjacently positioned recognition domains. In one embodiment, the DNA segment to be sequenced is generated by PCR amplification, and offset recognition domains are incorporated during PCR amplification by encoding the recognition domain into one of the amplifying primers according to the method of Mullis K, Faloona F, Scharf S, Saiki R, Horn G, Erlich H., *Cold Spring Harbor Symposia on Quantitative Biology*, Cold Spring Harbor Laboratory, LI:263–273. When the DNA samples to be sequenced are vector inserts, as in a genomic or cDNA library, a set of initial template precursors can be generated for each DNA insert to be sequenced using a single set of initial adaptors. For example, following digestion with a restriction endonuclease that cuts the vector adjacent to each insert, offset recognition domains can be appended to each of the numerous vector inserts through ligation to each of the initial adaptors. This can be followed by PCR, to seal nicks and retrieve the product. An alternative approach is to use PCR alone to generate offset recognition domains. For example, when sequencing DNA libraries, primers can be designed to anneal to a vector sequence immediately flanking each insert. Once this set of DNA segments with offset (i.e., staggered) recognition domains is generated for each DNA segment to be sequenced, these DNA segments can be sequenced concurrently, so that the number of steps necessary to sequence a contiguous stretch of DNA in the original DNA segment is markedly reduced. Using any of the above approaches, only a few primers must be made to sequence numerous vector inserts. Furthermore, each of the nine products can have a uniquely positioned recognition domain, so that digestion with FokI cleaves both strands of each DNA segment and generates a set of nine overhang sequences positioned as a staggered array separated by one base pair. Generating several initial DNA templates for each DNA segment to be sequenced diminishes the number of successive steps necessary to sequence a given stretch of DNA, and therefore significantly diminishes the accumulation of background signal when sequencing over a given span of DNA.

In order to regenerate the product of interest following each cycle of restriction endonuclease digestion and adaptor ligation, an additional step is designed. Specifically, this invention uses adaptor ligation during each sequencing cycle. These ligated adaptors can differ during each cycle (or every several cycles), allowing the product generated following each cycle of restriction endonuclease digestion and template-directed ligation to have a unique end created by the ligated adaptor. This unique end can generate a primer annealing site during PCR, such that PCR can amplify the desired product over a million fold following each adaptor ligation step (Saiki R K, D H Gelfand, S Stoffel, S J Scharf, R Higuchi, G T Horn, K B Mullis, H A Erlich, *Science* 1988; 239:487–491). Nucleic acid amplification in vitro can be exponential, as is usually done, or linear, in which one primer undergoes one or more cycles of primer extension, followed by its removal and cycles of single primer extension using the opposite primer. This in vitro amplification step replenishes the desired product (some product is inevitably lost in prior steps), and prevents uncut products or unligated products from generating background signal. It also regenerates the template precursor by eliminating base mismatches, nicks, and displaced ends lying between the recognition domain and the cleavage domain following adaptor ligation. Thus, cutting efficiencies need not approach 100%; this method allows one to use lower concentrations of restriction endonuclease that preferably cut with very high specificity (>99.9%) for the canonical recognition domain (Fuchs R, R Blakesley, *Methods in Enzymology* 1983; 100:3–38). Furthermore, this method works well even when DNA ligation is inefficient, as when ligating fragments with a single nucleotide overhang, because the desired template precursor can be readily amplified over one million fold using PCR amplification. Also, following fill-in with labeled ddNTPs, even if the label interferes with ligation, only a fraction of those filled in would need to be labeled, as product regeneration through amplification in vitro does not require a large proportion of the filled-in product to undergo efficient ligation. The remaining product could either not undergo fill-in (in the presence of low numbers of labelled ddNTPs) or undergo fill-in in the presence of unlabelled ddNPTs (along with labelled ddNPTs). When using nucleic acid amplification in vitro to re-generate each template-precursor, the adaptor does not need to have a double-stranded recognition domain, as the recognition can be encoded by an adaptor containing only a single-strand of the recognition domain, with the double-stranded recognition domain generated during the nucleic acid amplification in vitro.

In one embodiment, recognition domains for the class-IIS restriction endonuclease used to generate the DNA templates that occur in the original DNA segment (internal to the ligated adaptor), are methylated or otherwise blocked to prevent cutting mediated by these internal domains. Blocking of internal recognition domains can be accomplished by treatment with the corresponding methylase (FokI methylase for Fok I restriction endonuclease (Kita K, H Kotani, H Sugisaki, M Takanami, *J Biol Chem* 1989;264:5751–5756, Looney M C, L S Moran, W E Jack, G R Feehery, J S Benner, B E Slatko, G G Wilson, *Gene* 1989; 80:193–208), prior to adaptor ligation. This prevents cutting mediated by these internal recognition domains, without preventing cleavage directed by the ligated adaptor (whose recognition domain is not methylated).

Hemi-methylation of these internal recognition domains can be carried out using the strategy of Han and Rutter or using the PCR-based strategy of Padgett and Sorge, as described in more detail herein (Han J. Rutter W J. *Nucleic Acids Res* 1988;16:11837, Padgett K A, J A Sorge, *Gene* 1996; 168:31–35). Each strategy hemi-methylates, and effectively blocks, internal recognition domains without methylating the primer-encoded recognition domain. The method of Padgett and Sorge cannot be used if each strand of the chosen recognition domain contains all four nucleotides, because PCR amplification cannot be carried out with selective methylation of those recognition domains that lie outside of the primer encoded recognition domain, as the strand antisense to the primer's recognition domain will be hemi-methylated during PCR. The method described by Han and Rutter can hemi-methylate the internal recognition domains regardless of the nucleotide composition of each strand of the recognition domain, and it can be incorporated into a linear amplification step.

The PCR-based method of Padgett and Sorge has the advantage of allowing the simultaneous exponential amplification of the product of interest along with hemi-methylation of the internal recognition domains. This is accomplished by amplification with a methylated nucleotide that does not lie within the sequence antisense to the recognition domain sequence in the amplifying primer, and can be carried out using ligated adaptors and amplifying primers that vary during each cycle (or every several cycles) as described. In this case, however, the 3' end of each amplifying primer must encode at least a portion of the restriction endonuclease recognition domain of the class-IIS restriction endonuclease used to trim the DNA segment. This may diminish the specificity of the PCR amplification for the product of interest, as these shared 3' ends may result in some amplification of uncut DNA products. The strategy of Han and Rutter can be modified to linearly amplify the product of interest, while simultaneously hemi-methylating the internal recognition domains. This can be carried out by iterative primer extensions using the primer encoding at least a portion of the recognition domain, with a methylated nucleotide substituting for its normal counterpart, before or after reiterative primer extensions with the opposite primer using the four normal dNTPs. Any of the above strategies for hemi-methylating internal recognition domains can be carried following in vitro amplification of the product of interest, and such prior in vitro amplification could occur through PCR or a related method, such as strand displacement amplification (Walker G T, M S Fraiser, J L Schram, M C Little, J G Nadeau, D P Malinowski *Nucleic Acids Research* 1992; 20:1691–1696). Such prior DNA amplification in vitro need not have a portion of the recognition domain incorporated into any of the amplifying primers, allowing exquisite specificity during product regeneration.

EXAMPLE 1

Demonstration of Interval Sequencing Mediated by Class-IIS Restriction Endonuclease Generated 5' Overhangs and Template-Directed Ligation Using a FokI based strategy, single nucleotides separated by intervals of nine nucleotides were sequenced using simple reagents and a scintillation counter. The initial template precursor was a 93 bp PCR product containing a portion of the Cystic Fibrosis Transmembrane Conductance Regulator gene that had been amplified directly from human genomic DNA. Sequencing was accomplished by template-directed ligation using six sequencing cycles. Following sequencing of the first nucleotide, five additional nucleotides were sequenced at nine nucleotide intervals, so that the sequencing covered a span of 46 nucleotides (1+(5×9)=46). The non-biotinylated primer used to generate the template precursor contained a recognition domain for FokI. The opposite primer had a biotinylated 5' end, and was used to bind the template precursor to magnetic streptavidin beads. Use of magnetic streptavidin beads allowed enzymatic reactions to occur in solution, and facilitated removal of a small aliquot for each PCR amplification step during the sequencing cycles. During the sequencing cycles, only two sets of adaptors were used, and each unique PCR amplifying primer used during the sequencing cycles was identical to the upper strand of the previously used adaptor, so that these unique amplifying primers contained the FokI recognition domain in their 3' ends, minimizing the number of oligonucleotides synthesized. In this protocol, identification of a nucleotide during each sequencing cycle took place using four ligation reactions (for the single template precursor). In each ligation, all four adaptors were present, with the 3' end of a different one of the four adaptors in each ligation tagged with $^{35}$S. Quantitation of retained $^{35}$S radiolabel was carried out using a scintillation counter, and a dominant signal for the correct nucleotide was clearly detected during each cycle. The details are outlined below:

Sequencing Adaptor Generation

Adaptor set #1 (lower strands of this adaptor set are shown in the box below) was generated as follows: 6.3 µl of the lower strand of the first three of the four adaptors (100 pmole/µl) were added, in three separate reactions (one for each oligonucleotide) to 4.4 µl H$_2$O, 3.3 µl 5× Terminal deoxynucleotidyl transferase buffer (500 mM cacodylate buffer, pH 6.8, 5 mM CoCl$_2$, 0.5 mM DTT); 1.3 µl Terminal deoxynucleotidyl transferase (20U/µl; Promega, Madison Wis.) and 1.0 µl [$^{35}$S]ddATP (12.5 µCi/µl). The final oligonucleotide was processed as described above, except that half amounts were used. All of the samples were incubated at 37° C. for one hour followed by heat inactivation at 70° C. for 10 minutes, resulting in a final volume of 16.3 µl for the first three labeled oligonucleotides, and a final volume of 8.2 µl for the final labeled oligonucleotide (with the 5' G).

5'P-<u>C</u>NNNCATCCGACCCAGGCGTGCG (SEQ ID NO: 1) or

5'P-<u>A</u>NNNCATCCGACCCAGGCGTGCG (SEQ ID NO:2) or

5'-P-<u>T</u>NNNCATCCGACCCAGGCGTGCG (SEQ ID NO:3) or

5'P-<u>G</u>NNNCATCCGACCCAGGCGTGCG (SEQ ID NO:4);
only the 5' end varies between these four
oligonucleotides, and this nucleotide is
underlined; the FokI recognition sequence is in
bold type; N represents nucleotides with
4-fold degeneracy.

The 16.3 µl of each of the first three labeled oligonucleotides were separately added to 2.5 µl 10× T$_4$ DNA Ligase buffer (660 mM Tris-HCl, 50 mM MgCl$_2$, 10 mM dithioerythritol, 10 mM ATP, pH 7.5) and to 6.2 µl of the upper strand of the sequencing adaptor (100 pmole/µl):

5'-CGCACGCCTGGGTCGGATG (SEQ ID NO:5);
the FokI recognition sequence is in bold type.

The last labeled oligonucleotide (with the 5' G) was processed as described above, except in half amounts, resulting in a final volume of 25 µl for each of the first three adaptors and 12.5 µl for the final adaptor.

Non-radiolabeled counterparts to the above four adaptors were generated by adding 20.0 µl (100 pmole/µl) of each of the first three lower strands, separately to 20.0 µl (100 pmole/µl) of the upper strand, 8.0 µl of 10× T$_4$ DNA Ligase buffer and 32 µl H$_2$O, for a final volume of 80 µl, and 10.0 µl (100 pmole/µl) of the final lower strand (with the 5' G) was added to half amounts of the above constituents, for a final volume of 40 µl. Each of the eight sets of adaptors (four radiolabeled and four non-radiolabeled) were incubated at 93° C. for 30 seconds followed by annealing at 25° C. for 5 minutes. The radiolabeled final adaptor (with the 5' G) was added to 12.5 µl H$_2$O, to bring the final volume to 25 µl, like the other radiolabeled adaptors, and the 40 µl of the non-radiolabeled final adaptor was added to 40 µl H$_2$O, to bring the final volume to 80 µl, like the other non-radiolabeled adaptors. Each adaptor with a 5' G was at half the concentration of the other adaptors based on ligation data from preliminary experiments.

Each radiolabeled adaptor was added to 25 µl of the non-radiolabeled adaptors with the other three 5' ends. This resulted in four adaptor #1 mixes, each with one radiolabeled adaptor and the remaining three non-radiolabeled adapters. Using four ligation mixtures allows one to sequence nucleotides using a single label and a simple detection apparatus (e.g. a scintillation counter).

Adaptor set #2 was made the same way as adaptor set #1, except that the four oligonucleotides for the lower strands of the adaptors were:

5'P-<u>C</u>NNNCATCCTCTGGGCTGCACGGG (SEQ ID NO:6) or

5'P-<u>A</u>NNNCATCCTCTGGGCTGCACGGG (SEQ ID NO:7) or

5'P-<u>T</u>NNNCATCCTCTGGGCTGCACGGG (SEQ ID NO:8) or

5'P-<u>G</u>NNNCATCCTCTGGGCTGCACGGG (SEQ ID NO:9);
only the 5' end varies between each of these four
oligonucleotides, and this nucleotide is
underlined; the FokI recognition sequence is in
bold type; N represents nucleotides with
4-fold degeneracy.

and the oligonucleotide for the upper strand of the adaptors was:

```
5'-CCCGTGCAGCCCAGAGGATG (SEQ ID NO:10);
the FokI recognition sequence is in bold type.
```

Initial Sequencing Template Generation

PCR amplification of a 93 bp initial template precursor from human genomic DNA was carried out using primers A and B (shown in the box below) as follows: 200 ng human genomic DNA (Promega, Madison Wis.) in 2.0 μl was placed with 41.6 μl H$_2$O, 6.0 μl 10× buffer (100 mM Tris-HCl pH 8.3, 1.0 M KCl, 0.5% Tween 20, 50% Glycerol), 4.0 μl containing 5.0 mM each dNTP (100 mM stock (Boehringer Mannheim, Indianapolis Ind.) diluted in H$_2$O), 1.0 μl Primer A (25 pmole/μl), 1.0 μl Primer B (25 pmole/μl), 4.4 μl 25 mM Mg(OAc)$_2$, in each of four microcentrifuge tubes. A wax bead was added (Perkin Elmer, Foster City Calif.) and the tubes were heated to 80° C. for 3 minutes and then cooled to 25° C. An upper layer of reagents consisting of 35.0 μl H$_2$O, 4.0 μl 10× buffer and 1.0 μl rTth DNA Polymerase (2.5 U/μl; Perkin Elmer) was placed on top of each wax bead, and the four tubes underwent an initial denaturation step at 94° C. for 1 minute followed by 30 thermal cycles using the following parameters (94° C. for 30 seconds, 50° C. for 30 seconds), a final extension at 72° C. for 7 minutes, and a 4° C. soak.

```
Primer A: GTTTTCCTGGATGATGCCCTGGC (SEQ ID NO: 11);
mismatch to genomic DNA underlined;
FokI recognition sequence in bold type.
Primer B: 5' Biotin-CATGCTTTGATGACGCTTCTGTATC
(SEQ ID NO: 12);
the biotinylated 5' end was generated
during oligonucleotide synthesis using a biotin
phosphoramidite (Glenn Research, Sterling VA).
```

The samples were combined, and 360 μl of this product was incubated with 4.0 μl Exonuclease I (20U/μl; Epicentre, Madison Wis.) at 37° C. for 30 minutes, followed by heat inactivation at 80° C. for 15 minutes. The sample was purified by glass bead extraction using Mermaid (BIO101, La Jolla Calif.) and was suspended in 90 μl TE (10.0 mM Tris-HCl pH 8.0, 1.0 mM EDTA). Eighty μl of this product was digested with 5.0 μl FokI (3U/μl; Boehringer Mannheim) in the manufacturer's 1× buffer in a total volume of 100 μl at 37° C. for 1 hour followed by heat inactivation at 65° C. for 15 minutes. 87.5 μl of this product was mixed with 90 μl of washed magnetic streptavidin beads in 2× binding-wash buffer (prepared from 150 μl Dynabeads M-280 Streptavidin, Dynal, Oslo Norway, as directed by the manufacturer), incubated for 1 hour at room temperature (23° C.) with mixing to disperse the magnetic beads, magnetically pelleted (Dynal Magnetic Pellet Concentrator-E), washed three times in binding-wash buffer, and resuspended in 50 μl TE.

Adaptor Ligation

The template underwent ligation separately to each of the four adaptor mixes in adaptor set #1 as follows: 12.5 82 l of the template was added to 10 μl of each adaptor mix, 17.5 μl H$_2$O, 5.0 μl 10× T$_4$ DNA Ligase buffer, and 5.0 μl T$_4$ DNA Ligase (1.0 U/μl; Boehringer Mannheim, Indianapolis Ind.) and incubated at 23° C. for 1 hour with mixing every 15 minutes. Then, the mixture was magnetically pelleted, the supernatant removed, and the pellets were washed three times in binding-wash buffer and then were resuspended in 50 μl TE.

Scintillation Counting

Forty μl each of the four ligated samples were added to 2.5 ml of scintillation fluid (Beckman Ready Gel, Beckman Instruments, Fullerton Calif.) in a scintillation vial and underwent scintillation counting using a Beckman LS 1801 scintillation counter.

PCR Amplification

One μl from each ligation (from the 10 μl remaining that did not undergo scintillation counting) underwent PCR amplification as was done in generating the initial template precursor, except that 42.6 μl H$_2$O was used (instead of 41.6 μl) and the upper strand of sequencing adaptor set #1 was used as the PCR primer in place of Primer A.

Second Sequencing Cycle

The steps were identical to the first sequencing cycle, except that the adaptor set used for adaptor ligation was adaptor set #2, and the upper strand of sequencing adaptor set #2 was used as a PCR primer instead of the upper strand of sequencing adaptor set #1.

Third Sequencing Cycle

The steps were identical to the second sequencing cycle, except that the adaptor set used for adaptor ligation was adaptor set #1, and the upper strand of sequencing adaptor set #1 was used as a PCR primer instead of the upper strand of sequencing adaptor set #2.

Subsequent Sequencing Cycles

Following the third sequencing cycle, the second sequencing cycle was repeated, and following this second sequencing cycle, the third sequencing cycle was repeated, and following this third sequencing cycle, the second sequencing cycle was repeated through the scintillation counting step.

Sequencing Results

The FokI recognition domain is positioned in each ligated adaptor so that one nucleotide was sequenced at 9 nucleotide intervals. The initial template precursor is shown below, along with its FokI recognition domain (bold type). Underlined sequences are the original amplifying primers (Primer A and Primer B). The cut sites for this recognition domain, as well as subsequent cut sites directed by ligated adaptors, are shown by dissecting lines. Cleavage generates a single-strand overhang that constitutes a template, and the nucleotide sequenced at each interval is shown by a numbered asterisk, the number identifying the sequencing cycle for sequencing the nucleotide.

The scintillation counts for each of the four adaptors at each sequencing interval (identified by sequencing cycle) is shown below. The highest counts are in bold type. Counts for the correct nucleotide were four fold greater than background (counts for any other nucleotide) in the first five cycles and greater than twice background in the final cycle (cycle 6).

| | Sequencing Cycle Number | | | | | |
|---|---|---|---|---|---|---|
| | 1 | 2 | 3 | 4 | 5 | 6 |
| Template nucleotide at ligation junction | A | A | T | T | G | T |
| Predicted 5' end of adaptor undergoing ligation | T | T | A | A | C | A |
| Scintillation counts for adaptors (identified by $^{35}$S labelled 3' end) | | | | | | |
| G | 662 | 1,504 | 1,625 | 6,793 | 1,441 | 1,779 |
| A | 2,568 | 1,618 | 68,007 | 34,753 | 3,335 | 14,397 |
| T | 32,917 | 32,563 | 5,797 | 3,934 | 14,787 | 2,962 |
| C | 1,703 | 988 | 1,704 | 1,745 | 67,233 | 5,304 |

EXAMPLE 1B

Demonstration of Interval Sequencing Mediated by Class-IIS Restriction Endonuclease Generated 5' Overhangs and Template-Directed Ligation Using a FokI based strategy, single nucleotides separated by intervals of nine nucleotides were sequenced using simple reagents and a scintillation counter. The initial template precursor was a 93 bp PCR product containing a portion of the Cystic Fibrosis Transmembrane Conductance Regulator gene that had been amplified directly from human genomic DNA. Sequencing was accomplished by template-directed ligation using three sequencing cycles. Following sequencing of the first nucleotide, two additional nucleotides were sequenced at nine nucleotide intervals, so that the sequencing covered a span of 19 nucleotides (1+(2×9)=19). The non-biotinylated primer used to generate the template precursor contained a recognition domain for FokI. The opposite primer had a biotinylated 5' end, and was used to bind the template precursor to magnetic streptavidin beads. Use of magnetic streptavidin beads allowed enzymatic reactions to occur in solution, and facilitated removal of a small aliquot for each PCR amplification step during the sequencing cycles. During the sequencing cycles, only two sets of adaptors were used, and each unique PCR amplifying primer used during the sequencing cycles was identical to the upper strand of the previously used adaptor. In this test protocol, identification of a nucleotide during each sequencing cycle took place using four ligation reactions (for the single template precursor). In each ligation, all four adaptors were present, with the 3' end of a different one of the four adaptors in each ligation tagged with $^{32}$P. Quantitation of retained $^{32}$P radiolabel was carried out using a scintillation counter, and a dominant signal for the correct nucleotide was clearly detected during each cycle. The details are outlined below:

Sequencing Adaptor Generation

Adaptor set #1 (lower strands of this adaptor set are shown in the box below) was generated as follows: 20.0 µl of the lower strand of the four adaptors (100 pmole/µl) were added, in four separate reactions (one for each oligonucleotide) to 12.5 µl H$_2$O, 12.0 µl 5× Terminal deoxynucleotidyl transferase buffer (500 mM cacodylate buffer, pH 6.8, 5 mM CoCl$_2$, 0.5 mM DTT), 3.0 µl Terminal deoxynucleotidyl transferase (20U/µl; Promega, Madison Wis.) and 12.5 µl [$^{32}$P]dATP (10.0 µCi/µl). All of the samples were incubated at 37° C. for one hour followed by heat inactivation at 70° C. for 10 minutes. Unincorporated [$^{32}$P]dATP was removed from each tube using a Qiagen nucleotide removal column (Qiagen, Chatsworth Calif.) and each oligonucleotide was eluted in 50 µl TE.

5'P-<u>C</u>NNNCATCCGACCCAGGCGTGCG (SEQ ID NO:13) or

5'P-<u>A</u>NNNCATCCGACCCAGGCGTGCG (SEQ ID NO:14) or

5'P-<u>T</u>NNNCATCCGACCCAGGCGTGCG (SEQ ID NO:15) or

5'P-<u>G</u>NNNCATCCGACCCAGGCGTGCG (SEQ ID NO:16);
only the 5' end.varies between these four oligonucleotides, and this nucleotide is underlined; the FokI recognition sequence is in bold type; N represents nucleotides with 4-fold degeneracy.

15.8 µl of each of the first three labeled oligonucleotides were separately added to 2.5 µl 10× T$_4$ DNA Ligase buffer (660 mM Tris-HCl, 50 mM MgCl$_2$, 10 mM dithioerythritol, 10 mM ATP, pH 7.5), 0.5 µl H$_2$O and to 6.2 µl of the upper strand of the sequencing adaptor (100 pmole/µl):

5'-CGCACGCCTGGGTCGGATG (SEQ ID NO:17);
the FokI recognition sequence is in bold type.

the last labeled oligonucleotide (with the 5' G) was processed as described above, except in half amounts, resulting in a final volume of 25 µl for each of the first three adaptors and 12.5 µl for the final adaptor.

Non-radiolabeled counterparts to the above four adaptors were generated by adding 20.0 µl (100 pmole/µl) of each of the first three lower strands, separately to 20.0 µl (100 pmole/µl) of the upper strand, 8.0 µl of 10× T$_4$ DNA Ligase buffer and 32 µl H$_2$O, for a final volume of 80 µl, and 10.0 µl (100 pmole/µl) of the final lower strand (with the 5' G) was added to half amounts of the above constituents, for a final volume of 40 µl. Each of the eight sets of adaptors (four radiolabeled and four non-radiolabeled) were incubated at 93° C. for 30 seconds followed by annealing at 25° C. for 5 minutes. The radiolabeled final adaptor (with the 5' G) was added to 12.5 µl H$_2$O, to bring the final volume to 25 µl, like the other radiolabeled adaptors, and the 40 µl of the non-radiolabeled final adaptor was added to 40 µl H$_2$O, to bring the final volume to 80 µl, like the other non-radiolabeled adaptors. Each adaptor with a 5' G was at half the concentration of the other adaptors based on ligation data from preliminary experiments.

Each radiolabeled adaptor was added to 25 µl of the non-radiolabeled adaptors with the other three 5' ends. This resulted in four adaptor #1 mixes, each with one radiolabeled adaptor and the remaining three non-radiolabeled adaptors. Using four ligation mixtures allows one to sequence nucleotides using a single label and a simple detection apparatus (e.g. a scintillation counter).

Adaptor set #2 was made the same way as adaptor set #1, except that the four ligonucleotides for the lower strands of the adaptors were:

5'P-CNNNCATCCTCTGGGCTGCACGGG (SEQ ID NO:18) or

5'P-ANNNCATCCTCTGGGCTGCACGGG (SEQ ID NO:19) or

5'P-TNNNCATCCTCTGGGCTGCACGGG (SEQ ID NO:20) or

5'P-GNNNCATCCTCTGGGCTGCACGGG (SBQ ID NO:21);
only the 5' end varies between each of these four
oligonucleotides, and this nucleotide is
underlined; the FokI recognition sequence is in
bold type; N represents nucleotides with
4-fold degeneracy.

and the oligonucleotide for the upper strand of the adaptors was:

5'-CCCGTGCAGCCCAGAGGATG (SEQ ID NO:22);
the FokI recognition sequence is in bold type.

Initial Sequencing Template Generation

PCR amplification of a 93 bp initial template precursor from human genomic DNA was carried out as described in Example 1.

The samples were combined and mixed with 400 µl of washed magnetic streptavidin beads in 2× binding-wash buffer (prepared from 140 µl Dynabeads M-280 Streptavidin, Dynal, Oslo Norway, as directed by the manufacturer), incubated for 1 hour at room temperature (23° C.) with mixing to disperse the magnetic beads, magnetically pelleted (Dynal Magnetic Pellet Concentrator-E), washed three times in binding-wash buffer, and resuspended in 100 µl $H_2O$. This product was digested with 7.0 µl FokI (3U/µl; Boehringer Mannheim) in the manufacturer's 1× buffer in a total volume of 150 µl at 37° C. for 1 hour, with mixing every 15 minutes, magnetically pelleted, washed three times in binding-wash buffer, and the template was suspended in 50 µl $H_2O$.

Adaptor Ligation

The template underwent ligation separately to each of the four adaptor mixes in adaptor set #1 as follows: 12.5 µl of the template was added to 10 µl of each adaptor mix, 18.5 µl $H_2O$, 4.0 µl 10× $T_4$ DNA Ligase buffer, and 5.0 µl $T_4$ DNA Ligase (1.0 U/µl; Boehringer Mannheim, Indianapolis Ind.) and incubated at 23° C. for 1 hour with mixing every 15 minutes. Then, the mixture was magnetically pelleted, the pellets were washed three times in binding-wash buffer and then were resuspended in 50 µl TE (10.0 mM Tris-HCl pH 8.0, 1.0 mM EDTA).

Scintillation Counting

Forty µl each of the four ligated samples were added to 2.5 ml of scintillation fluid (Beckman Ready Gel, Beckman Instruments, Fullerton Calif.) in a scintillation vial and underwent scintillation counting using a Beckman LS 1801 scintillation counter.

PCR Amplification

One µl from each ligation (from the 10 µl remaining that did not undergo scintillation counting) underwent PCR amplification as was done in generating the initial template precursor, except that 42.6 µl $H_2O$ was used (instead of 41.6 µl) and the upper strand of sequencing adaptor set #1 was used as the PCR primer in place of Primer A.

Second Sequencing Cycle

The steps were identical to the first sequencing cycle, except that the adaptor set used for adaptor ligation was adaptor set #2, and the upper strand of sequencing adaptor set #2 was used as a PCR primer instead of the upper strand of sequencing adaptor set #1.

Third Sequencing Cycle

The template precursor that had been amplified in the second sequencing cycle underwent binding to magnetic streptavidin, FolkI digestion, adaptor ligation, and scintillation counting as was done in the second sequencing cycle, except that the adaptor set used for adaptor ligation was adaptor set #1.

Sequencing Results

The FokI recognition domain is positioned in each ligated adaptor so that one nucleotide was sequenced at 9 nucleotide intervals. The scintillation counts for each of the four adaptors at each sequencing interval (identified by sequencing cycle) is shown below. The highest counts are in bold type. The second adaptor set did not label as efficiently as the first adaptor set. Counts for the correct nucleotide were >12 fold greater than background (counts for any other nucleotide) in the first three cycles. Counts for the correct nucleotide were dominant for cycles 4 and 5, but were less than 2-fold over background.

| | Sequencing Cycle Number | | | | |
|---|---|---|---|---|---|
| | 1 | 2 | 3 | 4 | 5 |
| Template nucleotide at ligation junction | A | A | T | T | G |
| Predicted 5' end of adaptor undergoing ligation | <u>T</u> | <u>T</u> | <u>A</u> | <u>A</u> | <u>C</u> |
| Scintillation counts for adaptors (identified by $^{32}P$ labelled 3' end) | | | | | |
| G | 712 | 329 | 1,337 | 2,420 | 1,597 |
| A | 1,933 | 344 | 40,284 | 3,169 | 11,394 |
| T | 25,568 | 6,769 | 3,105 | 1,404 | 7,307 |
| C | 1,007 | 366 | 1,330 | 242 | 21,178 |

EXAMPLE 2

Demonstration of Interval Sequencing Mediated by Class-IIS Restriction Endonuclease Generated 3' Overhangs and Template-Directed Ligation A BseRI based protocol was used to sequence single nucleotides separated by intervals of eight nucleotides using a scintillation counter. The initial template precursor was a 103 bp PCR product containing a portion of the Cystic Fibrosis Transmembrane Conductance Regulator gene that had been amplified directly from human genomic DNA. Sequencing was accomplished by template-directed ligation using three sequencing cycles, and covered a span of 17 nucleotides (1+(2×8)=17). The non-biotinylated primer used to generate the template precursor contained a recognition domain for BseRI. The opposite primer had a biotinylated 5' end, and was used to bind the template precursor to magnetic streptavidin beads. During the sequencing cycles, only two sets of adaptors were used, and each unique PCR amplifying primer used during the sequencing cycles was identical to the upper strand of the previously used adaptor, except it did not have the final two nucleotides on the 3' end, so that these unique amplifying primers contained the BseRI recognition domain in their 3' ends ensuring sufficient length for efficient priming when using these adaptors. In this test protocol, identification of a nucleotide during each sequencing cycle took place using four ligation reactions (for the single template precursor). In each ligation, all four adaptors were present, with the 5' end of a different one of the four adaptors in each ligation tagged with $^{32}$P. Quantitation of retained $^{32}$P radiolabel was carried out using a scintillation counter. Signal for the correct nucleotide was four fold greater than background in each of the three cycles. The details are outlined below:

Sequencing Adaptor Generation

Adaptor set #1 (upper strands of this adaptor set are shown in the box below) was generated as follows: 4.0 µl of the upper strand of the four adaptors (100 pmole/µl) were added, in four separate reactions (one for each oligonucleotide) to 5.0 µl H$_2$O, 16.0 µl 10× Polynucleotide Kinase buffer (700 mM Tris-HCl (pH 7.6), 100 mM MgCl$_2$, 50 mM dithiothreitol), 10.0 µl T$_4$ Polynucleotide Kinase (10U/µl; New England BioLabs, Beverly Mass.) and 125.0 µl [$^{32}$P]ATP (2.0 µCi/µl). All of the samples were incubated at 37° C. for one hour followed by heat inactivation at 65° C. for 20 minutes. Unincorporated [$^{32}$P]ATP was removed from each tube using a Qiagen nucleotide removal column (Qiagen, Chatsworth Calif.) and each oligonucleotide was eluted in 50 µl TE.

```
5' CGCACGGCTGGGTCGGAGGAGNC (SEQ ID NO:23) or

5' CGCACGGCTGGGTCGGAGGAGNA (SEQ ID NO:24) or

5' CGCACGGCTGGGTCGGAGGAGNI (SEQ ID NO:25) or

5' CGCACGGCTGGGTCGGAGGAGNG (SEQ ID NO:26);
only the 3' end varies between each
oligonucleotide, and this nucleotide is
underlined; the BseRI recognition sequence is in
bold type; N represents nucleotides with
4-fold degeneracy.
```

The four labeled oligonucleotides (8 pmole/µl) were separately added to an equal volume of the lower strand of the adaptor

```
(CTCCTCCGACCCAGCCGTGCG (SEQ ID NO:27);
the BseRI recognition sequence is in bold type.
``` suspended in 2× T$_4$ DNA Ligase buffer (8 pmole/µl). Non-radiolabeled counterparts to the above four adaptors were generated as follows: Unlabeled upper strands of the adaptors (8 pmole/µl) were added, separately, to an equal volume of the lower strand of the adaptor suspended in 2× T$_4$ DNA Ligase buffer (8 pmole/µl). Each of the eight sets of adaptors (four radiolabeled and four non-radiolabeled) were incubated at 93° C. for 30 seconds followed by annealing at 25° C. for 5 minutes. Five µl of each radiolabeled adaptor was added to 5 µl of those non-radiolabeled adaptors with the other three 3' ends. This resulted in four adaptor #1 mixes, each with one radiolabeled adaptor and the remaining three non-radiolabeled adaptors.

Adaptor set #2 was made the same way as adaptor set #1, except that the four oligonucleotides for the upper strands of the adaptors were:

```
5' GGTGCGCCAGTCCAGCGAGGAGNC (SEQ ID NO:28) or

5' GGTGCGCCAGTCCAGCGAGGAGNA (SEQ ID NO:29) or

5' GGTGCGCCAGTCCAGCGAGGAGNT (SEQ ID NO:30) or
```

-continued
```
5' GGTGCGCCAGTCCAGCGAGGAGNG (SEQ ID NO:31);
only the 3' end varies between each
oligonucleotide, and this nucleotide is
underlined; the BseRI recognition sequence is in
bold type: N represents nucleotides with
4-fold degeneracy.
```

The oligonucleotide for the lower strand of the adaptors was:

```
(CTCCTCGCTGGACTGGCGCACC;              (SEQ ID NO:32)

the BseRI recognition sequence is in bold type.
```

Initial Sequencing Template Generation

PCR amplification of a 103 bp initial template precursor from human genomic DNA was carried out as in Example 1, except that Primer A had the following sequence:

```
                                      (SEQ ID NO:33)

5'TCTGTTCTCAGTTTTCCTGGATGAGGAGTGGCACC;

mismatches to genomic DNA underlined;
BseRI recognition sequence in bold type.
```

The samples were combined, and the 400 µl was digested with 5.0 µl BseRI (4U/µl; New England BioLabs) in the manufacturer's 1× buffer in a total volume of 460 µl at 37° C. for 1 hour followed by heat inactivation at 65° C. for 20 minutes. This product was mixed with 460 µl of washed magnetic streptavidin beads (140 µl Dynabeads washed and then suspended in 2× binding-wash buffer following the manufacturer's instructions), incubated for 1 hour at room temperature (23° C.) with mixing to disperse the magnetic beads, magnetically pelleted (Dynal Magnetic Pellet Concentrator-E), washed three times in binding-wash buffer, and resuspended in 50 µl TE.

Adaptor Ligation

The template underwent ligation separately to each of the four adaptor mixes in adaptor set #1 as follows: 12.5 µl of the template was added to 20 µl of each adaptor mix, 9.5 µl H$_2$O, 3.0 µl 10× T$_4$ DNA Ligase buffer, and 5.0 µl T$_4$ DNA Ligase (1.0 U/µl; Boehringer Mannheim, Indianapolis Ind.) and incubated at 23° C. for 1 hour with mixing every 15 minutes. Then, the mixture was magnetically pelleted, and the pellets were washed three times in binding-wash buffer and then were resuspended in 50 µl TE.

Scintillation Counting

Twenty five µl of each of the four ligated samples was added to 2.5 ml of scintillation fluid (Beckman Ready Gel) in a scintillation vial and underwent scintillation counting using a Beckman LS 1801 scintillation counter.

PCR Amplification

One µl from each ligation (of the 10 µl remaining that did not undergo scintillation counting) underwent PCR amplification as was done in generating the initial template precursor, except that 42.6 µl H$_2$O was used (instead of 41.6 µl) and

```
5'CGCACGGCTGGGTCGGAGGAG;               (SEQ ID NO:34)

BseRI recognition sequence is in bold type.
``` was used as the PCR primer in place of Primer A.

Second Sequencing Cycle

The steps were identical to the first sequencing cycle, except that the adaptor set used for adaptor ligation was adaptor set #2, and

5'GGTGCGCCAGTCCAGCGAGGAG; (SEQ ID NO:35)

BseRI recognition sequence is in bold type.

was used as the PCR primer replacing primer A.

Third Sequencing Cycle

The template precursor that had been amplified in the second sequencing cycle underwent BseRI digestion, binding to magnetic streptavidin, adaptor ligation and scintillation counting as was done in the second sequencing cycle, except that the adaptor set used for adaptor ligation was adaptor set #1.

Sequencing Results

The BseRI recognition domain is positioned in each ligated adaptor so that one nucleotide was sequenced at 8 nucleotide intervals. The initial template precursor is shown below, along with its BseRI recognition domain (bold type). Underlined sequences are the original amplifying primers (Primer A and Primer B). The cut sites for this recognition domain, as well as subsequent cut sites directed by ligated adaptors, are shown by dissecting lines. Cleavage generates a single-strand overhang that constitutes a template, and the nucleotide sequenced at each interval is shown by a numbered asterisk, the number identifying the sequencing cycle for sequencing the nucleotide.

The scintillation counts for each of the four adaptors at each sequencing interval (identified by sequencing cycle) is shown below. The highest counts are in bold type. Signal for the correct nucleotide was four fold greater than background in each of the three cycles.

|  | Sequencing Cycle Number | | |
|---|---|---|---|
|  | 1 | 2 | 3 |
| Template nucleotide at ligation junction | A | T | A |
| Predicted 3' end of adaptor undergoing ligation | T | A | T |
| Scintillation counts for adaptors (identified by phophorylated 5' end) | | | |
| G | 146,170 | 111,660 | 100,550 |
| A | 130,570 | 507,140 | 32,023 |
| T | 1,290,660 | 83,787 | 668,140 |
| C | 209,660 | 95,120 | 51,515 |

This invention was also tested to see whether it could detect a heterozygote for the cystic fibrosis delta 508 mutation. In this carrier, one would expect the third cycle to detect both an A and a C (ligation of adaptors with a 3' T or G). In this test, all adaptors with a 3' G were at half the concentration used previously, since the adaptors with a 3' G tended to give higher background counts, and following the sequencing of the initial template, templates were diluted 1:10 prior to PCR amplification. The results are shown below:

|  | Sequencing Cycle Number | | |
|---|---|---|---|
|  | 1 | 2 | 3 |
| Template nucleotide at ligation junction | A | T | A and C |
| Predicted 3' end of adaptor undergoing ligation | T | A | T and G |
| Scintillation counts for adaptors (identified by phophorylated 5' end) | | | |
| G | 38,430 | 42,824 | 102,340 |
| A | 77,540 | 198,350 | 10,968 |
| T | 598,840 | 40,092 | 110,640 |
| C | 125,320 | 47,620 | 21,430 |

The heterozygote was clearly detected with counts four fold higher for each of the two predicted nucleotides over the background counts for the other nucleotides.

EXAMPLE 3

Demonstration of Interval Sequencing Template Generation Mediated by Class-IIS Restriction Endonuclease Generated 5' Overhangs, Template-Directed Polymerization and Adaptor Ligation FokI based protocol was used to generate a series of templates separated by intervals of nine nucleotides. The initial template precursor was the identical 93 bp PCR product that was used as the initial template precursor in Example 1. During the sequencing cycles, only two adaptors were used, and each unique PCR amplifying primer used during the sequencing cycles was identical to the upper strand of the previously used adaptor. In this test protocol, sequencing was simulated by the incorporation of a ddNTP into the template during five sequencing cycles, and successful trimming of the template was confirmed by acrylamide gel resolution of the PCR products constituting the template precursors during each simulated sequencing cycle. The template was trimmed as predicted over the five sequencing cycles. The details are given below:

Sequencing Adaptor Generation

Adaptor #1 was generated as follows:

30 μl of the lower strand of adaptor #1 (100 pmole/μl):

5'NNNCATCCGACCCAGGCGTGCG; (SEQ ID NO:36)

the FokI recognition sequence is in bold type;
N represents nucleotides with 4-fold degeneracy.

and 30 μl of the upper strand of adaptor #1 (100 pmole/μl):

5'CGCACGCCTGGGTCGGATG; (SEQ ID NO:37)

the FokI recognition sequence is in bold type.

were added to 12 μl $H_2O$ and to 8.0 μl 10× $T_4$ DNA Ligase buffer. The adaptor was incubated at 93° C. for 30 seconds followed by annealing at 25° C. for 5 minutes.

Adaptor #2 was made the same way as adaptor set #1, except that the oligonucleotide for the lower strand of adaptor #2 was:

5'NNNCATCCTCTGGGCTGCACGGG; (SEQ ID NO:38)

the FokI recognition sequence is in bold type;
N represents nucleotides with 4-fold degeneracy.

and the oligonucleotide for the upper strand of the adaptors was:

5'CCCGTGCAGCCCAGAGGATG; (SEQ ID NO:39)

the FokI recognition sequence is in bold type.

Initial Sequencing Template Generation

PCR amplification of a 93 bp initial template precursor from human genomic DNA was carried out as described in Example 1, except that only 100 µl (one tube) was amplified. Following PCR amplification, 50 µl was removed to be run on a acrylamide gel later. The remaining 50 µl was mixed with 100 µl of washed magnetic streptavidin beads (16 µl Dynabeads M-280 Streptavidin washed and suspended in 2× binding-wash buffer) and 50 µl H$_2$O, incubated for 1 hour at 23° C. with mixing, magnetically pelleted, washed three times in binding-wash buffer, and resuspended in 50 µl H$_2$O. This product was digested with 1.0 µl FokI (3U/µl) with mixing every 15 minutes in the 1× restriction endonuclease-buffer in a total volume of 100 µl at 37° C. for 1 hour, magnetically pelleted, washed three times in binding-wash buffer, and resuspended in 25 µl H$_2$O.

Template Directed Polymerization Using Nucleotide Terminators

This product was added to 10 µl of each ddNTP (500 µM each), 14 µl H$_2$O, 20 µl 5× Sequenase buffer, and 1.0 µl Sequenase (Amersham) and was incubated at 23° C. for 20 minutes with mixing every 10 minutes. The mixture was magnetically pelleted, washed three times in binding-wash buffer and suspended in 25 µl TE.

Adaptor Ligation

The template (following simulated sequencing by ddNTP fill-in) underwent ligation to adaptor #1 as follows: 25 µl of the template was added to 10 µl of adaptor #1, 6.0 µl H$_2$O, 4.0 µl 10× T$_4$ DNA Ligase buffer, and 5.0 µl T$_4$ DNA Ligase (1.0 U/µl) and incubated at 23° C. for 1 hour with mixing every 15 minutes. Then, the mixture was magnetically pelleted, washed three times in binding-wash buffer, and suspended in 50 µl TE.

PCR Amplification

1 µl from the ligation underwent PCR amplification as was done in generating the initial template precursor, except that 42.6 µl H$_2$O was used (instead of 41.6 µl) and the upper strand of adaptor #1 was used as the PCR primer in place of Primer A.

Second Sequencing Cycle

The steps were identical to the first sequencing cycle, except that the adaptor used for adaptor ligation was adaptor #2, and the upper strand of adaptor #2 was used as a PCR primer instead of the upper strand of adaptor #1.

Third Sequencing Cycle

Identical to the second sequencing cycle, except that the adaptor used for adaptor ligation was adaptor #1, and the upper strand of adaptor #1 was used as a PCR primer instead of the upper strand of adaptor #2.

Subsequent Sequencing Cycles

Following the third sequencing cycle, the second sequencing cycle was repeated, and following this second sequencing cycle, the third sequencing cycle was repeated.

Results

Figure 5:
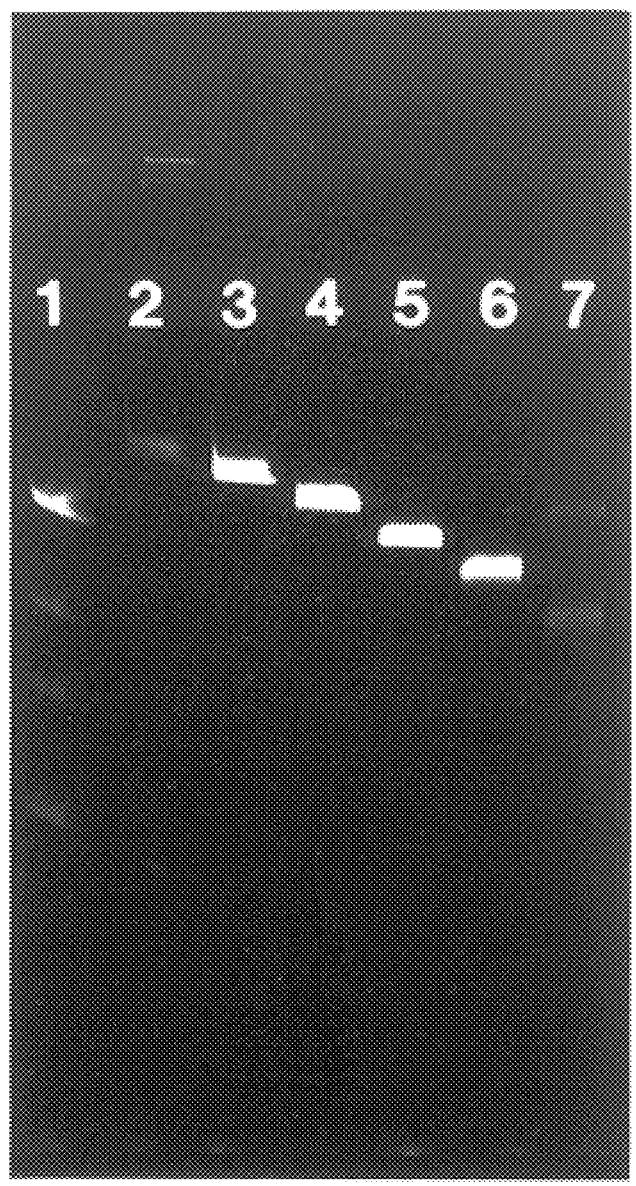
FIG. 5 is a photograph depicting the size of the initial template precursor and of subsequent template precursors following each of five iterative sequencing simulation cycles consisting of FokI digestion, adaptor ligation, fill-in with ddNTPs, and PCR amplification, run on a 12% denaturing acrylamide gel. Lane 1, MW markers (17-mer, 25 -mer, 37-mer, 48-mer, 70-mer); Lane 2, Initial template precursor: 93 base pair PCR product amplified from human genomic DNA; Lane 3, Template precursor following sequencing cycle #1 (90 bp); Lane 4, Template precursor following sequencing cycle #2 (82 bp); Lane 5, Template precursor following sequencing cycle #3 (72 bp); Lane 6, Template precursor following sequence cycle #4 (64 bp); Lane 7, Template precursor following sequencing cycle #5 (54 bp).

Following each PCR amplification, generating the template precursors, 50 µl were removed and were later run on a acrylamide gel, as shown in FIG. 5. Following the sequencing cycles 1–5, the template precursor was trimmed as predicted, with high specificity in the first four sequencing cycles, and some extraneous product in the template-precursor following the fifth sequencing cycle.

EXAMPLE 3B

Demonstration of Interval Sequencing Mediated by Class-IIS Restriction Endonuclease Generated 5' Overhangs, Template-Directed Polymerization and Adaptor Ligation This example is essentially the same as Example 3, except that during each template-directed polymerization with ddNTPs, a $^{33}$P labeled ddNTP was substituted for its corresponding normal ddNTP, in four separate template-directed polymerizations, each with a single and different radiolabeled ddNTP. Then, an aliquot from each of these reactions underwent scintillation counting.

Sequencing Adaptor Generation

Sequencing adaptor generation was carried out as described in Example 3.

Initial Sequencing Template Generation

PCR amplification of the initial template precursor from human genomic DNA was carried out as described in Example 3, except that two tubes were amplified (200 µl). Following PCR amplification, the entire PCR product was bound to 200 µl of washed magnetic streptavidin beads (64 µl Dynabeads M-280 Streptavidin washed and suspended in 2× binding-wash buffer), incubated for 1 hour at 23° C. with mixing, magnetically pelleted, washed three times in binding-wash buffer, and resuspended in 100 µl H$_2$O. This product was digested with 4.0 µl FokI (3U/µl) in the corresponding 1× restriction endonuclease buffer in a total volume of 150 µl at 37° C. for 1 hour with mixing every 15 minutes, magnetically pelleted, washed three times in binding-wash buffer, and resuspended in 100 µl H$_2$O.

Template Directed Polymerization Using Nucleotide Terminators

25 µl underwent four separate template directed polymerizations using ddNTPs, each exactly as was done in Example 3, except a different three non-radiolabeled ddNTPs were added in each reaction, with the fourth ddNTP being 5.0 µl of the corresponding $^{33}$PddNTP (0.45 µCi/µl; Amersham). Also, 19 µl H$_2$O were used instead of 14 µl H$_2$O, and 3U of Sequence (1.2 µl of a 1:5 dilution in 1× Sequenase buffer) were used instead of 1 µl of undiluted Sequenase (13U/µl). Following incubation for 20 minutes at 23° C. with mixing every 10 minutes, each mixture was magnetically pelleted, washed three times in binding-wash buffer and suspended in 50 µl H$_2$O.

Scintillation Counting

40 µl underwent scintillation counting as described in Example 1.

Adaptor Ligation

The remaining 10 µl of each of the four samples were combined, and underwent adaptor ligation as in Example 3, except that 10 µl of 10× ligase buffer and 35 µl H$_2$O were used, resulting in a final volume of 100 µl, and following ligation, magnetic pelleting and washing, the pellet was suspended in 25 µl TE.

PCR Amplification

One µl from the ligation underwent PCR amplification in each of two tubes as was done in generating the initial template precursor, except that 42.6 pi H$_2$O was used (instead of 41.6 μl) and the upper strand of adaptor #1 was used as the PCR primer in place of Primer A.

Second Sequencing Cycle

The steps were identical to the first sequencing cycle, except that the adaptor used for adaptor ligation was adaptor #2, and the upper strand of adaptor #2 was used as a PCR primer instead of the upper strand of adaptor #1.

Third Sequencing Cycle

Identical to the second sequencing cycle, except that the adaptor used for adaptor ligation was adaptor #1, and the upper strand of adaptor #1 was used as a PCR primer instead of the upper strand of adaptor #2.

Subsequent Sequencing Cycles

Following the third sequencing cycle, the second sequencing cycle was repeated, and following this second sequencing cycle, the third sequencing cycle was repeated through the scintillation counting step.

Sequencing Results

Figure 7:
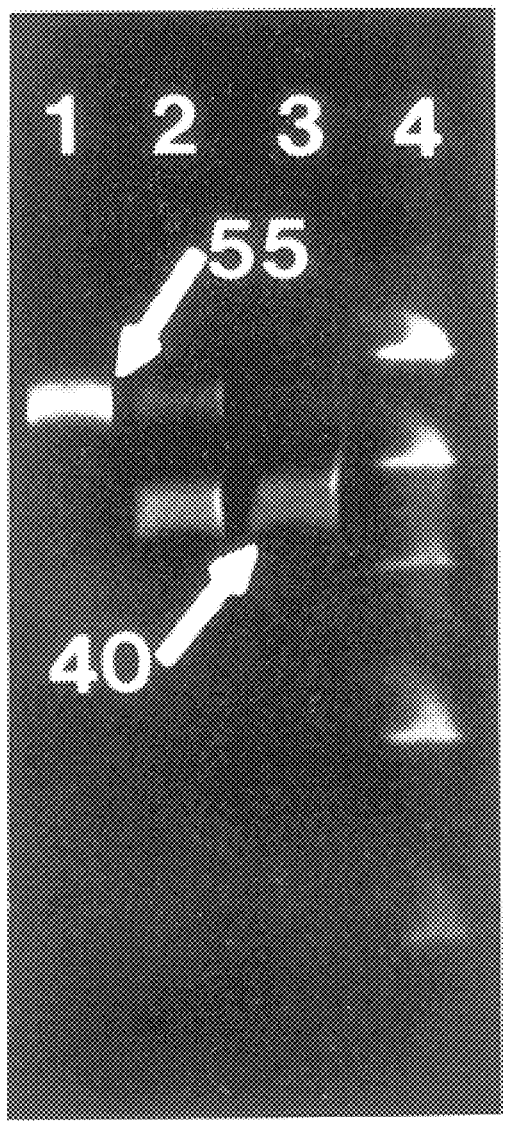
FIG. 7 is a photograph depicting Dpn I cutting of a PCR product, such cutting directed by a methylated primer sequence, run on an acrylamide gel: lane 1, 33 μl (1 μg) of uncut 55 bp PCR product; lane 2, 33 μl of 55 bp PCR product cut with 20 U DpnI, generating a 40 bp product; lane 3, 33 μl of 55 bp PCR product cut with 100 U Dpn I, generating a 40 bp product; lane 4, MW markers (17-mer, 25-mer, 37-mer, 48-mer, 70-mer).

The scintillation counts at each sequencing interval (identified by sequencing cycle) are shown below. The highest counts are in bold type. Counts for the correct nucleotide were greater than 3.50 fold greater than background (counts for any other nucleotide) in each of the five cycles.

the original PCR product and its DpnI digestion product is shown in FIG. 7.

PCR Product Generation With a Primer Encoded Hemi-Methylated Dpn I Recognition Domain PCR amplification of a 55 bp product from 4 ng of the plasmid pUC19 was carried out using 1.6 μl rTth DNA Polymerase (2.5 U/μl; Perkin Elmer) in a 1×Tth DNA polymerase buffer (20 mM Tricine pH 8.7, 85 mM KOAc, 8% glycerol, 2% (vol/vol) DMSO, 1.1 mM Mg(OAc)2), and 200 μM each dNTP with 25 pmoles of each of the primers shown in the box below, using the following parameters: 94° C. for 1 minute followed by 30 thermal cycles (94° C. for 30 seconds, 45° C. for 30 seconds), a final extension at 72° C. for 7 minutes, and a 4° C. soak.

```
Primer A: 5'CCATCCGTAAGATGATCTTCTG
(SEQ ID NO: 40);
mismatches to pUC19 DNA underlined;
DpnI recognition sequence in bold type.
The A was methylated, and was incorporated during
oligonucleotide synthesis using a methylated
phosphoramidite (Glenn Research).
Primer B: 5'CTCAGAATGACTTGGTTG (SEQ ID NO: 41).
```

Digestion With DpnI

33 μl of this product was digested with 1.0 μl or 5.0 μl DpnI (20U/μl; New England BioLabs) in the manufacturer's

|  | Sequencing Cycle Number | | | | |
| --- | --- | --- | --- | --- | --- |
|  | 1 | 2 | 3 | 4 | 5 |
| Template nucleotide adjacent to double-stranded domain | A | A | T | T | G |
| Predicted ddNTP incorporated by template-directed polymerization | T | T | A | A | C |
| Scintillation counts for incorporated $^{33}$P labelled ddNTPs | | | | | |
| G | 51,444 | 20,848 | 74,217 | 261,280 | 12,436 |
| A | 255,340 | 58,063 | 3,433,960 | 2,805,872 | 167,928 |
| T | 897,960 | 2,061,827 | 9,434 | 43,309 | 229,760 |
| C | 13,124 | 7,490 | 7,877 | 18,042 | 886,184 |

EXAMPLE 4

This example demonstrates a method that uses restriction endonuclease digestion to selectively remove primer directed sequence from a PCR product, without using a free methylated nucleotide during PCR amplification. This demonstration is the first use of a PCR primer with a methylated recognition domain sequence designed to permit selective cleavage directed by the primer encoded end of a PCR product. In the context of the sequencing method of this invention, when generating initial sequencing templates, the ability to remove PCR primer encoded sequence and its complement at the end to be sequenced decreases the number of cycles necessary to sequence PCR product that lies beyond the primer.

There is currently only one commercially available restriction endonuclease, Dpn I, that requires a methylated sequence for cutting. Dpn I recognizes the sequence GATC, where the A is methylated. Cutting by Dpn I generates a blunt end. The methylated A was incorporated into the primer sequence during routine oligonucleotide synthesis, as methyl A is commercially available as a phosphoramidite. PCR amplification occurred using regular non-methylated nucleotides, so no portion of any PCR product, apart from the methylated primer, was methylated. A 55 bp PCR product was amplified from the plasmid pUC19. This 55 bp PCR product and its 40 bp DpnI digest product are illustrated in FIG. 6, and the denaturing acrylamide gel showing 1× buffer in a total volume of 40 μl at 37° C. for 1 hour. The initial PCR product and its DpnI cut portions were each run on a denaturing acrylamide gel, as shown in FIG. 7. Dpn I cut the PCR end to very near completion (FIG. 7). In this example, the DpnI site was created near the 3' end of the primer, and incorporating this recognition domain required two mismatches to the original template. This illustrates that Dpn I, with its short 4 bp recognition domain, can be readily incorporated near the 3' end of a primer without preventing PCR amplification. For the sequencing of inserts cloned in a vector insert, the recognition domain can be placed in the immediate 3' end of the amplifying primer, because its nucleotide sequence can be encoded in the vector adjacent to the inserts to be sequenced. Following digestion with DpnI, an end is generated that can be ligated to the initial adaptors with offset recognition domains for the class-IIS restriction endonuclease used in sequencing the insert.

EQUIVALENTS

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method for removing all or a part of a primer sequence from a primer extended product, comprising:
    a) providing a primer sequence comprising a methylated portion of a restriction endonuclease recognition domain, wherein recognition of said domain by a restriction endonuclease requires at least one methylated nucleotide;
    b) performing template-directed primer extension using said primer and a nucleic acid segment to generate a primer extended product; and
    c) digesting said primer extended product with a restriction endonuclease that recognizes the resulting double-stranded restriction endonuclease recognition domain comprised by said primer sequence in said primer extended product.

2. The method of claim 1, wherein a sequence complementary to said primer sequence is also removed by said restriction endonuclease digestion in said step (c).

3. The method of claim 1, wherein said restriction endonuclease of step (c) is a class-IIS restriction endonuclease.

4. The method of claim 3, wherein said digestion with said class IIS restriction endonuclease of step (c) generates a single-strand extension no longer than 10 nucleotides in length that is not encoded by said primer comprising at least part of said restriction endonuclease recognition domain.

5. The method of claim 1, wherein said template-directed primer extension in said step (b) occurs during nucleic acid amplification in vitro.

6. The method of claim 5, wherein said nucleic acid amplification in vitro is linear.

7. The method of claim 5, wherein said nucleic acid amplification in vitro is exponential.

8. The method of claim 7, wherein said nucleic acid amplification in vitro is PCR.

9. The method of claim 7, wherein said nucleic acid amplification in vitro is strand displacement amplification.

10. A method for blocking a restriction endonuclease recognition domain in a primer extended product, comprising:
    a) providing a primer with at least one modified nucleotide, wherein said modified nucleotide blocks an enzyme recognition domain, and wherein said primer comprises at least a portion of said enzyme recognition domain sequence;
    b) performing template-directed primer extension using said primer and a nucleic acid segment to generate a primer extended product; and
    c) digesting said primer extended product with an enzyme that recognizes a double-stranded enzyme recognition domain in said primer extended product; to thereby block cutting mediated by said restriction endonuclease recognition domain in said primer extended product.

11. The method of claim 10, wherein said modified nucleotide is a methylated nucleotide.

12. The method of claim 10, wherein said template directed primer extension in said step (b) occurs during nucleic acid amplification in vitro.

13. The method of claim 12, wherein said amplification in vitro is linear.

14. The method of claim 12, wherein said amplification in vitro is exponential.

15. The method of claim 14, wherein said amplification in vitro is PCR.

16. The method of claim 14, wherein said amplification in vitro is strand displacement amplification.

17. The method of claim 10, wherein said nucleic acid segment is part of a construct consisting of an insert in a vector.

* * * * *

UNITED STATES PATENT AND TRADEMARK OFFICE
CERTIFICATE OF CORRECTION

PATENT NO. : 6,190,889 B1
DATED : February 20, 2001
INVENTOR(S) : Douglas H. Jones Page 1 of 1

It is certified that error appears in the above-identified patent and that said Letters Patent is hereby corrected as shown below:

Column 1,
Line 3, please insert

-- <u>Government Funding</u>

Work described herein was supported by the funding from the National Institutes of Health Grants HG00569 and HG00835. The U.S. Government therefore may have certain rights in this Invention. --

Signed and Sealed this

Twenty-first Day of May, 2002

Attest:

Attesting Officer

JAMES E. ROGAN
Director of the United States Patent and Trademark Office